United States Patent
Alkon et al.

(10) Patent No.: US 9,163,032 B2
(45) Date of Patent: Oct. 20, 2015

(54) ESTERS OF DCPLA AND METHODS OF TREATMENT USING THE SAME

(71) Applicant: Blanchette Rockefeller Neurosciences Institute, Morgantown, WV (US)

(72) Inventors: Daniel L. Alkon, Chevy Chase, MD (US); Thomas J. Nelson, Morgantown, WV (US)

(73) Assignee: Blanchette Rockefeller Neurosciences Insitute, Morgantown, WV (US)

( * ) Notice: Subject to any disclaimer, the term of this patent is extended or adjusted under 35 U.S.C. 154(b) by 0 days.

(21) Appl. No.: 14/357,654

(22) PCT Filed: Nov. 13, 2012

(86) PCT No.: PCT/US2012/064783
§ 371 (c)(1),
(2) Date: May 12, 2014

(87) PCT Pub. No.: WO2013/071281
PCT Pub. Date: May 16, 2013

(65) Prior Publication Data
US 2014/0323456 A1    Oct. 30, 2014

Related U.S. Application Data

(60) Provisional application No. 61/559,117, filed on Nov. 13, 2011.

(51) Int. Cl.
A61K 31/275 (2006.01)
C07D 493/22 (2006.01)
C07C 69/608 (2006.01)
C07J 9/00 (2006.01)
C07C 403/12 (2006.01)
C07C 403/20 (2006.01)

(52) U.S. Cl.
CPC ............ *C07D 493/22* (2013.01); *C07C 69/608* (2013.01); *C07C 403/12* (2013.01); *C07C 403/20* (2013.01); *C07J 9/00* (2013.01); *C07C 2101/02* (2013.01); *C07C 2101/16* (2013.01)

(58) Field of Classification Search
USPC .......................................... 514/526; 560/129
See application file for complete search history.

(56) References Cited

U.S. PATENT DOCUMENTS

| 4,001,428 A | 1/1977 | Kosower et al. |
| 5,242,932 A | 9/1993 | Gandy et al. |
| 5,385,915 A | 1/1995 | Buxbaum et al. |
| 6,077,686 A | 6/2000 | Der et al. |
| 6,080,582 A | 6/2000 | Alkon et al. |
| 6,080,784 A | 6/2000 | Driedger et al. |
| 6,107,050 A | 8/2000 | Alkon et al. |
| 7,595,167 B2 | 9/2009 | Khan et al. |
| 7,799,782 B2 * | 9/2010 | Munson et al. ............ 514/234.5 |
| 2001/0051344 A1 | 12/2001 | Shalon et al. |
| 2003/0108956 A1 | 6/2003 | Alkon et al. |
| 2003/0153014 A1 | 8/2003 | Shen et al. |
| 2004/0014678 A1 | 1/2004 | Favit et al. |
| 2004/0086905 A1 | 5/2004 | Das et al. |
| 2005/0059092 A1 | 3/2005 | Zhao et al. |
| 2005/0075393 A1 | 4/2005 | Nishizaki et al. |
| 2007/0082366 A1 | 4/2007 | Khan et al. |
| 2009/0029873 A1 | 1/2009 | Khan et al. |
| 2010/0022645 A1 | 1/2010 | Nelson |

FOREIGN PATENT DOCUMENTS

| EP | 0 735 370 A | 10/1996 |
| JP | 06-279311 | 10/1994 |
| JP | 10-090263 A | 4/1998 |
| WO | WO 93/11231 A | 6/1993 |
| WO | WO 00/20867 A | 4/2000 |
| WO | WO 00/70099 | 11/2000 |
| WO | WO 01/69244 A2 | 9/2001 |
| WO | WO 02/10768 A2 | 2/2002 |
| WO | WO 02/50013 A1 | 6/2002 |
| WO | WO 00/67764 | 9/2002 |
| WO | WO 03/102016 A2 | 12/2003 |
| WO | WO 2004/083241 A2 | 9/2004 |
| WO | WO 2006/050475 | 5/2006 |
| WO | WO 2006/054979 A1 | 5/2006 |
| WO | WO 2007/043998 | 4/2007 |
| WO | WO 2007/044094 A1 | 4/2007 |
| WO | WO 2007/047029 | 4/2007 |
| WO | WO 2007/149985 A2 | 12/2007 |
| WO | WO 2008/100449 | 8/2008 |
| WO | WO 2008/148115 A1 | 12/2008 |
| WO | WO 2009/101321 A2 | 8/2009 |
| WO | WO 2011053870 A1 | 5/2011 |

OTHER PUBLICATIONS

Harvey's CAS: 114: 206360, 1991.*
Database WPI, Week 200430, AN 2004-326064 Thomson Scientific, London, (Nov. 10, 2003).
Office Action mailed Mar. 3, 2015, U.S. Appl. No. 13/774,049.
Adachi, M., Fukuda et al., "Two Co-existing Mechanisms for Nuclear Import of MAP Kinase: Passive Diffusion of a Monomer and Active Transport of a Dimmer", EMBO J., 18, 5347-5358 (1999).
Alessi, D.R, Gomez et al., "Inactivation of p42 MAP Kinase by Protein Phosphatase 2A and a Protein Tyroin Phosphatase, but not CLIOO, in Various Cell Lines", Curf. Biol. 5, 283-295 (1995).
Alkon et al., Protein Synthesis Required for Long-Term Memory is Induced by PKC Activation on Days Before Associative Learning, Proc. Natl. Acad. Sci. USA,102:16432-16437 (2005).

(Continued)

*Primary Examiner* — Rei-Tsang Shiao
(74) *Attorney, Agent, or Firm* — Finnegan, Henderson, Farabow, Garrett & Dunner LLP

(57) ABSTRACT

The present disclosure relates to esters of 8-[2-(2-pentyl-cyclopropylmethyl)cyclopropyl]-octanoic acid ("DCPLA"). The disclosure further relates to compositions, kits, and methods for treatment using the esters.

21 Claims, 20 Drawing Sheets

(56) References Cited

OTHER PUBLICATIONS

Anderson et al., "Oxidative Signaling and Inflammatory Pathways in Alzheimer's Disease," Biochem. Soc. Symp., 67:141-149 (2001).
Arendt et al., "Increased Expression and Subcellular Translocation of the Mitogen Activated Protein Kinase and Mitogen-Activated Protein Kinase in Alzheimer's Disease," Neuroscience, 68(1):5-18 (1995).
Bailn et al., "Normal replicative lifespan of Alzheimer skin fibroblasts", Neurobiol Aging, vol. 9, pp. 195-198 (1988).
Baker et al., "System Manifestation of Alzheimer's Disease," Age, 11:60-65 (1988).
Barrow et al., "Functional Phenotype in Transgenic Mice Expressing Mutant Human Presenilin-1," Neurobiology of Disease 7, 119-126 (2000).
Bassa BV, et al.,."Lysophosphatidylcholine Activates Mesangial Cell PKKC and Map Kinase by PLCy-1 and Tyrosine Kinase-Ras Pathways," Am J Physiol, 277:F328-2337 (1999).
Becton, Dickenson& Co., "BD GentestTM Primary Hepatocytes," 13 (2008).
Bernier et al., "Bradykinin-regulated Interactions of the Mitogen-activated Protein Kinase Pathway with the Endothelial Nitric-oxide Synthase," J. Biol. Chem., 275:30707-30715 (2000).
Berridge, "Inositol Triphosphate and Diacylglycerol as Second Messengers," Biochem J., 220:345-360 (1984).
Biernat et al., "Phosphorylation of Ser 262 Strongly Reduces Binding of Tau to Microtubules: Distinction between PHF-like Immunoreactivity and Microtubule Binding," Neuron, 11:153-163 (1993).
Billingsley, M.L. et al.,."Regulated Phosphorylation and Dephosphorylation of tau Protein: Effects on Microtubule Interaction, Intracellular Trafficking and Neurodegeneration", Biochem. J. 323,557-591 (1997).
Blanchard et al., "Hyperphosphorylation of Human TAU by Brain Kinase PK40et beyond Phosphorylation by cAMP-dependent PKA: Relation to Alzheimer's Disease." Biochem. Biophys. Res. Commun., 200(1):187-194 (1994).
Blobe et al., "Regulation of protein kinase C and role in cancer biology," Cancer Metast. Rev. 1994; 13:411-431.
Bockman et al., "Kinins and Kinin Receptors: Importance for the Activation of Leukocytes," Journal of Leukocyte Biology, 68 (Nov. 2000).
Bondy et al., "The PHA-Induced Calcium Signal in Lymphocytes is Altered After Blockade of K+-Channels in Alzheimer's Disease," J. Psychiat. Res., 30(3):217-227 (1996).
Braconi Quintaje, S:B. et al., "Role of Protein Phosphatase 2a in the Regulation of Mitogen activated Protein Kinase Activity in Ventricular Cardiomyocytes", Biochem. Biophys. Res. Commun. 221, 539-547 (1996).
Brooks et al., "Gene Expression Profiles of Metabolic Enzyme Transcripts in Alzheimer's Disease," Brain Res, 1127(1):127-135 (2007).
Brunet, A., Roux et al., "Nuclear translocation of p42/p44 Mitogen-activated Protein Kinase is Required for Growth Factor-induced Gene Expression and Cell Cycle Entry", EMBO J. 18,664-674 (1999).
Burke et al., "Update on Alzheimer's Disease: Promising advances in Detection and Treatment," Postgraduate Medicine, 106(5) (1999).
Bush, et al., "βA4 Amyloid Protein and its Precursor in Alzheimer's Disease," Pharmacol Ther., 56:97-117 (1992).
Buxbaum et al., "Evidence That Tumor Necrosis Factor a Converting Enzyme is Involved in Regulated a-Secretase Cleavage of the Alzheimer Amyloid Protein Precursor," The Journal of Biological Chemistry, 273(43):27765-27767 (1998).
Caporaso et al., "Protein Phosphorylation Regulates Secretion of Alzheimer B/A4 Amyloid Precursor Protein," Proc. Natl. Acad. Sci. USA, 89:3055-3059 (Apr. 1992).
Carmeliet et al., "Growth properties and in vitro life span of Alzheimer disease and Down syndrome fibroblasts-a blind study", Mech. Aging Dev., vol. 53, pp. 17-33 (1990).
Chapman et al., "Genes, Models and Alzheimer's Disease," Trends in Genetics, 17(5) (May 2001).

Chen, RH. et al., "Nuclear Localization and Regulation of Erk and rsk Encoded Protein Kinases", Mol. Cell. Biol. 12,915-927 (1992).
Cheung et al., "Natural Variation in Human Gene Expression Assessed in Lymphoblastoid Cells," Nature Genetics, 33:422-425 (2003).
Christie, W.W. et al. "Mass Spectrometry of Lipids. I. Cyclopropane Fatty Acid Esters", Lipids, vol. 1, No. 3, pp. 176-182 (Jan. 1966).
Christner, C. Herdegen, et al., "FKBP Ligands as Novel Therapeutics for Neurological Disorders", Mini-Rev. Med. Chem. 1,337-397 (2001).
Chung, H. et al., "Protein Phosphatase 2A Suppresses MAP Kinase Signaling and Ectopic Protein Expression", Cell Signal. 11,575-580 (1999).
Clark et al. "Evidence that the Bradykinin-induced Activation of Phospholipase D and of the Mitogen-activated Protein Kinase Cascade Involve Different Protein Kinase C. Isoforms," J. Biol. Chem. 270:7097-7103, 1995.
Connolly, G.P., "Fibroblast Models of Neurological Disorders: Fluorescence Measurement Studies", Trends Pharmacol. Sci. 19, 171-177 (1998).
Cornforth et al., "Automated Classification Reveals Morphological Factors Associated with Dementia," Applied Computing, 8:182-190 (2008).
Cruzblanca et al., "Bradykinin Inhibits M Current via Phospholipase C and Ca2+ Release from IP3-sensitive Ca1 + Stores in Rat Sympathetic Neurons, " Proc. Natl. Acad. Sci. USA, 95:7151-7156 (Jun. 1998).
Cuenda et al., "Use of Kinase Inhibitors to Dissect Signaling Pathways," Methods in Molecular Biology, vol. 99, Humana Press Inc., Totowa, NJ (2000).
Cummings, J.L. et al., "Alzheimer's Disease: Etiologies, Pathophysiology, Cognitive Reserve, and Treatment Opportunities", Neurology 51, S2-S17 (1998).
De Leon et al., "Biomarkers for the early diagnosis of Alzheimer's disease," Neurology, 5 (Mar. 2006).
Dineley, Kit et al., "Beta-amyloid Activates the Mitogen-activated Protein Kinase Cascade via Hippocampal alpha7 Nicotinic Acetylcholine Receptors: in vitro and in vivo Mechanism is Related to Alzheimer's Disease", J. Neurosci. 21,4125-4133 (2001).
Du et al., "Protein Kinase C Activators Work in Synergy with Specific Growth Factors to Initiate Tyrosine Hydroxylase Expression in Striatal Neurons in Culture," J. Neurochem. 1997; 68:564-69.
Dunckley et al., Gene Expression Correlates of Neurofibrillary Tangles in Alzheimer's Disease, Neurobiol. Aging, 27(1):1359-1371 (2006).
Ekinci et al., "Hyperactivation of Mitogen-Activated Protein Kinase Increases Phosphyo-Tau Immunoreactivity Within Human Neuroblastoma: Additive and Synergistic Influence of Alteration of Additional Kinase Activities," Cell Mol. Neurobiol., 19(2):249-260 (1999).
El-Dahr et al., "Bradykinin Stimulates the ERKfwdanwElk-1fwdanwFos/AP-1 Pathway in Nesagial Cells," American Journal of Pyschology, 275(3 Part w):F343-F352 (Sep. 1998).
Enard et al., "Intra- and Interspecific Variation in Primate Gene Expression Patterns," Science, 296(5566):340-343 (2002).
English-language Translation for JP 6-279311 dated Jun. 2008.
English-language Translation for JP10-90263 dated Apr. 10, 1998.
Est Profile Hs.400740, available at www.ncbi.nlm.nih.gov/UniGene, printed on Aug. 3, 2012, pp. 1-3.
Etcheberrigaray et al., "Ionic and Signal Transduction Alterations in Alzheimer's Disease," Molecular Neurobiology, 20 (1999).
Etcheberrigaray et al., "Calcium Responses are Altered in Fibroblasts from Alzheimer's Patients and Pre-symptomatic PS1 Carriers; A Potential Tool for Early Diagnosis," Alzheimer's Reports, 3(5&6):305-312 (2000).
Etcheberrigaray et al., "Calcium Responses in Fibroblasts from Asymptomatic Members of Alzheimer's Disease Families," Neurobiol. of Disease., 5:37-45 (1998).
Etcheberrigaray et al., "Potassium Channel Dysfunction in Fibroblasts Identifies Patients with Alzheimer Disease," Proc. Natl. Acad. Sci. USA, 90:8209-8213 (Sep. 1993).

(56) References Cited

OTHER PUBLICATIONS

Etcheberrigaray et al., "Therapeutic effects of PKC activators in Alzheimer's disease transgenic mice", PNAS, 01(30):11141-11146 (2004).
Etcheberrigaray et al., "Molecular Mechanisms of Memory and the Pathophysiology of Alzheimer's Disease," Ann NY Acad Sci., 747:245-55 (1994).
European Search Report for EP 02 72 3236 dated Mar. 24, 2004.
Extended European Search Report in EP 13004274.0 dated Oct. 28, 2013.
Extended European Search Report issued on EP 08 02 0258 dated Jan. 30, 2009.
Extended European Search Report issued on EP 10 01 1288, dated Mar. 25, 2011.
Extended European Search Report issued on EP 10 01 1289 dated Mar. 23, 2011.
Extended European Search Report issued on EP 10 01 2836, dated Mar. 25, 2011.
Extended European Search Report issued on EP 10 011 290, dated Mar. 23, 2011.
Fan et al., "Arachidonic Acid and Related Methyl Ester Mediate Protein Kinase C Activation in Intact Platelets Through the Arachidonate Metabolism Pathways," Biochemical and Biophysical Research Comm., 169(3):933-940 (Jun. 29, 1990).
Favit et al., "Alzheimer's-specific effects of soluble (β-amyloid on protein kinase C- and—degradation in human fibroblasts", Cell Biology, 95:5562-5567 (1998).
Favit et al., "KC Isoenzymes are Differentially Affected by Low Concentrations of Soluble Beta-Amyloid Protein in Alzheimer's Disease," Society for Neuroscience Abstracts, 23(1-2):293 (1993).
Fernandez, J. et al., "Okadaic Acid, Useful Tool for Studying Cellular Processes", Curr. Med. Chem. 9, 229-262 (2002).
Ferrell Jr., J.E., "How Regulated Protein Translocation can Produce Switch-like Responses", Trends Biochem. Sc. 23,461-465 (1998).
Final Office Action mailed Sep. 13, 2011, in U.S. Appl. No. 11/660,868.
Final Office Action mailed Oct. 11, 2011, in U.S. Appl. No. 12/083,056.
Force, T. et al., "Growth Factors and Mitogen-activated Protein Kinases", Hypertension 31, 152-161 (1998).
Frey et al. "Problems Associated with Biological Markers of Alzheimer's Disease," Neurochemical Research, 30(12):1501-1510 (Dec. 2005).
Furukawa et al., "Formation of Human Fibroblast Aggregates (Spheroids) by Rotational Culture", Cell Transplantation, vol. 10, pp. 441-445 (2001).
Gasparini et al., "Stimulation of (β-Amyloid Precursor Trafficking by Insulin Reduces Intraneuronal (β-Amyloid and Requires Mitogen-Activated Protein Kinase Signaling," The Journal of Neuroscience, 21(8):2561-2570 (Apr. 15, 2001).
Gebreyesus et al., "Bradykinin Elevates Tyrosine Hydroxylase and Dopamine Beta-Hydroxylase mRNA levels in PC12 Cells," Brain Res., 608(2):345-348 (1993).
Gibson et al., "Calcium stores in cultured fibroblasts and their changes with Alzheimer's disease," Biochimica et Biophysica Acta, 1316:71-77 (1996).
Gillespie et al., "Secretory Processing of the Alzheimer Amyloid B/A4 Protein Precursor is Increased by Protein Phosphorylation," Biochemical and Biophysical Research Communications, 187(3):1285-1290 (1992).
Goedert, M. et al., "Tau Proteins of Alzheimer Paired Helical Filaments: Abnormal Phosphorylation of All Six Brain Isoforms", Neuron 8, 159-168 (1992).
Gold, B.G., "FK506 and the Role of the Immunophilin FKBP-52 in Nerve Regeneration", Drug Metab. Rev. 31,649-663 (1999).
Gong et al., "Phosphorylation of Microtubule-Associated Protein Tau is Regulated by Protein Phosphatase 2A in Mammalian Brain," Jour. of Biol. Chem., 275(8):5535-5544 (Feb. 25, 2000).

Gong, C.X. et al., "Phosphatase Activity Toward Abnormally Phosphorylated Tau; Decrease in Alzheimer Disease Brain", J. Neurochem. 65, 732-738 (1995).
Gonzales, EA et al., "Serum-induced Translocation of Mitogen-activated Protein Kinase to the Cell Surface Ruffling Membrane and the Nucleus", J. Cell Biol. 122, 1089-10101 (1993).
Govoni et al., "Cytosol Protein Kinase C Down regulation in Fibroblasts from Alzheimer's Disease Patients," Neurology, 43:2581-2586 (1993).
Grant et al., "Phosphorylation of Mitogen-Activated Protein Kinase is Altered in Neuroectoderman Cells Overexpressing the Human Amyloid Precursor Protein 751 Isoform," Molecular Brain Research., 72:115-120 (1999).
Greenberg et al., "Secreted Beta-amyloid Precursor Protein Stimulates Mitogen-activated Protein Kinase and Enhances Tau Phosphorylation," Proc Natl Acad Sci USA, 91:7104-7108 (1994).
Growdon et al., "Biomarkers of Alzheimer Disease", Arch Neurol., vol. 56, No. 3, pp. 281-283, 1999.
Guise, S. et al., "Hyperphosphorylation of Tau is Mediated by ERK Activation During Anticancer Drug-induced Apoptosis in Neuroblastoma Cells", J. Neurosci. Res. 63,257-267 (2001).
Harvey D.J., "Picolinyl Derivatives for the Characterization of Cyclopropane Fatty Acids by Mass Spectrometry", Biomedical Mass Spectrometry, Heyden & Son, London, GB, vol. 11, No. 4, pp. 187-192 (Apr. 1984).
Harvey, D.J., "Pyridine-containing derivatives for the structural elucidation of the alkyl chains of lipids by mass spectrometry and a comparison with the spectra of related heterocyclic derivatives," Spectroscopy Int. J., 8: 211-244 (1990).
Haug et al., "Decreased Inositol (1,4,5)-Trisphosphate Receptor Levels in Alzheimer's Disease Cerebral Cortex: Selectivity of Changes and Possible Correlation to Pathological Severity," Neurodegeneration, 5:169-176 (1996).
Heid, C.A. et al., "Real Time Quantitative PCR Genome" Res. 6, 986-994 (1996).
Hetman et al., "Role of Extracellular Signal Regulated Kinases 1 and 2 in Neuronal Survival," Eur. J. Biochem, 271:2050-2055 (2004).
Hirashima et al., "Calcium Responses in Human Fibroblasts: A Diagnostic Molecular Profile for Alzheimer's Disease," Neurology of Aging, 17(4):549-555 (1996).
Hogervorst et al., "The Validity and Reliability of 6 Sets of Clinical Criteria to Classify Alzheimer's Disease and Vascular Dementia in Cases confirmed Post-Mortem: Added Value of a Decision Tree Approach," Dement Geriatr Coqn Disord 2003:16:170-180.
Hongpaisan et al., "A structural basis for enhancement of long-term associative memory in single dendritic spines regulated by PKC", Proc. Natl. Acad. Sci .USA, vol. 104, No. 49, pp. 19571-19576, Dec. 4, 2007.
Hoshikawa et al., "Hypoxia Induces Different Genes in the Lungs of Rats Compared with Mice," Physiol Genomics, 12:209-219 (2003).
House et al., "Protein kinase C contains a pseudosubstrate prototope in its regulatory domain." Science, vol. 238, No. 4834, pp. 1726-1728, Dec. 1987.
Huang et al., "Increased Inositol 1,4, 5-Trisphosphate Accumulation Correlates With an Up-Regulation of Bradykinin Receptors in Alzheimer's Disease," Journal of Neurochemistry, 64(2):761-766 (Feb. 1995).
Huang et al., "Inositol Phosphates and Intracellular Calcium after Bradykinin Stimulation in Fibroblasts from Young, Normal Aged and Alzheimer Donors," Neurobiology of Aging, US, 12(5):469-473 (Sep. 1991).
Huang et al., "Involvement of Intermediary Metabolites in the Pathway of Extracellular Ca2+ Induced Mitogen-Activated Protein Kinase Activation in Human Fibroblasts," Cell. Signal, vol. 11, No. 4 pp. 263-274 (1999).
Hug et al., "Protein kinase C isoenzymes: divergence in signal transduction?" Biochem J. 1993;291:329.
Huynh et al., "Reduced Protein Kinase C Immunoreactivity and Altered Protein Phosphorylation in Alzheimer's Disease Fibroblasts," Arch Neurol 46 (1989).
Hyman et al.,, "Extracellular Signal-Regulated Kinase (MAP Kinase) Immunoreactivity in the Rhesus Monkey Brain." Neurosci. Lett., 166:113-116 (1994).

(56) References Cited

OTHER PUBLICATIONS

International Preliminary Report on Patentability and Written Opinion for PCT/2005/036014 dated Apr. 24, 2008.
International Preliminary Report on Patentability and Written Opinion for PCT/2006/022156 dated Apr. 24, 2008.
International Preliminary Report on Patentability and Written Opinion for PCT/US2006/037186 dated Apr. 16, 2008.
International Search Report and Written Opinion for PCT/US2006/037186 dated Apr. 11, 2007.
International Search Report and Written Opinion for PCT/US2009/051927 dated Jan. 18, 2010.
International Search Report and Written Opinion for PCT/US2012/064783 dated Mar. 6, 2013.
International Search Report and Written Opinion issued in PCT/US2010/051112 on May 9, 2011.
International Search Report and Written Opinion issued in PCT/US2010/051236 on Mar. 2, 2011.
International Search Report and Written Opinion on PCT/US2005/036014 dated Oct. 19, 2006.
International Search Report and Written Opinion on PCT/US2006/022156 dated Feb. 8, 2007.
International Search Report for PCT/US2004/38160 dated Nov. 4, 2005.
International Search Report for PCT/US2009/051931 dated Nov. 4, 2009.
International Search Report issued on PCT/US2005/036014, published Apr. 19, 2007 (11 pages total).
International Search Report issued on PCT/US2006/022156, published Apr. 19, 2007, 6 pages.
International Search Report issued on PCT/US2009/002120, dated Sep. 25, 2009.
Irizarry et al., "Biomarkers of Alzheimer Disease in Plasma," The Journal of the American Society for Experimental NeuroTherapeutics, 1:226-234 (Apr. 2004).
Ito et al., "Internal Ca2+ Mobilization is Altered in Fibroblasts from Patients with Alzheimer Disease." Proc Natl Acad Sci USA, 91:534-538 (1994).
Janessens, V. et al., "Protein Phosphatase 2A: A Highly Regulated Family or Serine/threonine Phosphates Implicated in Cell Growth and Signaling", Biochem. J. 353,417-439 (2001).
Janssens, V. et al., "Identification and Functional Analysis of Two Ca2+-Binding EF Hand Motifs in the B"/PR72 Subunit of Protein Phosphatase 2A 1", Biol. Chem. 278, 10696-10706 (2003).
Jellinger, KA. et al., "Neuropathology of Alzheimer's Disease: a Critical Update", J. Neural Transm. Suppl. 54;77-95 (1998).
Jin et al., "Changes in Protein Kinases in Brain Aging and Alzheimer's Disease," Drugs & Aging, 6(2):136-149 (1995).
Johnson et al., "IQGAP1 regulation and roles in cancer", Cellular Signaling, vol. 21, pp. 1471-1478 (2009).
Kang et al., Nature, 1987;325:733-736.
Kanno et al., "The Linoleic Acid Derivative DCP-LA Selectively Activates PKC-ε, Possibly Binding to the Phosphatidylserine Binding Site," Journal of Lipid Research, 47:1146-56 (2006).
Kanno et al., "The Newly Synthesized Linoleic Acid Derivative DCP-LA Selectively Activates PKC-ε", Dept. of Physiology, Hyogo College of Med., Hyogo, Japan, p. 552 (2006).
Katzman, "Alzheimer's disease." New England.J. Medicine. 1986;314:964-973.
Khan et al., "A Cellular Model of Alzheimer's Disease Therapeutic Efficacy: PKC Activation Reverses A Beta-Induced Biomarker Abnormality on Cultured Fibroblasts," Neurobiology of Disease, 34(2): 332-339, vol. 34, No. 2 (May 2009).
Khan et al., "An Internally Controlled Peripheral Biomarker for Alzheimer's Disease: Erk1 and Erk2 responses to the Inflammatory Signal Bradykinin," PNAS, vol. 103, No. 35, pp. 13203-13207, Aug. 29, 2006.
Kikkawa et al., "The Protein Kinase C Family: Heterogeneity and its Implications." Ann. Rev. Biochem, vol. 58, pp. 31-44, 1989.

Kilpatrick et al., "Regulation of TNF Mediated Antiapoptoptic Signaling in Human Neutrophils: Role of -PKC and ERK1/2," Journal of Leukocyte Biology, 80:1512-1521 (Dec. 2006).
Kins, S. et al., "Reduced Protein Phosphatase 2A Activity Induces Hyperphosphorylation and Altered Compartmentalization of Tau in Transgenic Mice", J. Biol. Chem. 276, 3819338200 (2001).
Kitaguchi et al., "Novel precursor of Alzheimer's disease amyloid protein shows protease inhibitory activity," Nature, 1988; 331:530-532.
Kleinman et al., "Use of extracellular matrix components for cell culture", Analytical Biochemistry, 166, pp. 1-13, (1987).
Klettner, A. et al., "The Neuroprotective Actions of FK506 Binding Protein Ligands: Neuronal Survival is Triggered by de novo RNA Synthesis, but is Independent of Inhibition of NJK and Calcineurin", Brain Res. Mol. Brain Res. 97, 21-31 (2001).
Knowles, R.B. et al., "Demonstration by Fluorescence Resonance Energy Transfer of a Close Association Between Activated Map Kinase and Neurofibrillary Tangles: Implications for MAP Kinase Activation in Alzheimer Disease", J. Neuropathoi. Exp. Neurol. 58,1090-1098 (1999).
Kohkhlatchev, AV. et al., "Phosphorylation of the MAP Kinase ERK2 Promotes its Homodimerization and Nuclear Translocation", Cell 93, 605-615 (1998).
Kurumatani et al., "Loss of Inositol 1,4,5-trisphosphate Receptor Sites and Decreased PKC Levels Correlate with Staging of Alzheimer's Disease Neurofibrillary Pathology," Brain Research, 796:209-221 (1998).
Kuzirian et al., "Bryostatin Enhancement of Memory in Hermissenda", Biol. Bull. 210:201-214 (Jun. 2006).
L'Allemain, "Deciphering the Map Kinase Pathway," Progress in Growth Factor Research, 5(3):291-334 (Jan. 1, 1994).
Lallenend et al., "Activation of protein kinase CβI constitutes new neurotrophic pathway for deafferented spiral ganglion neurons," J. Cell Sci. 2005;118:4511-25.
Laporte et al., "Role of ERK MAP Kinases in Responses of Cultured Human Airway Smooth Muscles Cells to IL-1B." Am. J. Physiol. Lung Cell Mol. Physiol., 277:943-951 (1999).
Laurent-Matha et al., "Catalytically inactive human cathepsin D triggers fibroblast invasive growth", J. Cell Biology, vol. 168, No. 3, pp. 489-499, Jan. 31, 2005.
Lee, V.M., "Disruption of the Cytoskeleton in Alzheimer's Disease", Curr. Opin. Neurobio. 5,663-668 (1995).
Leissring et al., "Capacitative Calcium Entry Deficits and Elevated Luminal Calcium Content in Mutant Presenilin-1 Knockin Mice," J. Cell Biology, 149 (2000).
Leissring et al., "Presenilin-2 Mutations Modulate Amplitude and Kinetics of Inositol 1,4,5-Trisphosphate-mediated Calcium Signals," The Journal of Biological Chemistry, 274(46):32535-32538 (Nov. 12, 1999).
Lenormand, P. et al., "Growth Factors Induce Nuclear Translocation of MAP Kinase (p42mapk and /44mapk) But Not of Their Activator MAP Kinase (p45mapkk) in Fibroblasts", J. Cell Biol. 122, 1079-1088 (1993).
Lewis, T.S. et al., "Signal Transduction Through MAP Kinase Cascades", Adv. Cancer Res. 74,49-139 (1998).
Liang et al., "Altered Neuronal Gene Expression in Brain Regions Differentially affected by Alzheimer's Disease: A reference Data Chart," Physiol Genomics, 33:240-256 (2008).
Liebmann, C., "Bradykinin Signaling to MAP Kinase: Cell Specific Connections Versus Principle Mitogenic Pathways", Biol. Chem. 382, 49-55 (2001).
Liu et al., "Protein Phosphatase 2A in Alzheimer's Disease," Pathophysiology 16:273-277 (2009).
Liu et al., "The seven-fold way of PKC regulation," Cell. Signal., 10(8):529-42 (1998).
Livak, KJ. et al., "Analysis of Relative Gene Expression Data Using Realtime Quantitative PCR and the 2-AAC T Method", Methods. 25, 402-408 (2001).
Loring et al., "A Gene Expression Profile of Alzheimer's Disease," DNA and Cell Biology, 20(11):683-695 (2001).
Lu et al., P44mpk MAP Kinase Induces Alzheimer Type Alterations in Tau Function and in Primary Hippocampal Neurons, J. Neurosci. Res., 35:439-444 (1993).

(56) References Cited

OTHER PUBLICATIONS

Luigi et al., "Inflammatory Markers in Alzheimer's Disease and Multi-Infarct Dementia," Mechanisms of Ageing and Development, 122:1985-1995 (2001).
Mandelkow, E. et al. "On the Structure of Microtubules, Tau, and Paired Helical Filaments", Neurobiol. Aging 16, 347-354 (1995).
Masliah et al., "Differential Involvement of Protein Kinase C Isozymes in Alzheimer's Disease," The Journal of Neuroscience, 10:7, 2113-2124, Jul. 1990.
Masliah, "Protein Kinase C Alteration is an Early Biochemical Marker in Alzheimer's Disease," The Journal of Neuroscience, 11(9): 2759-2767 (1991).
Matsubayash, Y. et al., "Evidence for Existence of a Nuclear Pore Complex-mediated, Cytosol-independent Pathway of Nuclear Translocation of ERK MAP Kinase in Permeabilized Cells", J. Biol. Chem. 276, 41755-41760 (2001).
Mattson et al., "Presenilin-1 Mutation Increases Neuronal Vulnerability to Focal Ischemia In Vivo and to Hypoxia and Glucose Deprivation in Cell Culture: Involvement of Perturbed Calcium Homeostatis," J. Neurosci, 20(4):1358-1364 (Feb. 15, 2000).
Mattson, M. et al., "Presenilin Mutations and Calcium Signaling Defects in the Nervous and Immune Systems", BioEssays 23(8): 733-744 (2001).
McCoy et al., "Serum-and bradykinin-induced calcium transients in familial Alzheimer's fibroblasts," Neurobiology of Aging, 14(5):447-455 (Sep.-Oct. 1993).
McDonald et al., "β-Amyloid Fibrils Activate Parallel Mitogen-Activated Protein Kinase Pathways in Microglia and THP1 Monocytes," J Neurosci, 18:4451-4460 (1998).
McMahon, KA. et al., "Colony-stimulating Factor-I (CSF-I) Receptor-mediated Macrophase Differentiation in Myeloid Cells: A Role for Tyrosine 559-dependent Protein Phosphatase 2A (PP2A) Activity", Biochem. J. 358,431-436 (2001).
Michiels et al., "Prediction of Cancer Outcome with Microarrays: A multiple Random Validation Strategy," Lancet, 265:488-492 (2005).
Nagao, M. et al., "Protein Serine/threonine Phosphatase as Binding Proteins for Okadaic Acid", Mutat. Res. 333,173-179 (1995).
Nagasaka et al., "A Unique Gene Expression Signature Discriminates Familial Alzheimer's Disease Mutation Carriers from their Wild-type Siblings,", Proc. Natl. Acad. Sci., 102(41):14854-14859 (2005).
Nagata et al., "FR236924, a Newly Synthesized Derivative of Linoleic Acid, Ameliorates Memory Deficits in Rats Intraventricularly Injected with Amyloid-Beta Peptide." Jpn. J. Physiol. 53, Suppl. 2003(319): S261.
Nagata et al., "The Newly Synthesized Linoleic Acid Derivative DCP-LA Ameliorates Memory Deficits in Animal Models Treated with Amyloid-β Peptide and Scopolamine", Psychogeriatrics, 5:22-126 (2003).
Neve et al., "Alzheimer's Disease: Dysfunction of a Signaling Pathway Mediated by the Amyloid Precursor Protein?" Biochem. Soc. Symp. 67:37-50, (No Year Provided).
Ning et al., "Early Response Gene Signaling in Bryostatin-Stimulated Primary B Chronic Lymphocytic Leukemia Cells in Vitro," Biochemical J., 319(1):59-65 (1996).
NME Digest, "DrugLine," Drug News Perspect, 2002, pp. 666-674, vol. 15, No. 10.
Oddo et al., "Temporal Profile of Amyloid-β (AB) Oligomerization in an in Vivo Model of Alzheimer Disease—A Link Between AB and TAU Pathology," Journal of Biological Chemistry, 281(3):1599-1604 (Jan. 20, 2006).
Office Action (final) mailed Oct. 17, 2013, in U.S. Appl. No. 12/729,042.
Office Action (Restriction Requirement) mailed Aug. 16, 2011, in U.S. Appl. No. 12/510,707.
Office Action (Restriction Requirement) mailed Dec. 2, 2010, in U.S. Appl. No. 12/083,056.
Office Action (Restriction Requirement) mailed May 23, 2011, in U.S. Appl. No. 12/510,681.
Office Action (Restriction Requirement) mailed Oct. 27, 2010, in U.S. Appl. No. 12/729,042.
Office Action mailed Aug. 24, 2012, in U.S. Appl. No. 12/083,056.
Office Action mailed Dec. 12, 2010, in U.S. Appl. No. 11/660,868.
Office Action mailed Jan. 2, 2014, in U.S. Appl. No. 12/729,042.
Office Action mailed Mar. 25, 2014, in U.S. Appl. No. 12/895,957.
Office Action mailed Oct. 11, 2012, in U.S. Appl. No. 12/896,862.
Office Action mailed Sep. 20, 2012, in U.S. Appl. No. 12/729,042.
Office Action (Final) mailed Jun. 13, 2014 in U.S. Appl. No. 13/401,459.
Office Action (non-final) mailed Nov. 5, 2014, in co-pending U.S. Appl. No. 12/895,957.
Office Action (Requirement for Restriction) mailed Aug. 12, 2010, in U.S. Appl. No. 11/660,868.
Office Action mailed Apr. 29, 2011, in U.S. Appl. No. 12/083,056.
Office Action mailed Aug. 17, 2012, in U.S. Appl. No. 11/660,868.
Office Action mailed Aug. 2, 2013, U.S. Appl. No. 12/510,707.
Office Action mailed Jul. 31, 2013, in U.S. Appl. No. 13/401,459.
Office Action mailed Jun. 7, 2011, in U.S. Appl. No. 12/729,042.
Office Action mailed Nov. 15, 2012, in U.S. Appl. No. 12/510,707.
Office Action mailed Nov. 18, 2013, in U.S. Appl. No. 12/895,957.
Ohta et al., "Stearic Acid Facilities Hippocampal Neurotransmission by Enhancing Micotinic Ach Receptor Responses via an PKC Pathway," Molecular Brain Research, 119:83-89 (Aug. 27, 2003).
Pascale et al., "Enhanced BK-Induced Calcium Responsiveness in PC12 Cells Expressing the C100 Fragment of the Amyloid Precursor Protein," Brain Res Mol Brain Res, 72:205-2 (1999).
Pasinetti GM., "Use of cDNA Microarray in the Search for Molecular Markers Involved in the Onset of Alzheimer's Disease Dementia", J Neurosci Res., 65(6):471-476, Aug. 31, 2001.
Pei et al., "Expression of Protein Phosphatases (PP-1, PP-2A, PP-2B, and PTP-1B) and Protein Kinases (MAP kinase and P34cdc2) in the Hippocampus of Patients with Alzheimer Disease and Normal Aged Individuals," Brain Research, 665(1-2):70-76 (Aug. 29, 1994).
Planel, E. et al., "Inhibition of Protein Phosphatase 2A Overrides Tau Protein Kinase I/glycogen Synthase Kinase 3β and Cyelin Dependent Kinase 5 inhibition and Results in Tau Hyperphosphorylation in the Hippocampus of Starved Mouse", J. Biol. Chem. 276, 34289-34306 (2001).
Ponte et al., "A new A4 amyloid mRNA contains a domain homologous to serine proteinase inhibitors," Nature, 1988;331:525-527.
Pub Chem Compound, XP002550143 (May 27, 2005).
Putney, Jr., "Presenilins, Alzheimer's Disease, and Capacitative Calcium Entry," Neuro, 27:411-412 (2000).
Racchi et al., "Bradykinin-induced amyloid precursor protein secretion: a protein kinase C-independent mechanism that is not altered in fibroblasts from patients with sporadic Alzheimer's disease", Biochem J., vol. 330, pp. 1271-1275, 1998.
Ragaglia et al., "PP2A mRNA Expression is Quantitatively Decreased in Alzheimer's Disease Hippocampus", Experimental Neurology, 168, 402-412 (2001).
Rametti et al., "Linking Alterations in Tau Phosphorylation and Cleavage during Neuronal Apoptosis*," The Journal of Biological Chemistry, 279(52):54518-54528 (2004).
Rapoport et al., "PD98059 Prevents Neurite Degeneration Induced by Fibrillar B-Amyloid in Mature Hippocampal Neurons", J. Neurochem., vol. 74, pp. 125-133, 2000.
Remarque et al., "Patients with Alzheimer's Disease Display a Pro-inflammatory Phenotype," Experimental Gerontology, 36:171-176 (2001).
Reynolds et al., "Phosphorylation Sites on Tau Identified by Nanoelectrospray Mass Spectrometry:Differences In Vitro Between the Mitogen-Activated Protein Kinase ERK2, c-Jun N-Terminal Kinase and P38, and Glycogen Synthase Kinase-3B," J. Neurochem., 74:1587-1595 (2000).
Roovers, K. et al., "Integrating the MAP Kinase Signal into the G1 Phase Cell Cycle Machinery", Bioessays 22, 818-826 (2000).
Roux et al., "ERK and p38 MAPK-Activated Protein Kinases: a Family of Protein Kinase with Diverse Biological Functions," Microbiology and Molecular Biology Reviews, 68(2):320-344 (Jun. 2004).
Saito, T. et al., "In Situ Dephosphorylation of Tau by Protein Phosphatase 2A and 2B in Fetal Rat Primary Cultured Neurons", FEBS Lett. 376,238-242 (1995).

(56) References Cited

OTHER PUBLICATIONS

Sato et al., "Elevated Amyloid Beta Protein (1-40) Level Induces CREB Phosphorylation at Serine-133 via p44/42 MAP kinase (Erk1/2)-dependent pathway in rat pheochromocytoma PC12 cells," Biochemical and Biophysical Research Communications, 232(3):637-642(Mar. 27, 1997).
Shaw et al., "Biomakers of neurodegeneration for diagnosis and monitoring therapeutics", Natures Review Drug Discovery, vol. 6, pp. 295-303 (2007).
Sheehan et al., "Calcium Homeostasis and Reactive Oxygen Species Production in Cells Transformed by Mitochondria from Individuals with Sporadic Alzheimer's Disease," The Journal of Neuroscience, 17(12):4612-4622 (Jun. 15, 1997).
Sheppeck, J.E. et al., "Inhibition of the Ser-Thr Phosphatases PPI and PP2A by Naturally Occurring Toxins", Bioorg. Med. Chem. 5, 1739-1750 (1997).
Silverstein, A.M. et al., "Actions of PP2A on the MAP Kinase Pathway and Apoptosis are Mediated by Distinct Regulatory Subunits", Proc. Natl. Acad. Sci. USA 99,4421-4426 (2002).
Solerte et al., "Hemorheological Changes and Overproduction of Cytokines from Immune Cells in Mild to Moderate Dementia of the Alzheimer's Type: Adverse Effects on Cerebromicrovascular System," Neurobiology of Aging, 21( 2):271-287 (2000).
Sun et al., "Poststroke neuronal rescue and synaptogenesis mediated in vivo by protein kinase C in adult brains", Proc. Natl. Acad. Sci. USA, Sep. 9, 2008; vol. 105, No. 36, pp. 13620-13625.
Sun et al., "Dual Effects of Bryostatin-1 on Spatial Memory and Depression", Eur. J. Pharmacol., vol. 512, pp. 43-51, 2005.
Sweatt, J.D., "The Neuronal MAP Kinase Cascade: a Biochemical Signal Integration System Subserving Synaptic Plasticity and Memory", J. Neurochem. 76,1-10 (2001).
Tanaka et al., "The Newly Synthesized Linoleic Acid Derivative FR236924 Induces a Long-Lasting Facilitation of 4 Hippocampal Neurotransmission by Targeting Nicotinic Acetylcholine Receptors", Bioorganic & Medicinal Chem. Letters, 13:1037-1040 (2003).
Tanzi et al., "The Gene Defects Responsible for Familial Alzheimer's Disease," Neurobiology of Disease, 3:159-168 (1996).
Tanzi et al., "Protease Inhibitor domain encoded by an amyloid protein precursor mRNA associated with Alzheimer's disease," Nature, 1988; 331:528-530.
Tesco et al., "Growth properties of familial Alzheimer skin fibroblasts during in vitro aging", Exp Gerontology, 28(1):51-8, 1993.
Thal et al., "The Role of Biomarkers in Clinical Trials for Alzheimer Disease," Alzheimer Dis Assoc Disord, 20(1) Jan.-Mar. 2006.
Treisman, R, "Regulation of Transcription by MAP Kinase Cascades", Curr. Opin. Cell Biol. 8, 205-215 (1996).
Urbanelli et al., "Cathepsin D expression is decreased in Alzheimer's disease fibroblasts", Neurobiology of Aging, vol. 29, pp. 12-22 (2008).
Valijent, E. et al., "Mitogen-activated Protein Kinase/extracellular Signal-regulated Kinase Induced Gene Regulation in Brain: A Molecular Substrate for Learning and Memory", Mol. Neurobiol. 23, 83:99 (2001).
Vogelsberg-Ragaglia et al., "PP2AmRNA Expression is Quantitatively Decreased in Alzheimer's Disease Hippocampus1," Experimental Neurology, 168:402-412 (2001).
Volmat, V. et al., "The Nucleus, a Site for Signal Termination by Sequestration and Inactivation of p42/p44 MAP Kinases", J. Cell Sci. 114,3433-3443 (2001).
Wallace, "Effects of Alzheimer's Disease-related β amyloid protein fragments on enzymes metabolizing phosphoinositides in brain," Biochem Biophys Acta., 1227:183-187 (1994).
Wang, J.Z. et al., "Dephosphorylation of Alzheimer Paired Helical Filaments by Protein Phosphatase-2A and -2B", J. Biol. Chem. 270, 4854-4860 (1995).
Weeraratna et al., "Alterations in immunological and neurological gene expression patterns in Alzheimer's disease tissues", vol. 313, pp. 450-461 (2007).
Weinreb et al., "Neuroprotection via pro-survival protein kinase C isoforms associated with Bcl-2 family members," The FASEB Journal 2004; 118:1471-1473.
Winer, J. et al., "Development and Validation of Real-time Quantitative Reverse Transcriptase-polymerase Chain Reaction for Monitoring Gene Expression in Cardiac Myocytes in vitro", Anal. Biochem. 270, 41-49 (1999).
Winter, C. et al., "MAP Kinase Phosphatase 1 is Expressed and Enhanced by FK506 in Surviving Mamillary, but not Degenerating Nigral Neurons Following Anatomy", Brain Res. 801, 198-205 (1998).
Yaguchi et al., "Effects of Cis-unsaturated Free Fatty Acids on PKC-ε Activation and Nicotinic ACh Receptor Responses", Molecular Brain Res., 133:320-324 (2005).
Yaguchi et al., "Linoleic Acid Derivative DCP-LA Improves Learning Impairment in SAMP8", Neuropharmacology and Neurotoxicology, 17(1):105-108 (Jan. 23, 2006).
Yaguchi et al., "The CIS-Unsaturated Free Fatty Acid Derivative HEPBA Regulates α7 Nicotinic ACh receptor Trafficing", Dept. αf Physiology, Hyogo College of Med., Hyogo, Japan, Bulletin of the Japanese Society for Neurochemistry, 2008, 47(2/3): 222.
Yamamoto et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, 130:207-213 (2005).
Yang et al., "Bradykinin-Induced p42/p44 MAPK Phosphorylation and Cell Proliferation via Src, EGF Receptors and P13-K/Akt in Vascular Smooth Muscle Cells," Journal of Cellular Physiology, 203:538-546 (2005).
Yoo et al., "Presenilin-Mediated Modulation of Capacitative Calcium Entry," Neuron, 27:561-572 (Sep. 2000).
Youdim et al., "Molecular Basis of Neuroprotective Activities of Rasagiline and the Anti-Alzheimer Drug TV3326 [(N-Propargyl-(3R)Aminoindan-5-YL)-Ethyl Methyl Carbamate]," Cellular and Molecular Neurobiology, 21(6): 555-573 (Dec. 2001).
Young, et al., "Decreased Brain [3H]inositol 1 ,4,5-trisphosphate Binding in Alzheimer's Disease," Neuroscience Letters, 94:198-202 (2000).
Zawadzka, M. et al., "Immunosuppressant FK506 Affects Multiple Signaling Pathways and Modulates Gene Expression in Astrocytes", Mol. Cell. Neurosci.22,202-209 (2003).
Zhang et al., "Oxidative Stress Differentially Modulates Phosphorylation of ERK, p38 and CREB Induced by NGF or EGF in PC12 Cells." Neurobiology of Aging, 20:271-278 (1999).
Zhao et al., "Brain Insulin Receptors and Spatial Memory—Correlated Changes in Gene Expression, Tyrosine Phosphorylation, and Signaling Molecules in the Hippocampus of Water Maze Trained Rats," The Journal of Biological Chemistry, 274(49):34893-34902 (1999).
Zhao et al., "Dysfunction of MAP Kinase signaling in Alzheimer's Disease," Society of Neuroscience, Abstracts 25, 31st Annual Meeting of the Society of Neuroscience, San Diego, CA, USA, 27(1):924, (Nov. 10-15, 2001).
Zhao et al., "Impairment of Phosphatase 2A Contributes to the Prolonged MAP Kinase Phosphorylation in Alzheimer's Disease Fibroblasts," Neurobiology of Disease, 14(3):458-469 (Dec. 2003).
Zhao et al., "MAP Kinase Signaling Cascade Dysfunction Specific to Alzheimer's Disease in Fibroblasts," Neurobiology of Disease, 11(1):166-183 (Oct. 2002).
Zhu et al., "The role of mitogen-activated protein kinase pathways in Alzheimer's disease," Neurosignals, 11(5):270-281, Sep. 2002.

\* cited by examiner

SH-SY5Y CELLS TREATED WITH
DIFFERENT Aβ SPECIES FOR 20 HR

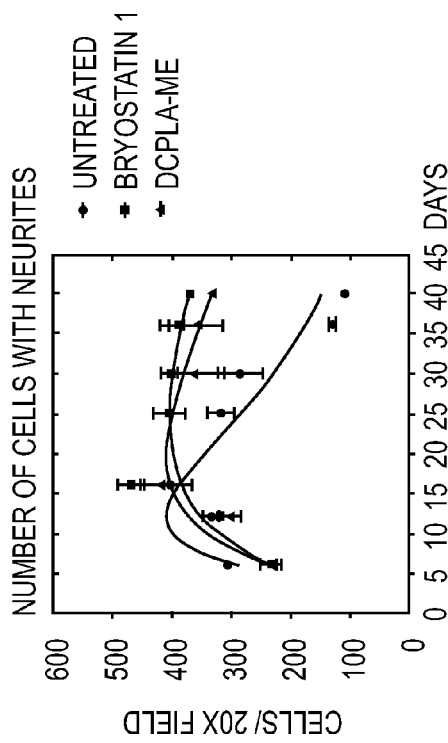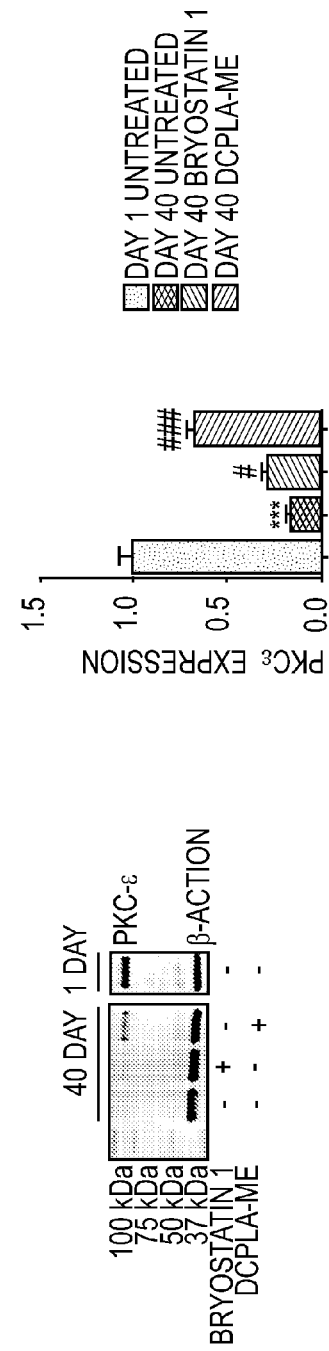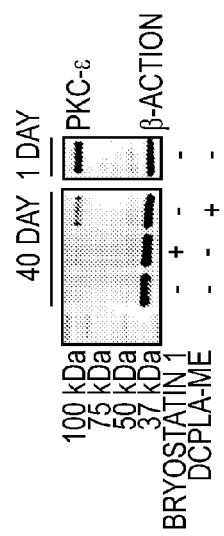
FIG. 16A
FIG. 16B
FIG. 16C
FIG. 16D

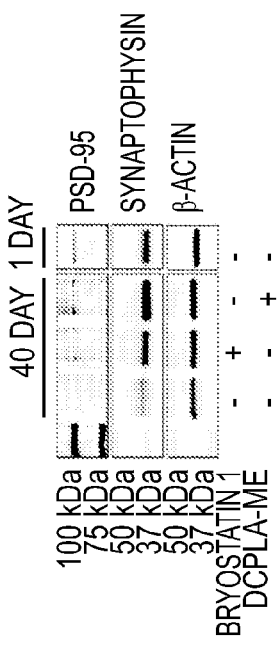
FIG. 16E
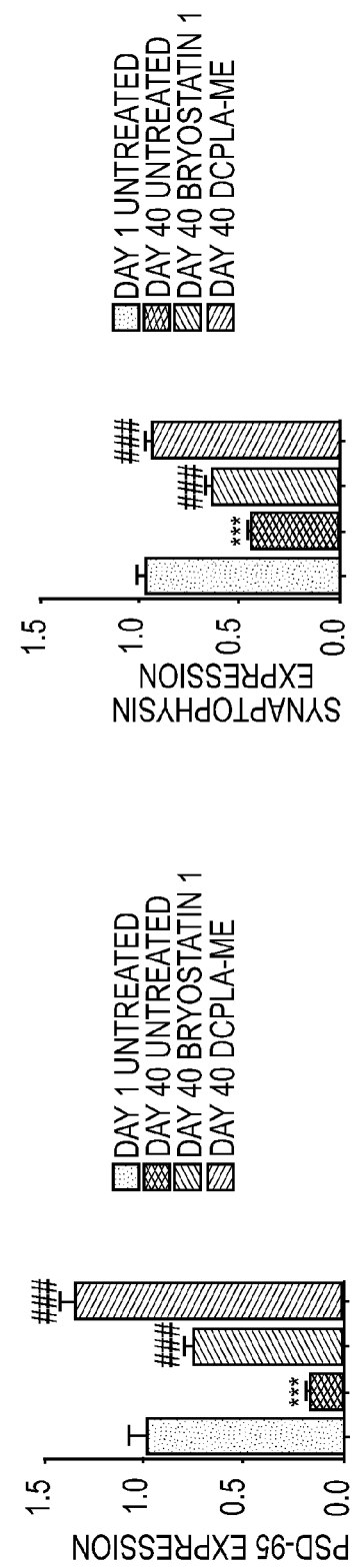
FIG. 16G
FIG. 16F

ESTERS OF DCPLA AND METHODS OF TREATMENT USING THE SAME

This application claims priority to U.S. Provisional Patent Application No. 61/559,117, filed Nov. 13, 2011, the contents of which are incorporated herein by reference.

FIELD OF THE DISCLOSURE

The present disclosure relates to esters of 8-[2-(2-pentyl-cyclopropylmethyl)cyclopropyl]-octanoic acid ("DCPLA"). The disclosure further relates to compositions, kits, and methods for treatment using the esters.

BACKGROUND OF THE DISCLOSURE

Protein kinase C is one of the largest families of protein kinase enzymes and is composed of a variety of isoforms. Conventional isoforms include α, βI, βII, γ; novel isoforms include δ, ε, η, θ; and atypical isoforms include ξ, and ι/λ.

PKC enzymes are primarily cytosolic but translocate to the membrane when activated. Once activated and translocated, PKC is anchored into the membrane by the anchoring protein RACK1. See, e.g., Mochly-Rosen et al. (1991) *Proc Natl Aced Sci USA* 88, 3997-4000; Nishizuka, Y. (1995) *FASEB J* 9, 484-496; Sklan et al. (2006) *Prog Neurobiol* 78, 117-134. RACK1 localizes PKC to its corresponding substrates for phosphorylation, thus making PKC functionally active and physiologically relevant.

Activated PKC participates in a variety of biological pathways. For example, PKC activates ELAV mRNA-stabilizing proteins and cAMP-response-element-binding ("CREB") proteins. PKC isoforms also play a regulatory role in amyloid precursor protein ("APP") processing and amyloid accumulation. For example, PKC-α and PKC-ε regulate APP processing by the non-amyloidogenic pathway, suggesting that decreases in these enzymes may lead to increases in A-beta synthesis and accumulation. Thus, PKC activators may be able to reduce levels of soluble A-beta and increase levels of soluble APP-α. PKC activators may also be able to reduce or eliminate amyloid plaques and neurofibrillary tangles.

PKC activators have been associated with prevention and treatment of various diseases and conditions. For example, PKC activators may allow for prevention and treatment of neurodegenerative diseases and conditions, neuroaffective diseases and disorders, cognitive impairments, and diseases and conditions associated with neuronal or synaptic loss. Indeed, PKC activators have been found to induce synapse formation. Moreover, PKC activators have been associated with improvement in, for example, memory and learning, including long-term memory.

In one example, PKC activators have demonstrated neuroprotective activity in animal models of Alzheimer's Disease ("AD"). See Etcheberrigaray et al., *Proc. Nat. Acad. Sci. USA*, 1992, 89: 7184-7188. AD is a neurodegenerative disorder that is characterized clinically by progressive decline of memory, cognition, reasoning, judgment, and emotional stability that gradually leads to profound mental deterioration and ultimately, death.

Pathologically, AD is associated with the accumulation of aggregated β-amyloid ("Aβ"), a 4 kDa peptide produced by the proteolytic cleavage of amyloid precursor protein ("APP") by β- and γ-secretases. Oligomers of Aβ are considered to be most toxic, while fibrillar Aβ is largely inert. Monomeric Aβ is found in normal patients and has an as-yet undetermined function.

PKC activators can reduce the levels of Aβ and prolong survival of AD transgenic mice. See Etcheberrigaray et al., 1992, *Proc. Nat. Acad. Sci. USA*, 89: 7184-7188. PKC-ε has been shown to be most effective at suppressing Aβ production. See Zhu et al., *Biochem. Biophys. Res. Commun.*, 2001, 285: 997-1006. Accordingly, isoform-specific PKC activators are highly desirable as potential anti-AD drugs.

The earliest consistent cytopathological change in AD is loss of synapses. See Scheff et al., *Neurobiol. Aging*, 2006, 27: 1372-1384; and Marcello et al., *Eur. J. Pharmacol.* 2008, 585: 109-118. In fact, synaptic loss appears to be the only pathological finding in the brain that is closely correlated with the degree of dementia in AD patients. See Terry et al., *Ann. Neurol.*, 1991, 30: 572-580. Evidence suggests that Aβ is involved in synaptic loss.

Other diseases and conditions are associated with synaptic loss and/or Aβ. Persons who have suffered from a brain injury, for example, show increased synthesis and expression of APP and its proteolytic product Aβ. See, e.g., Zohar et al., *Neurobiology of Disease*, 2011, 41: 329-337; Roberts et al., *Lancet*, 1991, 1422-1423; Gentleman e al., *NeuroReport*, 1997, 8: 1519-1522; Iwata et al., *J. Neuropathol. Exp. Neurol.*, 2002, 61: 1056-1068. In animal models, the PKC activator Bryostatin 1 was shown to protect against traumatic brain injury-induced learning and memory deficits. See Zohar et al., *Neurobiology of Disease*, 2011, 41: 329-337.

Additionally, some forms of stroke are caused by Aβ, such as those associated with cerebral amyloid angiopathy ("CAA"). See U.S. Patent Application Publication No. 2010/0022645 A1. This disorder is a form of angiopathy in which the same Aβ deposits as found in AD accumulate in the walls of the leptomeninges and superficial cerebral cortical blood vessels of the brain. Amyloid deposition predisposes these blood vessel to failure, increasing the risk of a hemorrhagic stroke. CAA is also associated with transient ischemic attacks, subarachnoid hemorrhage, Down's syndrome, post irradiation necrosis, multiple sclerosis, leucoencephalopathy, spongiform encephalopathy, and dementia pugilistica.

Both PKC-α and PKC-ε are important for synaptogenesis—i.e., the formation of synapses. The high abundance of PKC-ε in presynaptic nerve fibers suggests a role in neurite outgrowth, synaptic formation, and neurotransmitter release. See Shirai et al., *FEBS*, 2008, 29: 1445-1453. Nontoxic drugs activating PKC-α and PKC-ε can promote synaptogenesis under non-pathological conditions and actually prevent synaptic loss under pathological conditions. See Nelson et al., *Trends Biochem. Sci.*, 2009, 34: 136-145; Hongpaisan et al., *Proc. Natl. Acad. Sci. USA*, 2007, 104: 19571-19576; Sun et al., *Proc. Natl. Acad. Sci. USA*, 2008, 105: 13620-13625; Sun et al., *Proc. Natl. Acad. Sci. USA*, 2009, 106: 14676-14680.

For example, PKC activators have demonstrated neuroprotective activity in animal models of stroke. See Sun et al., *Eur. J. Pharmacol.*, 2005, 512: 43-51. Several PKC isoforms play a central role in mediating ischemic and reperfusion damage following stroke. Studies with experimental stroke models, mouse genetics, and selective peptide inhibitors and activators have demonstrated that PKC-ε is involved in induction of ischemic tolerance and prevents damage, while PKC-δ and PKC-γ are implicated in injury. See Takayoshi et al., *Stroke*, 2007, 38(2): 375-380; and Bright et al., *Stroke*, 2005; 36: 2781. Postischemic/hypoxic treatment with Bryostatin 1 effectively rescued ischemia-induced deficits in synaptogenesis, neurotrophic activity, and spatial learning and memory. See Sun et al., *Proc. Natl. Acad. Sci. USA.*, 2008, 105(36): 13620-13625

PKC activation has a crucial role in learning and memory enhancement and PKC activators have been shown to increase memory and learning. See Sun et al., *Eur. J. Pharmacol.* 2005, 512: 43-51; Alkon et al., *Proc. Natl. Acad. Sci. USA.*, 2005, 102: 16432-16437. For example, Bryostatin increased the rate of learning in rodents, rabbits, and invertebrates. See Sun et al., *Eur. J. Pharmacol.*, 2005, 512: 43-51; Wang et al., *Behav. Pharmacol.*, 2008, 19: 245-256; and Kuzirian et al., *Biol. Bull.*, 2006, 210: 201-214. Additionally, Bryostatin-induced synaptogenesis for long-term associative memory was shown to be regulated by PKC activation. Hongpaisan et al., *Proc. Natl. Acad. Sci. USA*, 2007, 104: 19571-19576.

PKC activation has been associated with a variety of other conditions. For example, PKC activators have demonstrated neuroprotective activity in animal models of depression. See Sun et al., *Eur. J. Pharmacol.*, 2005, 512: 43-51. PKC activators are also associated with prevention and treatment of Parkinson's disease, bipolar disorder, and schizophrenia, mental retardation (and related diseases like autism).

PKC activators can be broad-spectrum activators, acting on multiple isoforms of PKC, or can be selective for certain isoforms. While all types of PKC activators are of interest, selective PKC activators may offer unique advantages because different isoforms perform different, and sometimes opposite, functions. For example, PKC-$\delta$ and PKC-$\theta$ are often regarded as having a pro-apoptotic function because they are components of the caspase apoptosis pathway. PKC-$\epsilon$, by contrast, has an opposite role: its activation promotes proliferation and cell survival, and inhibits apoptosis. See Nelson et al., *Trends in Biochemical Sciences*, 2009, 34(3): 136-145.

A variety of different PKC activators are known. Bryostatin, for example, is a macrolide lactone that competes for the PKC 1,2-diacylglycerol ("DAG") binding site with very high affinity, producing a brief activation period followed by a prolonged downregulation. Other PKC activators include phorbol esters, naphthalene sulfonamides, and oxidized lipids.

Polyunsaturated fatty acids ("PUFAs"), such as arachidonic acid and 2-hydroxy-9-cis-octadecenoic acid (i.e., minerval), are also known PKC activators. PUFAs are interesting molecules in that they are essential components of the nervous system. They are known to increase membrane fluidity, rapidly oxidize to highly bioactive products, and produce a variety of inflammatory and hormonal effects. In addition, they are of low molecular weight and are able to cross the blood-brain barrier. Further, PUFAs are stable to acid and base, making them potentially effective for oral administration. On the other hand, PUFAs are rapidly degraded and metabolized in the body.

Like PUFAs, certain derivatives of PUFAs have been shown to be PKC activators. For example, certain cyclopropanated PUFAs such as DCPLA (i.e., linoleic acid derivative), AA-CP4 methyl ester (i.e., arachidonic acid derivative), DHA-CP6 methyl ester (i.e., docosahexaenoic acid derivative), and EPA-CP5 methyl ester (i.e., eicosapentaenoic acid derivative) may be able to selectively activate PKC-$\epsilon$. See *Journal of Biological Chemistry*, 2009, 284(50): 34514-34521; see also U.S. Patent Application Publication No. 2010/0022645 A1.

SUMMARY OF THE DISCLOSURE

The present disclosure includes esters of 8-[2-(2-pentylcyclopropylmethyl)-cyclopropyl]-octanoic acid ("DCPLA") and compositions thereof. In one embodiment, the ester of DCPLA is chosen from alkyl esters, benzyl and aromatic esters, fatty alcohol esters, fatty acid esters, cyclopropanated fatty alcohols esters, cyclopropanated fatty acid esters, diacylglycerol esters, phosphatidyl serine esters, cholesteryl esters, and macrolide esters.

The disclosure further includes methods for improving learning, for improving memory, for reducing β-amyloid levels, for preventing or treating a disease associated with synaptic loss or synaptic damage, for preventing or treating neurodegenerative disorders and conditions, for preventing or treating depression, for preventing or treating stroke, and for preventing or treating brain injuries; these methods comprising administering to a subject in need thereof at least one ester of DCPLA.

Another aspect of the disclosure includes esters of DCPLA for use in methods for improving learning, for improving memory, for reducing β-amyloid levels, for preventing or treating a disease associated with synaptic loss or synaptic damage, for preventing or treating neurodegenerative disorders and conditions, for preventing or treating depression, for preventing or treating stroke, and for preventing or treating brain injuries.

BRIEF DESCRIPTION OF THE FIGURES

A graphical representation of MAP-2, PSD-95, and synaptophysin expression is shown in FIG. 10B.

FIG. 15: DCPLA-ME increases dendritic branching in rat primary neurons. Seven day old culture of rat hippocampal neurons were treated with DCPLA-ME (100 nM) for 48 h.

FIG. 16: PKC-ε activation prevents degeneration of human primary neurons. Primary human neurons were treated with either DCPLA-ME (100 nM) or bryostatin 1 (0.27 nM) for 40 days. Fresh drug was added every third day with 50% media change. FIG. 16A—Image of 40 day old untreated ("control"), bryostatin 1, and DCPLA-ME treated neurons. FIG. 16B—Number of neurite positive cells counted from three 20× fields (508 μm²) over time. DCPLA-ME and bryostatin 1 treatment stabilized cellular viability for at least 40 days. Viability of untreated cells declined after 20 days. FIG. 16C, FIG. 16D—Immunoblot analysis of PKCε in 40 day old neurons compared to 1 day neurons. DCPLA-ME protects PKC-ε. FIG. 16E—Immunoblot analysis of PSD-95 and synaptophysin after 40 day bryostatin or DCPLA-ME treatment. FIG. 16F, FIG. 16G—Immunostaining of PSD-95 and synaptophysin calculated from Western blots. Staining is significantly higher in DCPLA-ME and bryostatin 1 treated cells.

DEFINITIONS

Figure 1:
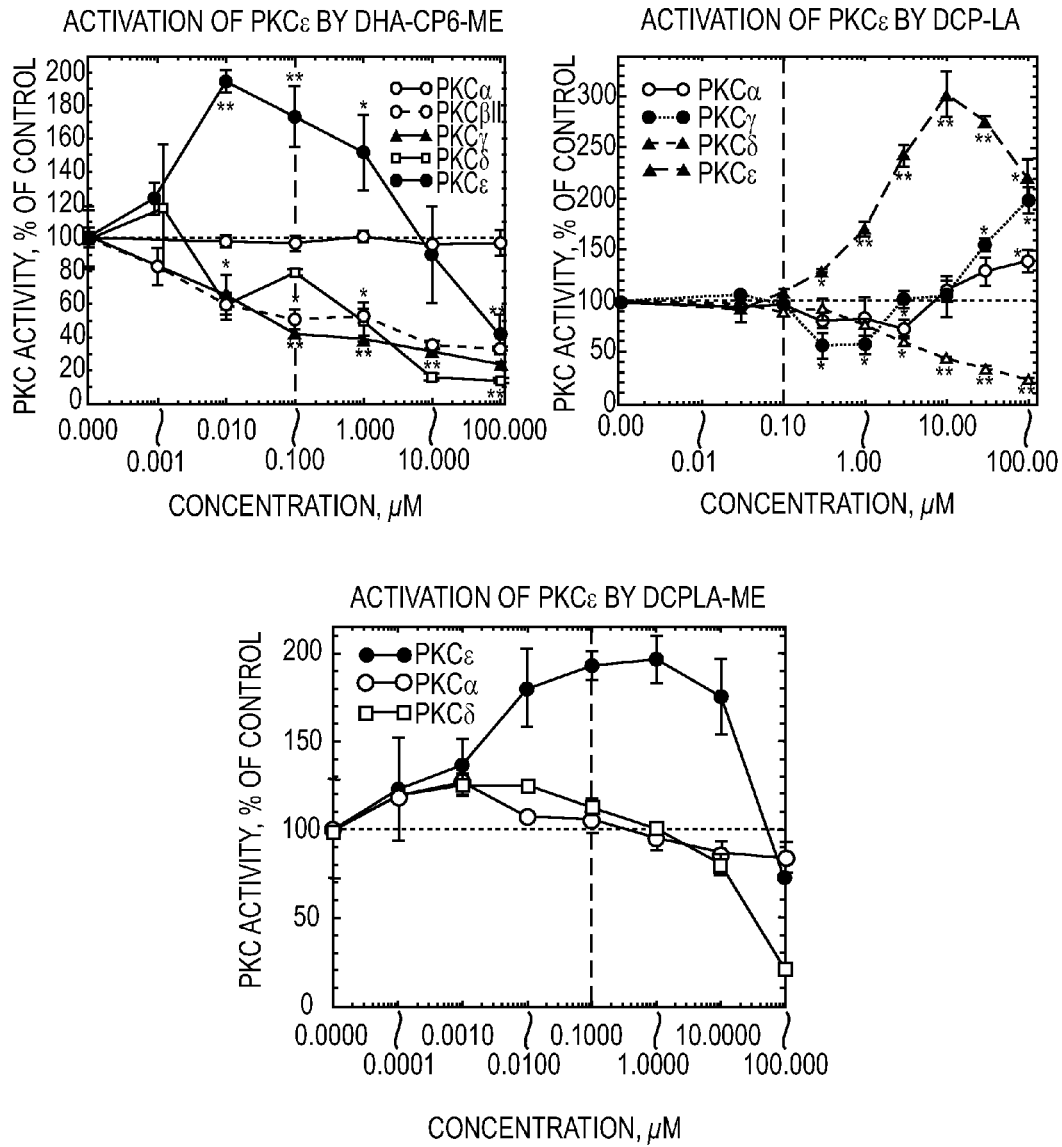
FIG. 1: PKC activation by DCPLA-methyl ester compared to DCPLA and DHA-CP6 (docosahexaenoic acid wherein each carbon-carbon double bond is replaced with a cyclopropane group).

As used herein, the singular forms "a," "an," and "the" include plural reference unless the context dictates otherwise.

As used herein, "protein kinase C activator" or "PKC activator" refers to a substance that increases the rate of the reaction catalyzed by protein kinase C by binding to the protein kinase C. As used herein, "selective activation" means activation of one PKC isozyme, e.g., PKC-ε, to a greater detectable extent than another PKC isozyme.

As used herein, the term "fatty acid" refers to a compound composed of a hydrocarbon chain and ending in free acid, an acid salt, or an ester. When not specified, the term "fatty acid" is meant to encompass all three forms. Those skilled in the art understand that certain expressions are interchangeable. For example, "methyl ester of DCPLA" is the same as "DCPLA methyl ester," which is the same as "DCPLA in the methyl ester form."

Fatty acids may be saturated or unsaturated, branched or unbranched, and naturally-occurring or synthetic. Linoleic acid is an example of a fatty acid (shown below in the free acid form).

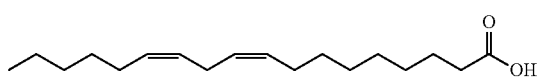 [SMILES: CCCCC/C=C\C/C=C\CCCCCCCC(=O)O]

An "unsaturated fatty acid" is a fatty acid that contains at least one carbon-carbon double bond within the hydrocarbon chain. Each double bond can be in cis or trans form.

A "monounsaturated fatty acid" or "MUFA" contains one carbon-carbon double bond. Oleic acid is an example of a monounsaturated fatty acid. A "polyunsaturated fatty acid" or "PUFA" contains more than one carbon-carbon double bonds. Linoleic acid is an example of a polyunsaturated fatty acid.

The terms "cyclopropanated monounsaturated fatty acid" or "cyclopropanated MUFA" refer to compounds wherein the carbon-carbon double bond is replaced by a cyclopropyl group. The cyclopropyl group may be in cis or trans configuration. Unless otherwise indicated, it should be understood that the cyclopropyl group is in the cis configuration. An example is of a cyclopropanated MUFA is 8-(2-octylcyclopropyl)octanoic acid (shown below in free acid form).

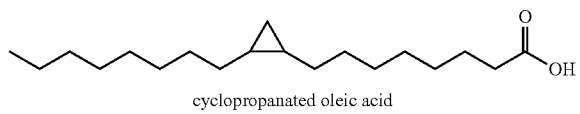 [SMILES: CCCCCCCCC1CC1CCCCCCCC(=O)O]

cyclopropanated oleic acid

The terms "cyclopropanated polyunsaturated fatty acid" or "cyclopropanated PUFA" refer to compounds wherein at least one of the carbon-carbon double bonds in the polyunsaturated fatty acid is replaced by a cyclopropyl group. The cyclopropyl group may be in cis or trans configuration. Unless otherwise indicated, it should be understood that the cyclopropyl group is in the cis configuration. An example of a cyclopropanated PUFA is 8-[2-(2-pentylcyclopropylmethyl)-cyclopropyl]-octanoic acid ("DCPLA") (shown below in the free acid form).

Esters of DCPLA can be prepared according to techniques known in the art. See, e.g., *Journal of Biological Chemistry*, 2009, 284(50): 34514-34521. For example, linoleic acid can be esterified using $SOCl_2$ in methanol and pyridine. The subsequent ester can then be cyclopropanated using a modified Simmons-Smith reaction with chloroiodomethane and diethylzinc.

Linoleic acid and esters thereof are generally commercially available. Alternatively, the acids and esters may be isolated from natural sources (e.g., vegetable oil) or synthesized (e.g., by chemical reactions). Esterification of linoleic acid can be performed according to known methods. For example, linoleic acid can be esterified with an alcohol in the presence of an acid.

EMBODIMENTS

The present disclosure includes esters of 8-[2-(2-pentylcyclopropylmethyl)-cyclopropyl]-octanoic acid ("DCPLA") and compositions, kits, and methods for treatment using the esters. In one embodiment, the ester of DCPLA is chosen from alkyl esters, benzyl and aromatic esters, fatty alcohol esters, fatty acid esters, cyclopropanated fatty alcohols esters, cyclopropanated fatty acid esters, diacylglycerol esters, phosphatidyl serine esters, cholesteryl esters, and macrolide esters.

While certain cyclopropanated polyunsaturated fatty acids ("PUFAs") have been found to activate PKC, there has been no appreciation of the activity of esters of DCPLA. For example, numerous references report the synthesis of the methyl ester of DCPLA ("DCPLA-ME") but disregard it as simply an intermediate in the synthesis of the final compound of interest, DCPLA. See, e.g., *Bioorganic & Medicinal Chemistry Letters*, 2003, 13: 1037-1040; U.S. Patent Application Publication No. 2005/0075393 A1; *Journal of Biological Chemistry*, 2009, 284(50): 34514-34521; and U.S. Patent Application Publication No. 2010/0022645 A1. In fact, while esters of other cyclopropanated PUFAs were being synthesized and tested, there was no appreciation in the art of the potential advantages of the esters of DCPLA. See, e.g., U.S. Patent Application Publication No. 2010/0022645 A1.

The present disclosure also includes the discovery that esters of DCPLA may activate PKC, and PKC-ε in particular. The esters of DCPLA may even be more selective and/or more potent PKC activators than the corresponding acid form (i.e., DCPLA). Additionally, the esters of DCPLA may be selective and/or more potent PKC activators than esters of other cyclopropanated PUFAs. Moreover, the esters of DCPLA may exhibit minimal downregulation of PKC isoforms such as PKC-δ. The esters of DCPLA may also be able to cross the blood-brain barrier. Further, the esters of DCPLA may avoid incorporation into triacylglycerols, and therefore exhibit a longer elimination half-life. The esters of DCPLA may also show sustained PKC activation compared to other PKC activators. Further, the esters of DCPLA may have a much greater affinity for PKC-ε than other PKC activators, such as DCPLA.

The present disclosure also relates to the alkyl esters of DCPLA. For example, the alkyl group may be methyl, ethyl, propyl (e.g., isopropyl), and butyl (e.g., tert-butyl). DCPLA in the methyl ester form ("DCPLA-ME") is shown below.

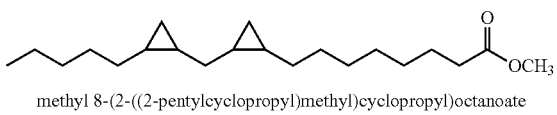 [SMILES: CCCCCC1CC1CC1CC1CCCCCCCC(=O)OC]

methyl 8-(2-((2-pentylcyclopropyl)methyl)cyclopropyl)octanoate

The alkyl group of the DCPLA alkyl esters may be linear, branched, and/or cyclic. The alkyl groups may be saturated or unsaturated. When the alkyl group is an unsaturated cyclic alkyl group, the cyclic alkyl group may be aromatic. In one embodiment, the DCPLA alkyl ester is derived from DCPLA and a branched alkyl alcohol. In another embodiment, the DCPLA alkyl ester is derived from DCPLA and a cyclic alkyl alcohol. Examples of branched and cyclic alkyl alcohols include the compounds shown below.

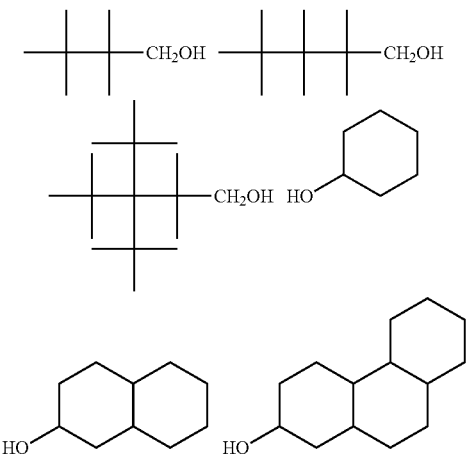

In another embodiment, the disclosure includes DCPLA benzyl esters, derived from DCPLA and a benzyl alcohol (unsubstituted benzyl alcohol ester shown below). The present disclosure further includes DCPLA aromatic esters, derived from DCPLA and aromatic alcohols such as phenols used as antioxidants and natural phenols with pro-learning ability. Some specific examples include estradiol, butylated hydroxytoluene, resveratrol, polyhydroxylated aromatic compounds, and curcumin.

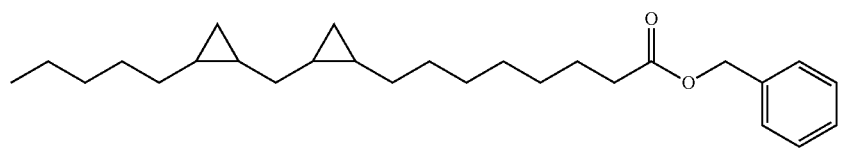

DCPLA-benzyl alcohol ester

The present disclosure also includes DCPLA fatty alcohol esters, derived from DCPLA and a fatty alcohol (i.e., a fatty acid that has been reduced to alcohol form). The fatty alcohols can be saturated, monounsaturated (MUFA alcohol), or polyunsaturated (PUFA alcohol). Two examples of esters of DCPLA and a fatty alcohol are the DCPLA-oleyl ester and the DCPLA-retinyl ester (shown below).

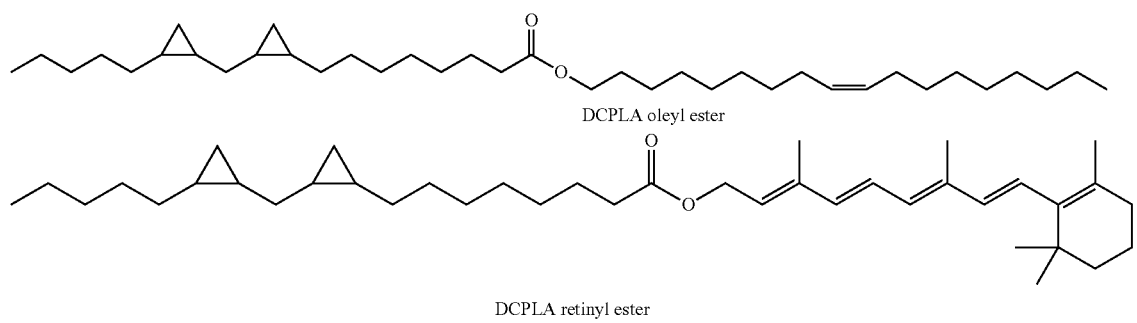

DCPLA oleyl ester

DCPLA retinyl ester

Other examples of fatty alcohols from which the DCPLA esters may be composed include linolenic alcohol, docosahexaenoic alcohol, eicosapentaenoic alcohol, and linoleic alcohol. Still further examples of fatty alcohols from which the DCPLA esters may be composed include those shown below. The stereochemistry of double bonds in the fatty alcohols from which the DCPLA esters may be composed, including the double bonds in the fatty alcohols depicted below, may be cis or trans.

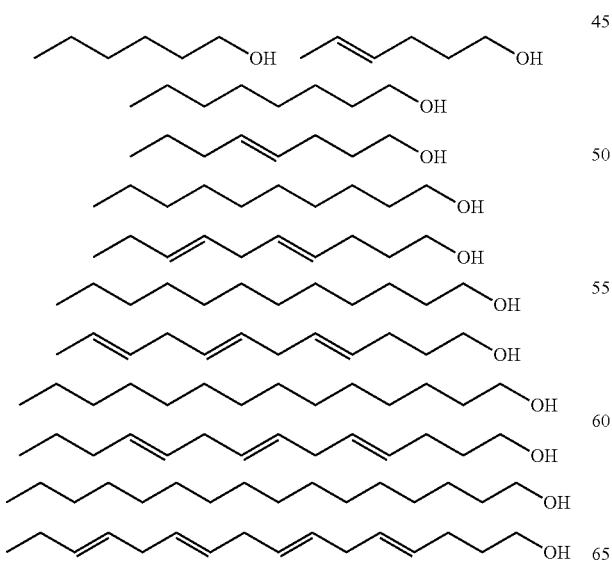

In one embodiment, the DCPLA esters of the present disclosure are DCPLA fatty acid esters. In these cases, rather than reducing the fatty acid to a fatty alcohol, DCPLA is reduced to the alcohol and esterified with the fatty acid. The fatty acids can be saturated, monounsaturated (MUFAs), or polyunsaturated (PUFAs). An example of this type of DCPLA ester is the retinoic acid-DCPLA alcohol ester (shown below).

Other examples of cyclopropanated fatty alcohols from which the DCPLA esters may be derived include those shown below. While the cyclopropanated fatty alcohols below are drawn in trans configuration, the corresponding cis compounds are additional examples of cyclopropanated fatty alcohols from which the DCPLA esters may be derived.

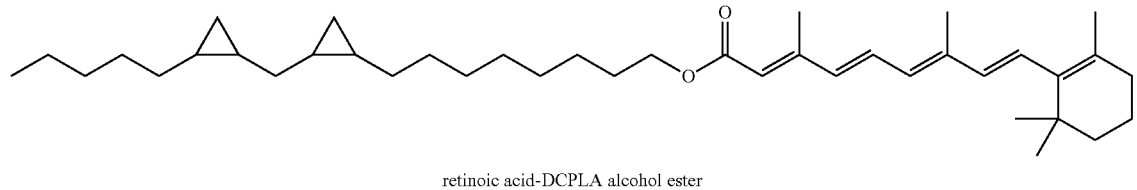 [SMILES: CCCCCC1CC1CC1CC1CCCCCCCCOC(=O)/C=C(C)/C=C/C=C(C)/C=C/C1=C(C)CCCC1(C)C]

retinoic acid-DCPLA alcohol ester

The present disclosure further includes DCPLA cyclopropanated fatty alcohol esters, derived from DCPLA and a cyclopropanated fatty alcohol. The cyclopropanated fatty alcohols can be saturated, monounsaturated (MUFA alcohols), or polyunsaturated (PUFA alcohols). The cyclopropanated PUFA alcohols can be cyclopropanated at one or more of the carbon-carbon double bonds. The cyclopropanated fatty alcohols from which the DCPLA cyclopropanated fatty alcohol esters are derived can be in cis or trans configuration. In one embodiment, the cyclopropanated fatty alcohol is in the cis configuration.

An example of a DCPLA cyclopropanated MUFA alcohol ester is the DCPLA-oleyl alcohol ester (shown below). An example of a DCPLA cyclopropanated PUFA alcohol ester is DCPLA-cyclopropanated docosahexaenoic alcohol ester. In the example shown below, each carbon-carbon double bond of docosahexaenoic alcohol is cyclopropanated. Other examples of cyclopropanated fatty alcohols from which the DCPLA esters may be derived include linoleic alcohol, linolenic alcohol, and eicosapentaenoic alcohol. When the ester is derived from cyclopropanated linoleic alcohol (where all carbon-carbon double bonds have been cyclopropanated), the compound is the DCPLA-DCPLA ester (shown below).

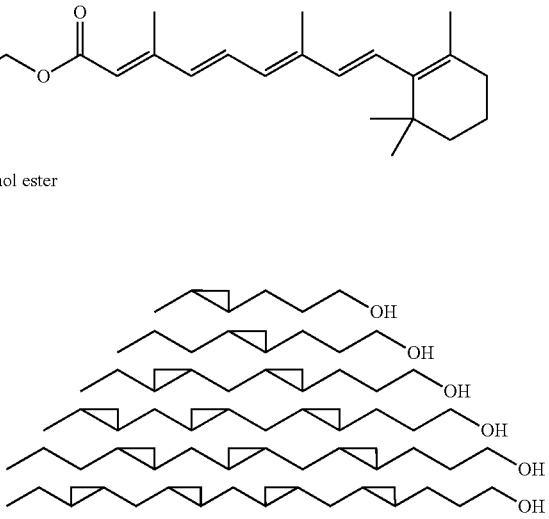

In one embodiment, the DCPLA esters of the present disclosure are DCPLA cyclopropanated fatty acid esters. In these cases, DCPLA is reduced to an alcohol and esterified with the cyclopropanated fatty acid. The cyclopropanated fatty acids can be saturated, monounsaturated (cyclopropanated MUFAs), or polyunsaturated (cyclopropanated PUFAs). The cyclopropanated fatty acids can be in cis or trans configuration. In one embodiment, the cyclopropanated fatty acid is in the cis configuration.

The present disclosure also includes DCPLA diacylglycerol esters. For example, the DCPLA ester of 1-palmitoyl-2-oleoyl-glycerol (shown below).

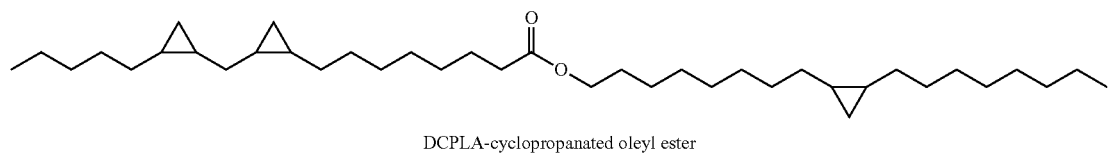

DCPLA-cyclopropanated oleyl ester

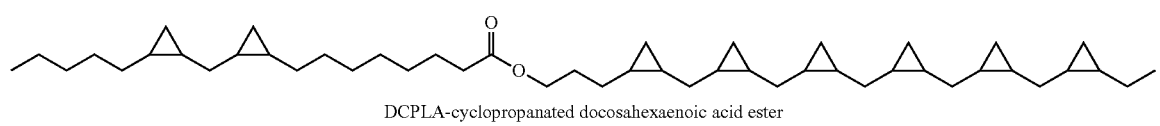

DCPLA-cyclopropanated docosahexaenoic acid ester

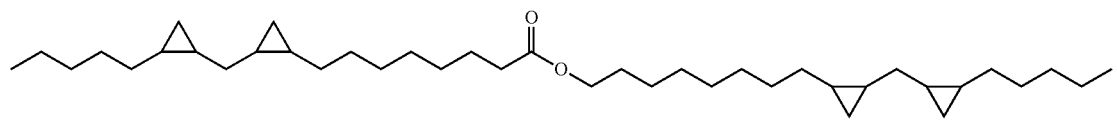

DCPLA-DCPLA ester

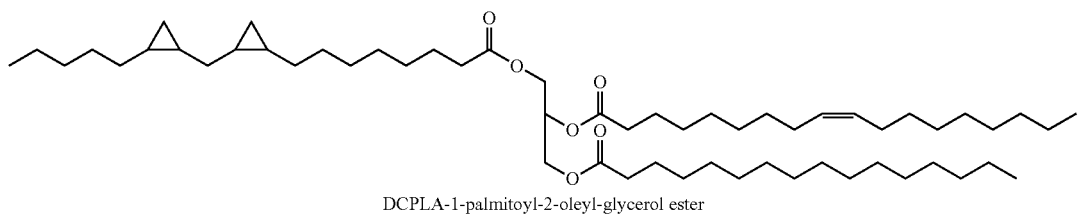 [SMILES: CCCCCCCC/C=C\CCCCCCCC(=O)OC(COC(=O)CCCCCCCCCCCCCCC)COC(=O)CCCCCCCC1CC1CC1CC1CCCCC]

DCPLA-1-palmitoyl-2-oleyl-glycerol ester

In another aspect, the present disclosure includes phosphatidyl esters of DCPLA. For example, the ester may be DCPLA-phosphatidyl serine (shown below) wherein the R group is any fatty acid chain. In one embodiment, the R group is chosen from oleic, palmitic, arachidonic, and docosahexaenoic fatty acid chains.

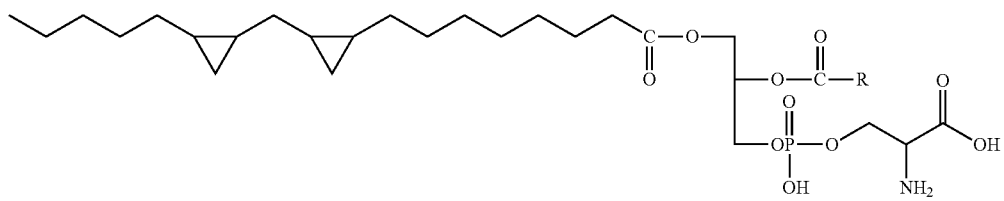

In another aspect of the disclosure, the ester of DCPLA is a DCPLA cholesteryl ester (shown below). In one embodiment, the ester is a DCPLA cholesterol derivative ester. For example, the carbon-carbon double bond in the cholesteryl group may be hydrogenated. In another embodiment, the stereochemistry is that of the naturally occurring cholesteryl molecule.

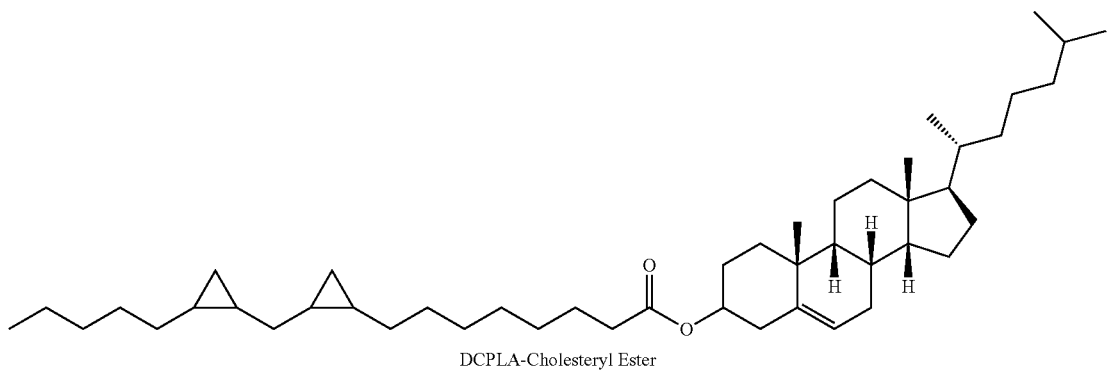

DCPLA-Cholesteryl Ester

The present disclosure also includes macrolide esters of DCPLA. For example, the ester of DCPLA can be a bryostatin ester. Two different examples of DCPLA-bryostatin esters are shown below.

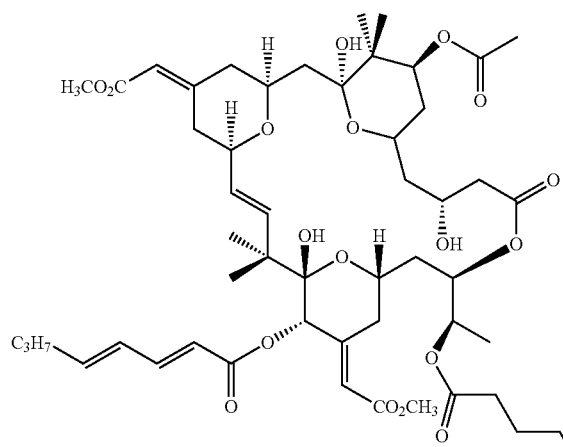

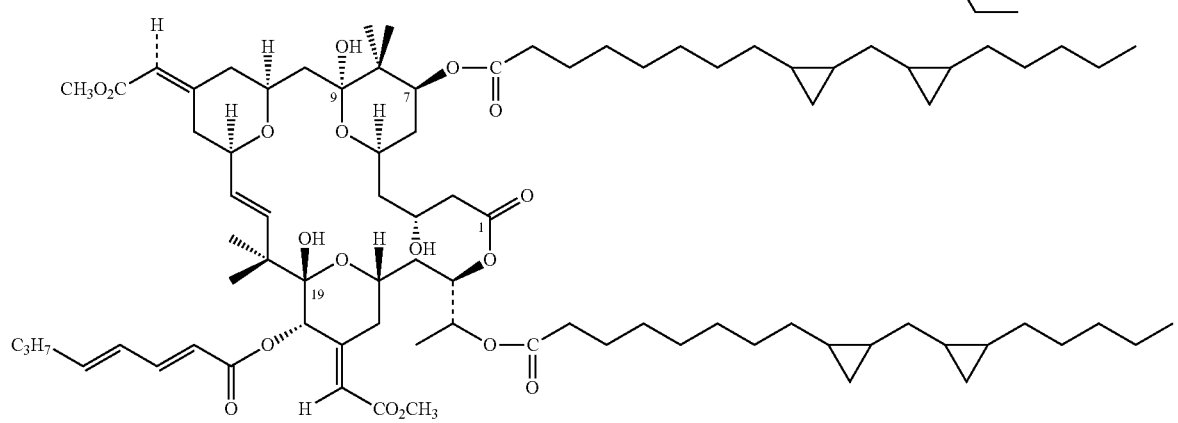

In one embodiment, the macrolide ester of DCPLA is a bryolog ester. Bryologs (i.e., analogs of bryostatin) may be esterified with DCPLA in the same manner as bryostatins. Bryostatin analogs are described, for example, in U.S. Pat. Nos. 6,624,189 and 7,256,286. See also U.S. patent application Ser. No. 13/178,821.

The present disclosure further includes compositions comprising one or more esters of DCPLA. The formulations of the pharmaceutical compositions described herein may be prepared by any suitable method known in the art of pharmacology. In general, such preparatory methods include bringing the active ingredient into association with a carrier or one or more other accessory ingredients, then, if necessary or desirable, shaping or packaging the product into a desired single- or multi-dose unit.

Although the descriptions of pharmaceutical compositions provided herein are principally directed to pharmaceutical compositions suitable for ethical administration to humans, it will be understood by a skilled artisan that such compositions are generally suitable for administration to animals of all sorts. Modification of pharmaceutical compositions suitable for administration to humans or to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure are contemplated include, but are not limited to, humans and other primates, and other mammals.

In one embodiment, at least one ester of DCPLA may be formulated with a pharmaceutically acceptable carrier for administration. Pharmaceutically acceptable carriers include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other additional ingredients that may be included in the pharmaceutical compositions of the disclosure are generally known in the art and may be described, for example, in *Remington's Pharmaceutical Sciences*, Genaro, ed., Mack Publishing Co., Easton, Pa., 1985, and *Remington's Pharmaceutical Sciences*, 20$^{th}$ Ed., Mack Publishing Co. 2000, both incorporated by reference herein.

In one embodiment, at least one ester of DCPLA may be formulated with pharmaceutically acceptable carrier wherein the carrier is a hydrophobic carrier. Hydrophobic carriers include inclusion complexes, dispersions (such as micelles, microemulsions, and emulsions), and liposomes. Exemplary hydrophobic carriers include inclusion complexes, micelles, and liposomes. See, e.g., Remington's: The Science and Practice of Pharmacy 20th ed., ed. Gennaro, Lippincott: Philadelphia, Pa. 2003, incorporated by reference herein. The esters of DCPLA may be incorporated into hydrophobic carriers, for example as at least 1%, at least 5%, at least 10%, at least 20%, at least 30%, at least 40%, at least 50%, at least 60%, at least 70%, at least 80%, or at least 90% of the total carrier by weight. In addition, other compounds may be included either in the hydrophobic carrier or the solution, e.g., to stabilize the formulation.

The compositions disclosed herein may be administrated by any suitable route including oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration. A suitable route of administration may be chosen to permit crossing the blood-brain barrier. See e.g., *J. Lipid Res*. (2001) vol. 42, pp. 678-685, incorporated by reference herein.

In one embodiment, at least one ester of DCPLA is formulated in a solid oral dosage form. For oral administration, the composition may take the form of a tablet or capsule prepared by conventional means with pharmaceutically acceptable carriers such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods generally known in the art.

In another embodiment, at least one ester of DCPLA is formulations into a liquid preparation for oral administration. Such a preparation may take the form of, for example, solutions, syrups or suspensions, or they may be presented as a dry product for constitution with water or other suitable vehicle before use. Such liquid preparations may be prepared by conventional means with pharmaceutically acceptable carriers such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl p-hydroxybenzoates, or sorbic acid). The preparations may also comprise buffer salts, flavoring, coloring, and sweetening agents as appropriate.

In another embodiment of the present disclosure, at least one ester of DCPLA may be formulated for parenteral administration such as bolus injection or continuous infusion. Formulations for injection may be presented in unit dosage form, e.g., in ampoules, or in multi-dose containers, with an added preservative. The compositions may take such forms as suspensions, solutions, dispersions, or emulsions in oily or aqueous vehicles, and may contain formulatory agents such as suspending, stabilizing, and/or dispersing agents.

In another embodiment, at least one ester of DCPLA may be formulated as a depot preparation. Such long acting formulations may be administered by implantation (for example, subcutaneously or intramuscularly) or by intramuscular injection. For example, at least one ester of DCPLA may be formulated with a suitable polymeric or hydrophobic material (for example, as an emulsion in an acceptable oil) or ion exchange resin, or as a sparingly soluble derivative, for example, as a sparingly soluble salt.

In another embodiment, at least one ester of DCPLA may be delivered in a vesicle, such as a micelle, liposome, or an artificial low-density lipoprotein (LDL) particle. See, e.g., U.S. Pat. No. 7,682,627.

In one embodiment, the at least one ester of DCPLA is present in a composition in an amount effective for improving learning, for improving memory, for reducing β-amyloid levels, for preventing or treating a disease associated with synaptic loss or synaptic damage, for preventing or treating a neurodegenerative disorder or condition, for preventing or treating depression, for preventing or treating stroke, or for preventing or treating a brain injury.

In a further embodiment, the doses for administration may suitably be prepared so as to deliver from about 1 mg to about 10 g, such as from about 5 mg to about 5 g, from about 50 mg to about 2 g, from about 100 mg to about 1.5 g, from about 150 mg to about 1 g, or from about 250 mg to about 500 mg of at least one ester of DCPLA per day.

In one embodiment, the ester or esters of DCPLA may be present in the composition in an amount ranging from about 0.01% to about 100%, from about 0.1% to about 90%, from about 0.1% to about 60%, from about 0.1% to about 30% by weight, or from about 1% to about 10% by weight of the final formulation. In another embodiment, the ester or esters of DCPLA may be present in the composition in an amount ranging from about 0.01% to about 100%, from about 0.1% to about 95%, from about 1% to about 90%, from about 5% to about 85%, from about 10% to about 80%, and from about 25% to about 75%.

The present disclosure includes kits that may be utilized for preparing and administering pharmaceutical compositions of at least one ester of DCPLA.

The kits may comprise devices such as syringes for administration of the pharmaceutical compositions described herein. In one embodiment, the kits may comprise one or more vials, syringes, needles. In another embodiment, the kits may comprise ampules, cartridges, bottles or other such vessels for storing and/or subsequently mixing compositions of at least one ester of DCPLA. In another embodiment, the devices, syringes, ampules, cartridges, bottles or other such vessels for storing and/or subsequently mixing the compositions of at least one ester of DCPLA disclosed herein may, or may not have more than one chamber.

In still another embodiment, the compositions of at least one ester of DCPLA disclosed herein may be stored in one or more graduated vessels (such as a syringe or syringes or other device useful for measuring volumes).

In a further embodiment, the kits may comprise pharmaceutical compositions of at least one ester of DCPLA stored within the same or separate ampules, vials, syringes, cartridges, bottles, or other such vessels. The kits may also include additional buffers, needles, needle-less injection devices, sterile pads, or swabs.

The kits may also comprise one or more anesthetics, such as local anesthetics. In one embodiment, the anesthetics are in a ready-to-use formulation, for example an injectable formulation (optionally in one or more pre-loaded syringes), or a formulation that may be applied topically to an area where the compositions of at least one ester of DCPLA disclosed herein are to be administered.

Topical formulations of anesthetics may be in the form of an anesthetic applied to a pad, swab, towelette, disposable napkin, cloth, patch, bandage, gauze, cotton ball, Q-tip™, ointment, cream, gel, paste, liquid, or any other topically applied formulation. Anesthetics for use with the present disclosure may include, but are not limited to lidocaine, marcaine, cocaine, and xylocaine, for example.

The kits may also contain instructions relating to the use of the pharmaceutical compositions of at least one ester of DCPLA and procedures for mixing, diluting, or combining formulations of at least one ester of DCPLA. The instructions may also contain directions for properly diluting formulations of at least one ester of DCPLA to obtain a desired pH or range of pHs and/or a desired specific activity and/or protein concentration after mixing but prior to administration. The instructions may also contain dosing information. The instructions may also contain material directed to methods for selecting subjects for treatment with the disclosed pharmaceutical compositions of at least one ester of DCPLA.

The present disclosure includes methods and/or uses of at least one ester of DCPLA. For example, the present disclosure provides a method for improving learning comprising: administering to a patient in need thereof an effective amount of at least one ester of DCPLA. In another embodiment, the present disclosure includes methods for improving memory comprising: administering to a patient in need thereof an effective amount of at least one ester of DCPLA.

In yet another embodiment, the present disclosure provides for a method for reducing β-amyloid levels comprising: administering to a patient in need thereof an effective amount of at least one ester of DCPLA. The present disclosure further includes a method for preventing or treating a disease associated with synaptic loss or synaptic damage comprising: administering to a patient in need thereof an effective amount of at least one ester of DCPLA.

The present disclosure further includes a method for preventing or treating at least one disease or condition is chosen from neurodegenerative disorders and conditions, depression, stroke, mental retardation, and brain injuries comprising: administering to a patient in need thereof an effective amount of at least one ester of DCPLA. The neurodegenerative disorder may be, for example, Alzheimer's disease and Parkinson's disease. The neurodegenerative disorder or condition may be caused by, for example, exposure to at least one neurotoxic chemical such as a heavy metal. The brain injury may be traumatic brain injury or brain injury induced by irradiation.

A further aspect of the disclosure is the use of at least one ester of DCPLA in the preparation of a medicament for improving learning, for improving memory, for reducing β-amyloid levels, for preventing or treating a disease associated with synaptic loss or synaptic damage, for preventing or treating neurodegenerative disorders and conditions, for preventing or treating depression, for preventing or treating stroke, and for preventing or treating brain injuries.

Another aspect of the disclosure includes an ester of DCPLA for use in improving learning, improving memory, reducing β-amyloid levels, preventing or treating a disease associated with synaptic loss or synaptic damage, preventing or treating neurodegenerative disorders and conditions, preventing or treating depression, preventing or treating stroke, and preventing or treating brain injuries.

Esters of DCPLA may be administered by conventional methods such as oral, parenteral, transmucosal, intranasal, inhalation, or transdermal administration. Parenteral administration includes intravenous, intra-arteriolar, intramuscular, intradermal, subcutaneous, intraperitoneal, intraventricular, intrathecal, and intracranial administration.

In one embodiment, at least one ester of DCPLA is present in a composition in an amount effective for improving learning, for improving memory, for reducing β-amyloid levels, for preventing or treating a disease associated with synaptic loss or synaptic damage, for preventing or treating neurodegenerative disorders and conditions, for preventing or treating depression, for preventing or treating stroke, and for preventing or treating brain injuries.

EXAMPLES

All numbers used in herein are to be understood as being modified in all instances by the term "about."

Synthetic Procedures

Synthesis of DCPLA and DCPLA Methyl Ester:

DCP-LA and DCPLA-ME were synthesized following an earlier described method. See Nelson et al. (2009) *J Biol Chem* 274, 34514-34521. Briefly, linoleic acid methyl ester (commercially available) was cyclopropanated using the modified Simmons-Smith reaction using chloroiodomethane and diethylzinc. See Tanaka et al. (2003) *Bioorg Med Chem Lett*, 13: 1037-1040; Furukawa et al. (1967) *Tetrahedron*, 24: 53-58; and Denmark et al. (1991) *J Org Chem*, 56: 6974-6981.

All apparatus was baked at 60° C. for 1 hr and flame-dried while passing dry nitrogen through the apparatus. A 100-ml three-neck round-bottom flask with a stirring bar and a temperature probe was surrounded by a dry ice mixture and filled with 1.25 g (4.24 mmol) of linoleic acid methyl ester in 25 ml of dichloromethane and bubbled with $N_2$. A 1 M solution of diethylzinc (51 ml, 54.94 mmol) in hexane was added anaerobically using a 24-inch-long 20-gauge needle, and the solution was cooled to −5° C. Chloroiodomethane ($ClCH_2I$, 8.02 ml, 109.88 mmol) was added dropwise, 1 drop/s, with constant stirring. The rate of addition was decreased if necessary to maintain the reaction mixture below 2° C. The reaction mixture became cloudy during the reaction, and an insoluble white zinc product was produced. The flask was sealed, and the mixture was allowed to react further for 1 hr and then allowed to come to room temperature gradually over 2 hr.

To prevent the formation of an explosive residue in the hood, diethylzinc was not evaporated off. The mixture was poured slowly into 100 ml of water under stirring to decompose any excess diethylzinc. Ethane was evolved. The mixture was centrifuged at 5000 rpm in glass centrifuge tubes, and the upper aqueous layer was discarded. The white precipitate was extracted with $CH_2Cl_2$ and combined with the organic phase. The organic phase was washed with water and centrifuged. The product was analyzed by Silica Gel G TLC using hexane+1% ethyl acetate and purified by chromatography on silica gel using increasing concentrations of 1-10% ethyl acetate in n-hexane and evaporated under nitrogen, leaving the DCPLA methyl ester as a colorless oil. The Simmons-Smith reaction preserves the stereochemistry of the starting materials.

To obtain DCPLA, 0.15 g of DCPLA methyl ester was dissolved in 1 ml of 1 N LiOH and 1 ml of dioxane. Dioxane and methanol were added until the mixture became homogeneous, and the solution was stirred 60° C. overnight to 3 days. The product was extracted in $CH_2Cl_2$ and centrifuged. The aqueous layer and white interface were reextracted with water and washed until the white layer no longer formed. The product was evaporated under $N_2$ and purified by chromatography on silica gel. The product, a colorless oil, eluted in 20% EtOAc in n-hexane. Its purity was checked by TLC in 10% EtOAc/hexane and by C18 reversed phase HPLC with UV detection at 205 nm, using 95% acetonitrile as the mobile phase.

Synthesis of $H^3$-DCPLA-ME:

Methylation of 3H-Linoleic Acid:

Linoleic acid$[9,10,12,13]^3$H (120 Ci/mmol) was evaporated to dryness in a 2 ml ReactiVial. Thionyl chloride (0.5 ml) was immediately added and the sealed vial was incubated at 60° C. overnight. Methanol (1 ml) was added and the mixture was evaporated and dissolved in dichloromethane.

Cyclopropanation:

Simmons-Smith cyclopropanation was carried out using $ClCH_2I$ as described above and the DCPLA-ME product was extracted into $CH_2Cl_2$ and purified by column chromatography. The radioactive lipid fractions were combined, evaporated, and stored in 100 µl EtOH to prevent radioactive decomposition.

Column Chromatography:

A glass column (22 mm i.d.×200 mm long or 36 mm i.d.×200 mm long) with a coarse frit was filled with silica gel 130-270 mesh, 60 Angstrom, pore volume 0.74 $cm^3$/g. The sample was applied and washed with 50 ml hexane. The product was eluted by sequential addition of 50 ml solvent of gradually increasing polarity (hexane, followed by increasing concentrations of ethyl acetate in hexane, then ethanol). Fractions containing product were evaporated under nitrogen.

Thin-Layer Chromatography:

TLC was performed on 5×20 cm silica gel G TLC plates containing fluorescent indicator. Solvents were hexane+1% ethyl acetate. Detection was by UV absorbance, colorimetric detection with $I_2$ and charring (spraying with 10% $H_2SO_4$ followed by heat).

Synthesis of DHA-CP6:

3-(2-((2-((2-((2-((2-((2-ethyl-cyclopropyl)methyl)cyclopropyl)methyl)cyclopropyl)methyl)cyclopropyl)methyl)cyclopropyl)methyl)cyclopropyl)propanoic acid (DHA-CP6) was prepared according to the procedures above for preparing DCPLA except that docosahexaenoic acid methyl ester (commercially available) was used in place of the linoleic acid methyl ester. See Nelson et al., *J. Biol. Chem.*, 2009, 274, 34514-34521.

Synthesis of DCPLA-Ethyl Ester:

Methyl linoleate (2 g) was incubated with anhydrous ethanol (20 ml), KOH (0.2 g), and 4 g of molecular sieves for 20 minutes at 60° C. with stirring. The reaction mixture was neutralized acetic acid and the ethyl linoleate product was extracted with ethyl acetate. Ethyl linoleate was cyclopropanated as described above using the Simmons-Smith reaction to produce DCPLA-ethyl ester. All reactions were carried out under a nitrogen atmosphere.

Synthesis of DCPLA-Isopropyl Ester:

Isopropyl linoleate (commercially available) was prepared by refluxing methyl linoleate (3 g) with isopropanol (20 ml) and lithium hydroxide (1 g) for 2 hours in a 50 ml round bottom flask with condensor. The product was purified by flash chromatography. The resultant isopropyl linoleate was then subject to the Simmons-Smith reaction described above to generate the DCPLA-isopropyl ester.

Alternative Synthesis of DCPLA-Isopropyl Ester:

Methyl linoleate (2 g) was transesterified by reacting with isopropanol (20 ml) and KOH (0.2 g) over 4 g molecular sieves at 60° C. in a sealed bottle under a nitrogen atmosphere. After 20 minutes, the mixture was neutralized with acetic acid and isopropyl linoleate product was extracted into ethyl acetate. The resultant isopropyl linoleate was then subjected to the Simmons-Smith reaction described above to produce DCPLA-isopropyl ester.

Synthesis of DCPLA-Tert-Butyl Ester:

DCPLA (100 mg) and N,N-dimethylformamide di-tert-butyl acetal (0.25 ml) were incubated with toluene (0.4 ml) at 60° C. for several days. The resultant DCPLA-tert-butyl ester was extracted with hexane and purified by flash chromatography (10% EtOAc/hexane).

Synthesis of DCPLA-Cyclopropanated Oleyl Ester:

Oleyl linoleate was prepared by refluxing linoleic acid (1 g) and Oeyl alcohol (1 ml) in $CH_2Cl_2$ (20 ml) and concentrated $H_2SO_4$ (10 µl) overnight. The product was slightly pink and was purified by flash chromatography. The resultant Oeyl linoleate was subjected to the Simmons-Smith procedure described above to generate DCPLA-oleyl ester.

Synthesis of DCPLA-Retinyl Ester:

DCPLA-ME (50 mg) and retinol (50 mg) were evaporated to dryness. Hexane (1 ml) was added along with lipase acrylic beads from *Candida antarctica* (0.2 g), and the mixture was incubated overnight at 60° C., protected from light. The product was purified by thin layer chromatography using 50 hexane: 5 ethyl acetate: 5 acetone.

Synthesis of DCPLA-Cholesteryl Ester and Cholesteryl Linoleate:

DCPLA (1 g), cholesterol (1 g), $CH_2Cl_2$ (20 ml), and concentrated $H_2SO_4$ (1 µl) were combined and refluxed overnight. The product was washed with sodium phosphate (pH 7.0, 5 ml) and purified by flash chromatography to yield the DCPLA-cholesteryl ester. Linoleic acid (1 g), cholesterol (1 g), $CH_2Cl_2$ (20 ml), and concentrated $H_2SO_4$ (20 µl) were combined and refluxed overnight. The product was washed with sodium phosphate (pH 7.0, 5 ml) and purified by flash chromatography to yield the cholesteryl linoleate.

Alternative Synthesis of DCPLA-Cholesteryl Ester:

DCPLA-ME (0.1 g), cholesterol (0.1 g), hexane (10 ml), and *Candida antarctica* lipase acrylic beads (1 g) can be combined and incubated at 60° C. overnight. The produce can be washed with sodium phosphate (pH 7.0, 5 ml) and can be purified by flash chromatography to yield DCPLA-cholesteryl ester.

Synthesis of DCPLA-Bryostatin Ester:

DCPLA-ME (1 mg) and Bryostatin 1 (1 mg) can be evaporated to dryness. Hexane (1 ml) can be added along with lipase acrylic beads from *Candida antarctia* (0.2 g), and the mixture can be incubated overnight at 60° C. The product can be purified by flash chromatography.

General Procedures

Materials—

Cell culture media were obtained from Invitrogen, USA (F12K, Neurobasal, and B27) and K.D. Medical, USA (MEM). $A\beta_{1-42}$ was purchased from Anaspec (San Jose, Calif.). Bryostatin 1 was purchased from Biomol International, USA. Primary antibodies (PKC-ε, β-actin, RACK1, synaptophysin, MAP-2, and PSD-95) were obtained from Santa Cruz Biotechnology, Inc, USA; phospho-GSK-3β (Ser 9) and GSK-3β from Cell Signaling Technology, USA; and β-tubulin was purchased from Millipore, USA. All secondary antibodies were purchased from Jackson ImmunoResearch Laboratories, USA. PKC-ε translocation inhibitor [EAVS-LKPT] and bisindolylmaleimide I (Go 6850) was procured from EMD Biosciences, USA. All other reagents were purchased from Sigma-Aldrich.

Cell Culture—

Rat hippocampal neurons (NeuroPure, Genlantis, USA) from 18-day-old embryonic Sprague-Dawley rat brains were plated on 24-well plates coated with poly-D-lysine (Sigma- Aldrich) in neurobasal medium supplemented with B-27 containing 0.5 mM glutamine and 25 μM glutamate (Invitrogen). The neuronal cells were grown under 5% $CO_2$ for 14 days in an incubator maintained at 37° C. Human SH-SY5Y neuroblastoma cells (ATCC) were cultured in 45% F12K, 45% minimum Eagle's medium, 10% fetal calf serum.

For differentiation, SH-SY5Y cells were maintained in medium containing 2% serum and treated with 10 μM all-trans-retinoic acid (RA) for 72 hr. Thereafter, the cells were treated with 0.27 nM Bryostatin 1 for 72 hrs. The medium was changed every 3 days with fresh supplementation of RA.

Preparation of Different Aβ Oligomers—

Amylospheroids (ASPDs) and Aβ monomers were prepared following Hoshi, M., et al. (2003) *Proc Natl Acad Sci USA* 100, 6370-6375, and Noguchi, A., et al. (2009) *J Biol Chem* 284, 32895-32905. Briefly, $A\beta_{1-42}$ was dissolved in 1,1,1,3,3,3-hexafluoro-2-propanol and incubated overnight at 4° C. and then 3 hr at 37° C. The dissolved $A\beta_{1-42}$ was then lyophilized in 1.5 ml polypropylene centrifuge tubes at 40 nmol/tube concentration. For preparing the ASPDs, the lyophilized Aβ was dissolved in phosphate buffered saline (PBS) without $Ca^{2+}$ or $Mg^{2+}$ at less than 50 μM concentration and rotated for 14 hr at 4° C. After incubation, the Aβ solution was purified using a 100 kDa molecular mass cutoff filter (Amicon Ultra, Millipore) and the high-molecular weight fraction was saved to obtain the most toxic ASPDs. Aβ derived diffusible ligands (ADDLs) were produced as previously described. See Lambert, M. P et al., *Proc. Natl. Acad. Sci. USA*, 1998, 95: 6448-6453. Briefly, $A\beta_{1-42}$ was solubilized at 5 mM in dimethyl sulfoxide, diluted to 100 μM in F12k medium and was incubated at 4° C. for 24 hr. The solution was centrifuged at 14000×g for 10 min at 4° C. and the supernatant was used as the ADDLs.

Size-Exclusion Chromatography (SEC)—

The prepared ASPDs and ADDLs were separated by SEC to estimate the molecular weight of the assemblies. SEC was performed using a HPLC (Shimadzu) connected with TSKgel Super SW2000 column (Supelco). Molecular weight calibration was conducted using both high and low molecular weight proteins. Aβ assemblies were separated with buffer containing 0.1 M $Na_2PO_4$ and 0.1 M $Na_2SO_4$ adjusted to pH 6.65 with $H_3PO_4$ at 0.1 ml/min, with absorbance being monitored at 280 nm.

Viability Assay—

Viability of cells was measured by MTT assay. MTT (i.e., 3-(4,5-dimethylthiazol-2-yl)-2,5-diphenyltetrazolium bromide) is a tetrazolium salt that is cleaved to formazan by the succinate dehydrogenase, which is only active in viable cells. After solubilization of the formazan, the amount of dye can be quantified with a microplate reader at 570 nm along with a reference of 630 nm. For the MTT assay, $5 \times 10^4$ primary rat hippocampal neurons from 18-day-old embryonic Sprague-Dawley rat brains or SH-SY5Y cells were plated on each well of 24-well plates coated with poly-D-lysine. After treatment, the cells were washed with 1× PBS and were incubated with 200 μl of 1 mg/ml MTT solution (Sigma, USA) at 37° C. for 2 hr. Then the MTT-solution was removed and the cells were lysed with 200 μl isopropanol containing 0.04 M HCl and 160 mM NaOH for 10 min. Finally, the reading was taken at 570 nm and 630 nm. All the samples were done in triplicate and the data were represented as the percentage of control.

PKC Assay—

For measurement of PKC activation by DCPLA-ME, activation of recombinant PKC-α, PKC-ε, and PKC-δ was evaluated. DCPLA-ME induced activation was measured in the absence of diacylglycerol (DAG) and phosphatidylserine (PS) as described earlier. See Nelson, T. J. et al., *J. Biol. Chem.*, 2009, 284: 34514-34521, and Kanno, T. et al., *J. Cell Physiol.*, 2009, 221: 183-188. Individual enzymes were incubated for 15 min at 37° C. in the presence of 10 μM histones, 4.89 mM $CaCl_2$, 10 mM $MgCl_2$, 20 mM HEPES (pH 7.4), 0.8 mM EDTA, 4 mM EGTA, 4% glycerol, 8 μg/ml aprotinin, 8 μg/ml leupeptin, 2 mM benzamidine, and 0.5 μCi of [$\gamma$-$^{32}$P] ATP. Purified PKC-α, PKC-ε and PKC-δ were preincubated with DCPLA-ME for 5 min at room temperature. [$^{32}$P]-Phosphoprotein formation was measured by adsorption onto phosphocellulose.

Immunofluorescence and Confocal Microscopy—

Cells were grown in two chambered slides (Nunc, USA) at low density. For immunofluorescence staining, the cells were washed with PBS (pH 7.4) and fixed with 4% paraformaldehyde for 4 min. Following fixation, the cells were blocked and permeabilized with 5% serum and 0.3% Triton X-100 in 1×PBS for 30 min. Cells were washed three times with 1×PBS and incubated with primary antibodies for 1 hr at 1:100 dilution. After the incubation, the slides were again washed three times in 1×PBS and were incubated with the FITC anti-mouse IgG and Rhodamine anti-rabbit IgG for 1 hr at 1:400 dilution. The cells were further washed and stained with DAPI (4',6-diamidino-2'-phenylindole, dihydrochloride) (Thermo Scientific, USA) to stain the nucleus. Finally, the slides were washed and mounted in Pro Long Gold antifade mounting solution (Invitrogen, USA) and were viewed under a LSM 710 Meta confocal microscope (Zeiss) at 350 nm, 490 nm, and 540 nm excitation and 470 nm, 525 nm, and 625 nm emission for DAPI, FITC, and Rhodamine respectively. Six individual fields at 63× oil lens magnification were analyzed for the mean fluorescence intensity (MFI) in each channel.

Cell Lysis and Western Blot Analysis—

Cells were harvested in homogenizing buffer containing 10 mM Tris-Cl (pH 7.4), 1 mM PMSF (phenylmethylsulfonyl fluoride), 1 mM EGTA, 1 mM EDTA, 50 mM NaF, and 20 μM leupeptin, and were lysed by sonication. The homogenate was centrifuged at 100,000×g for 15 min at 4° C. to obtain the cytosolic fraction (supernatant) and membrane (pellet). The pellet was resuspended in the homogenizing buffer by sonication. For whole cell protein isolation from primary neurons, the homogenizing buffer contained 1% Triton X-100. Protein concentration was measured using the Coomassie Plus (Bradford) Protein Assay kit (Pierce, USA). Following quantification, 20 μg of protein from each sample was subjected to SDS-PAGE analysis in a 4-20% gradient Tris-Glycine gel (Invitrogen, USA). The separated protein was then transferred to a nitrocellulose membrane. The membrane was blocked with 5% BSA at room temperature for 15 min and was incubated with primary antibody overnight at 4° C. After the incubation, it was washed three times with TBS-T (Tris Buffered Saline-Tween 20) and further incubated with alkaline phosphatase conjugated secondary antibody (Jackson Immunoresearch Laboratories, USA) at 1:10000 dilution for 45 min. The membrane was finally washed three times with TBS-T and developed using the 1-step NBT-BCIP substrate (Pierce, USA). The blot was imaged in an ImageQuant RT-ECL (GE Life Sciences, Piscataway, N.J.) and densitometric quantification was performed using IMAL software (Blanchette Rockefeller Neurosciences Institute, Morgantown, W. Va.). For translocation assays, PKC activation was represented as the percentage of total protein in the membrane (membrane/cytosol+membrane).

Reverse Transcription Polymerase Chain Reaction (RT-PCR)—

RNA was isolated from the cells using Trizol reagent (Invitrogen, USA) following the manufacturer's protocol.

Briefly, 5 μg of the total RNA was reverse transcribed using oligo (dT) and Superscript III (Invitrogen, USA) at 50° C. for 1 hr. Two μl of the cDNA product was amplified using primers for PKC-ε (Forward Primer—TGGCTGACCTTGGTGT-TACTCC, Reverse primer—GCTGACTTGGATCG-GTCGTCTT (Origene, Rockville, Md.)) and β-actin (Promega, USA) for 30 cycles following standard PCR protocols using a 55° C. annealing temperature. The PCR amplicons were analyzed in an E-Gel (Invitrogen, USA). The gel was imaged using a Fuji Image gel scanner (FLA-9000, Fuji Film) and densitometric quantification was performed using IMAL software (Blanchette Rockefeller Neurosciences Institute, Morgantown, W. Va.). Data were represented as normalized ratio of PKC-ε OD (Optical Density) against β-actin OD for three independent experiments.

Statistical Analysis—

All the experiments were performed in triplicates or more. Data are represented as mean±SE. Statistical analysis was performed by Student's t-test using Graph Pad Prism 5 software with P<0.05 considered statistically significant.

Example 1

DCPLA-ME has Less Inhibitory Effect on PKC-δ than DCPLA and DHA-CP6

(A) Measure of Total PKC Activity in Cultured Cells—

After removal of culture medium, cells were scraped in 0.2 ml homogenization buffer (20 mM Tris-HCl, pH 7.4, 50 mM NaF, 1 μg/ml leupeptin, and 0.1 mM PMSF) and immediately homogenized in the cell culture plate by sonication in a Marsonix microprobe sonicator (5 sec, 10 W). Aliquots were transferred immediately after sonication to 0.5 ml centrifuge tubes and frozen at −80°.

(B) Measure of PKC Activation—

To measure PKC, 10 μl of cell homogenate or purified PKC isozyme was incubated for 15 min at 37° C. in the presence of 10 μM histones, 4.89 mM $CaCl_2$, 1.2 μg/μl phosphatidyl-L-serine, 0.18 μg/μl 1,2-dioctanoyl-sn-glycerol, 10 mM $MgCl_2$, 20 mM HEPES (pH 7.4), 0.8 mM EDTA, 4 mM EGTA, 4% glycerol, 8 μg/ml aprotinin, 8 μg/ml leupeptin, and 2 mM benzamidine. [γ32P]ATP (0.5 μCi) was added and 32P-phosphoprotein formation was measured by adsorption onto phosphocellulose as described previously. See Nelson et al., *J. Neurochemistry*, 1995, 65: 2350-2357.

(C) Measure of Activation of PKC Isozymes by PKC Activators—

PKC activity of each compound was measured in the absence of diacylglycerol and phosphatidyl-L-serine and PKC-δ and PKC-ε were measured in the absence of added EGTA and $CaCl_2$, as described by Kanno et al., *J. Lipid Res.*, 2006, 47: 1146-1156. Low concentrations of $Ca^{2+}$ are needed because high $Ca^{2+}$ interacts with the PKC phosphatidylserine binding site and prevents activation. Freeze-thawing of the samples more than once was avoided because it was found to greatly reduce the PKC activity and the degree of activation. To determine their PKC isozyme specificity, the compounds were pre-incubated with purified isoforms of PKC for five minutes and the PKC activity was measured radiometrically.

DCPLA-ME was found to activate PKC-ε (but not PKC-α or PKC-δ). FIG. 1 shows that DCPLA-ME produces maximal activity at 0.1 and 1 μM and is relatively specific for PKC-ε. Indeed, DCPLA-ME did not have a major effect on either PKC-α or PKC-δ at the same concentrations. DCPLA-ME activated PKC-ε by more than 50% in a range of 0.01-10 μM, with maximum activation at 100 nM and 1 μM concentrations. At its peak, DCPLA-ME activated PKC-ε up to 190% of control.

Further, DCPLA-ME has less inhibitory effect on $^P$KC-δ than DHA-CP6 and DCPLA This may be an important advantage because downregulation of PKC-δ by PKC activators that bind to the diacylglycerol site (such as phorbol ester) may result in tumor-promoting effects. Further, because PKC-ε and PKC-δ generally have antagonistic effects, inhibition of PKC-δ may be desirable because it may contribute to the efficacy of the drug. In general, PKC-ε and PKC-δ have antagonistic activities in many pathways. As such, it may be desirable to activate PKC-ε while minimizing activation and downregulation of PKC-δ.

Example 2

PKC Activation by DCPLA-Isopropyl Ester and DCPLA-Cyclopropanated Oleyl Ester

Figure 2:
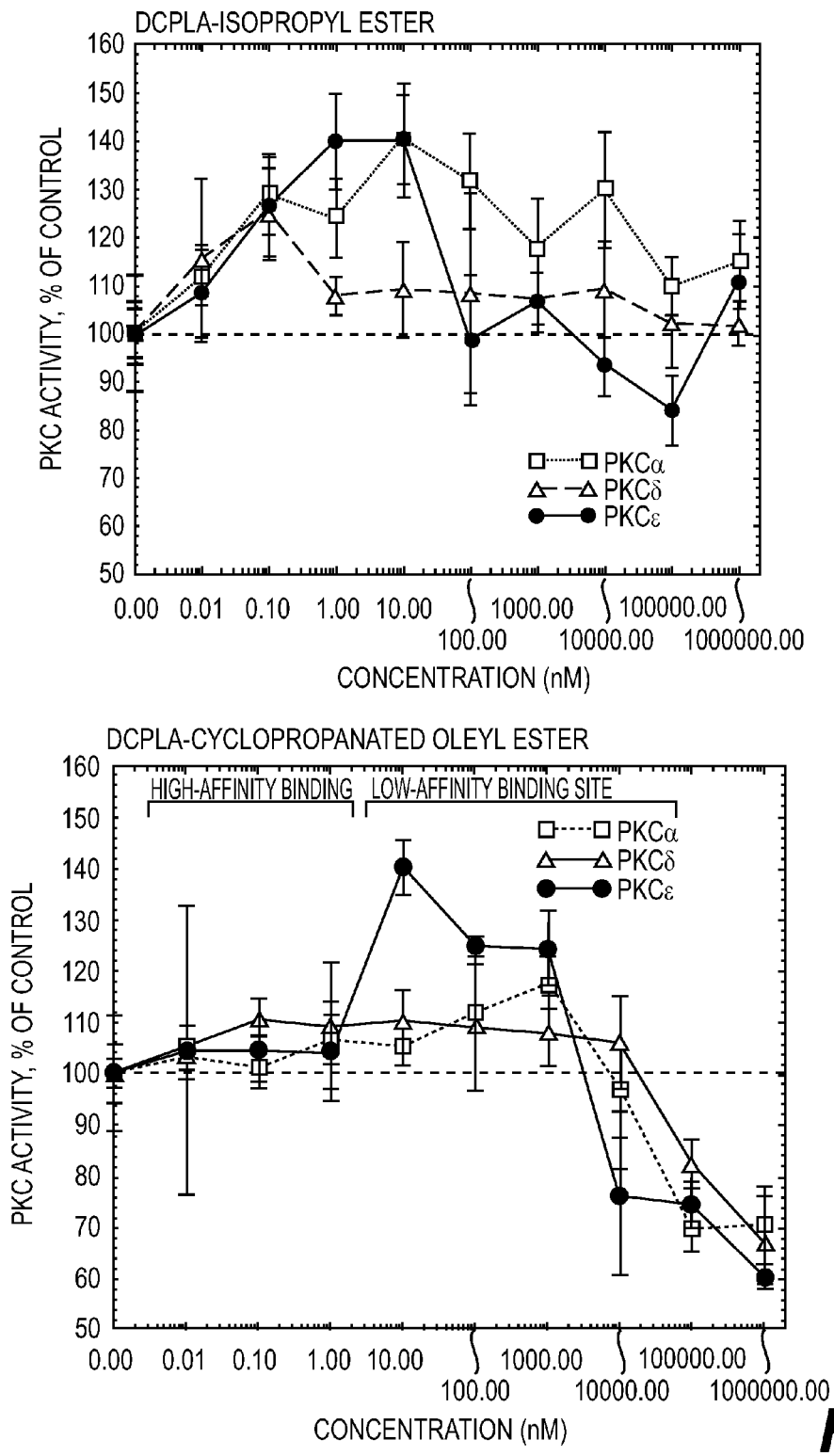
FIG. 2: PKC activation and selectivity of DCPLA-isopropyl ester and DCPLA-cyclopropanated oleyl ester.

Following the procedure in Example 1, the activation and PKC isozyme specificity of DCPLA-isopropyl ester and DCPLA-cyclopropanated Oeyl ester were measured (FIG. 2). DCPLA-isopropyl ester activated both PKC-α and PKC-ε up to 40% of control and only slightly activated PKC-δ. Maximal activation was seen at 10 nM. DCPLA-cyclopropanated Oeyl ester is relatively specific for PKC-ε, exhibiting activation 140% of control. Maximal activation was seen at 10 nM.

Example 3

Figure 3:
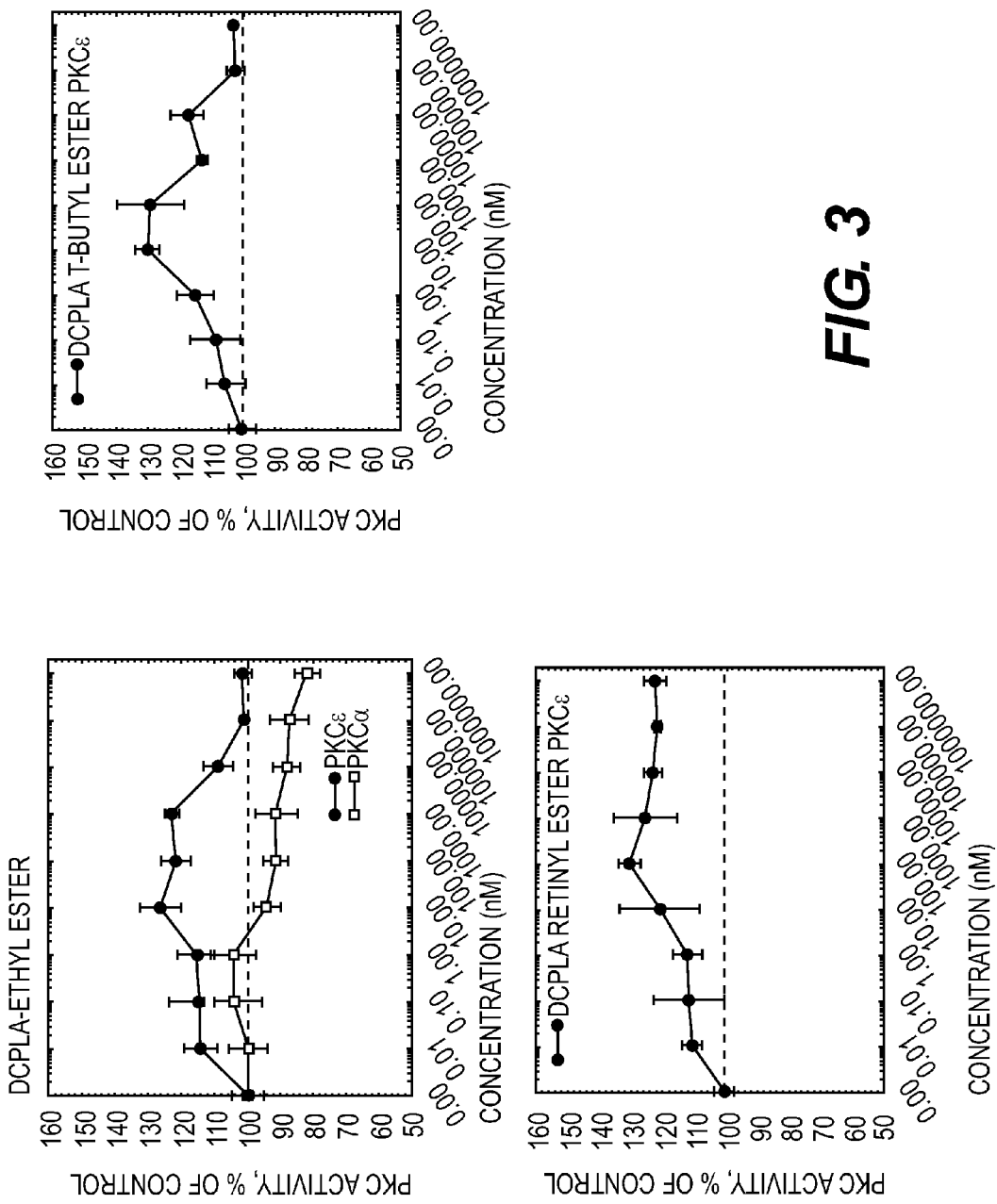
FIG. 3: PKC activation and selectivity of DCPLA-ethyl ester, DCPLA-tert-butyl ester, and DCPLA retinyl ester.

PKC Activation by DCPLA-Ethyl Ester, DCPLA-Tert-Butyl Ester, and DCPLA-Retinyl Ester The activation and PKC isozyme specificity of DCPLA-ethyl ester was measured following the procedures in Example 1(B) and (C), except that 9 ng of the purified isozyme was used and it was pre-incubated for 5 minutes at room temperature (FIG. 3). PKC-ε activation by DCPLA-tert-butyl ester and DCPLA-retinyl ester was measured in the same manner as DCPLA-ethyl ester (FIG. 3).

Example 4

Figure 4:
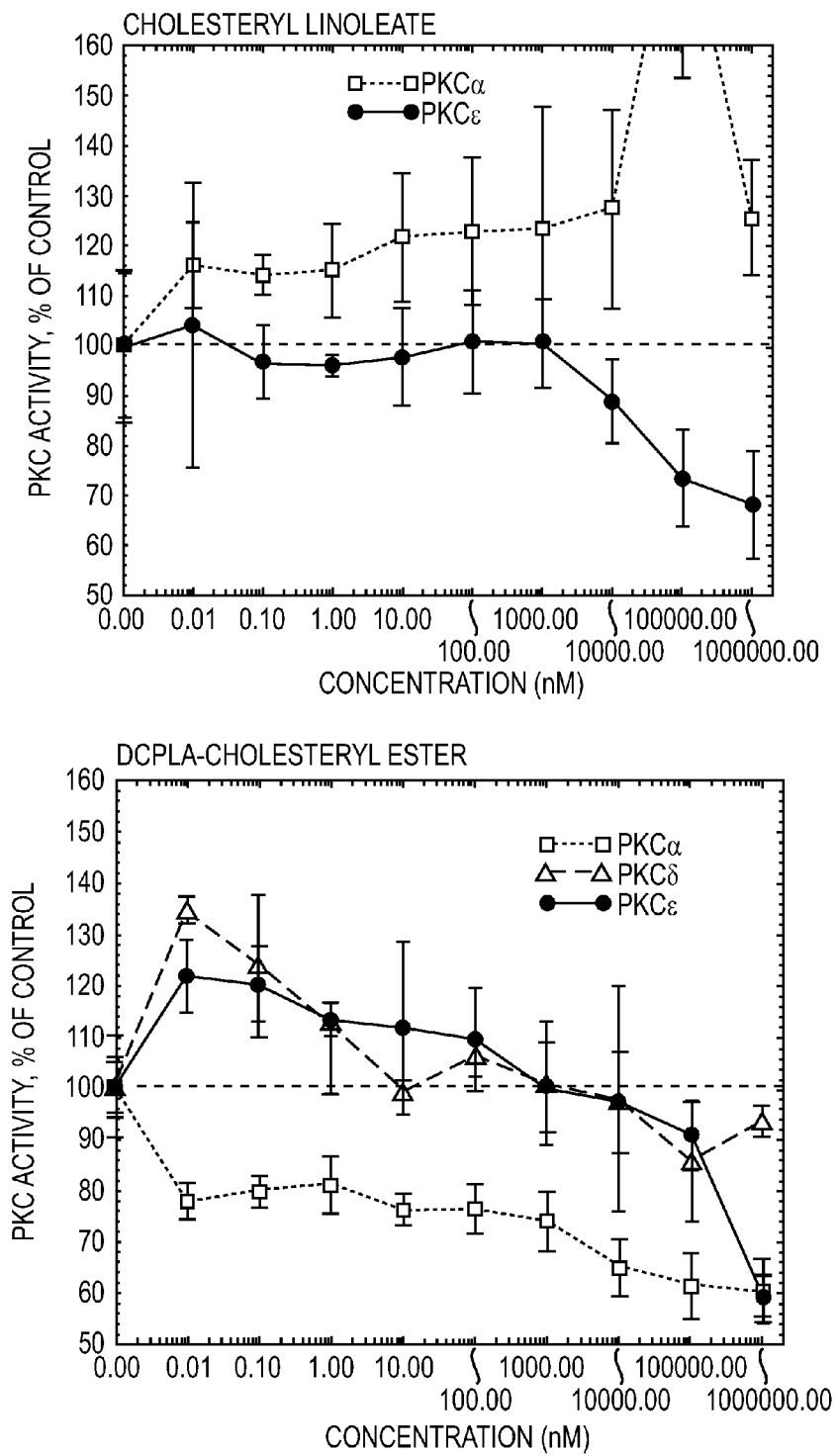
FIG. 4: PKC activation and selectivity of DCPLA-cholesteryl ester compared to cholesteryl linoleate.

DCPLA-Cholesteryl Ester Activates PKC-ε to a Greater Extent than Cholesteryl Linoleate Following the procedure in Example 1, the activation and PKC isozyme specificity of DCPLA-cholesteryl ester and cholesteryl linoleate were measured (FIG. 4). DCPLA-cholesteryl ester activates both PKC-ε and PKC-δ in a biphasic manner by up to 130% of control. PKC-α was inhibited at all concentrations. This ester showed extremely high affinity for PKC-ε and PKC-δ. Maximal activity was seen at 0.01 nM, which is 18× more potent than know PKC activator Bryostatin 1. Cholesteryl linoleate, by contrast, produced little or no activation of PKC-ε and only 20% activation of PKC-α.

Example 5

$EC_{50}$ Values, Specificity and Activation of Select DCPLA Esters

The $EC_{50}$ values, PKC specificity, and activation for a select number of DCPLA esters was determined (see Table 1). $EC_{50}$ values were determined by measuring the lowest concentration that activates by 50% of maximum activation.

Generally, drugs with lower $EC_{50}$ values are considered more potent. As can be seen in Table 1, the esters of DCPLA show much lower $EC_{50}$ values that the corresponding acid, DCPLA. The specificity and activation of PKC by the various esters of DCPLA were determined from the measurements of activation of PKC isozymes.

| Activator | EC50, nM | Specificity[1] ε/α | Activation[2] |
|---|---|---|---|
| DCP-LA | 1000 | 7.4 | 300 |
| DCPLA-methyl ester | 3 | 12.1 | 195 |
| DCPLA-ethyl ester | 3 | 4.2 | 126 |
| DCPLA-isopropyl ester | 0.1 | 1.4 | 140 |
| DCPLA-t-butyl ester | 1 | ND | 130 |
| DCPLA-cyclopropanated oleyl ester | 3 | 8.1 | 140 |
| DCPLA-retinyl ester | 10 | ND | 129 |
| DCPLA-cholesteryl ester | 0.005 | 0.94 | 122 |

[1] Activation of PKC-ε ÷ activation or inhibition of PKCα at $3 \times EC_{50}$.
[2] % of control of PKCε at maximum.
ND = not determined.

Considering the activation data of the various DCPLA esters as a whole, it appears that the DCPLA esters fall into two groups: low-affinity activators (e.g., DCPLA-ME, tert-butyl ester, retinyl ester, and cyclopropanated Oeyl ester), which generally activate PKC-ε at 100-1000 nM, and high-affinity activators (e.g., DCPLA-isopropyl ester and cholesteryl ester), which generally activate PKC-ε at 0.1-1 nM. The compounds generally showed a biphasic response, activating PKC-ε at lower concentrations and inhibiting PKC-ε and other isoforms at higher concentrations.

Some DCPLA esters (e.g., DCPLA-tert-butyl ester and cholesteryl ester) also exhibited a bimodal activation, displaying two distinct levels of PKC activation in the activity vs. concentration plot, suggesting that PKC-ε may possess two phosphatidylserine binding sites of differing affinity.

Example 6

DCPLA-ME Binds to the Phosphatidylserine (C2) Binding Site

To determine the binding site of DCPLA-ME, $^3$H-DCPLA-ME was incubated with rat brain slices in the absence and presence of known C1 and C2 competitors. More specifically, rat brain sections were fixed with formaldehyde, sliced, and incubated with (1) $^3$H-DCPLA-ME alone; (2) $^3$H-DCPLA-ME with DCPLA; (3) $^3$H-DCPLA-ME with Phorbol ester; or (4) $^3$H-DCPLA-ME and Bryostatin 1. After incubation, the slices were washed with a buffer made of 130 mM NaCl, 5 mM MgCl, 5 mM KCl, 1 mM EGTA, and 0.1% bovine serum albumin in 10 mM HEPES-NaOH, pH 7.4, dried, and analyzed with film-autoradiography.

Table 2 shows that DCPLA-ME binds to the same site as DCP-LA, confirming the binding site identified by Kanno et al., *J. Lipid Res.*, 2006, 47: 1146-1156 as the phosphatidylserine (C2) site, and not C1A or C1B, since binding is only slightly inhibited by high concentrations of diacylglycerol (C1-binding-site) agonists.

TABLE 2

| Competitor | Competitor binding site | 30 nM competitor | 1 μM competitor |
|---|---|---|---|
| DCPLA | C2 | 86% | 35% |
| DCPLA methyl ester | C2 | 64% | 37% |
| Phorbol ester (PdBu) | C1 | 100% | 81% |
| Bryostatin 1 | C1 | 100% | 77% |

Example 7

Production and Size Determination of ASPDs and ADDLs

Synthetic ASPDs and ADDLs were prepared as described in the General Procedures section above. The size of the 100 kDa retentates (i.e., the ASPDs) and ADDLs were verified by SEC. The size of these ASPDs was found to be approximately 175 kDa when compared to the size standards subjected to SEC, while ADDLs showed peaks at 18, 16, and 8 kDa.

Example 8

Neurotoxic Effect of Different $A\beta_{1-42}$ Oligomers (ASPDs, <100 kDa Filtrate of ASPD, and ADDLs)

To assess the neurotoxic effect of different sized oligomers, rat primary hippocampal neurons were treated with variable concentrations of these $A\beta_{1-42}$ species for 20 hr. Viability of the treated cells was compared to untreated cells using the MTT assay described above.

Figure 5:
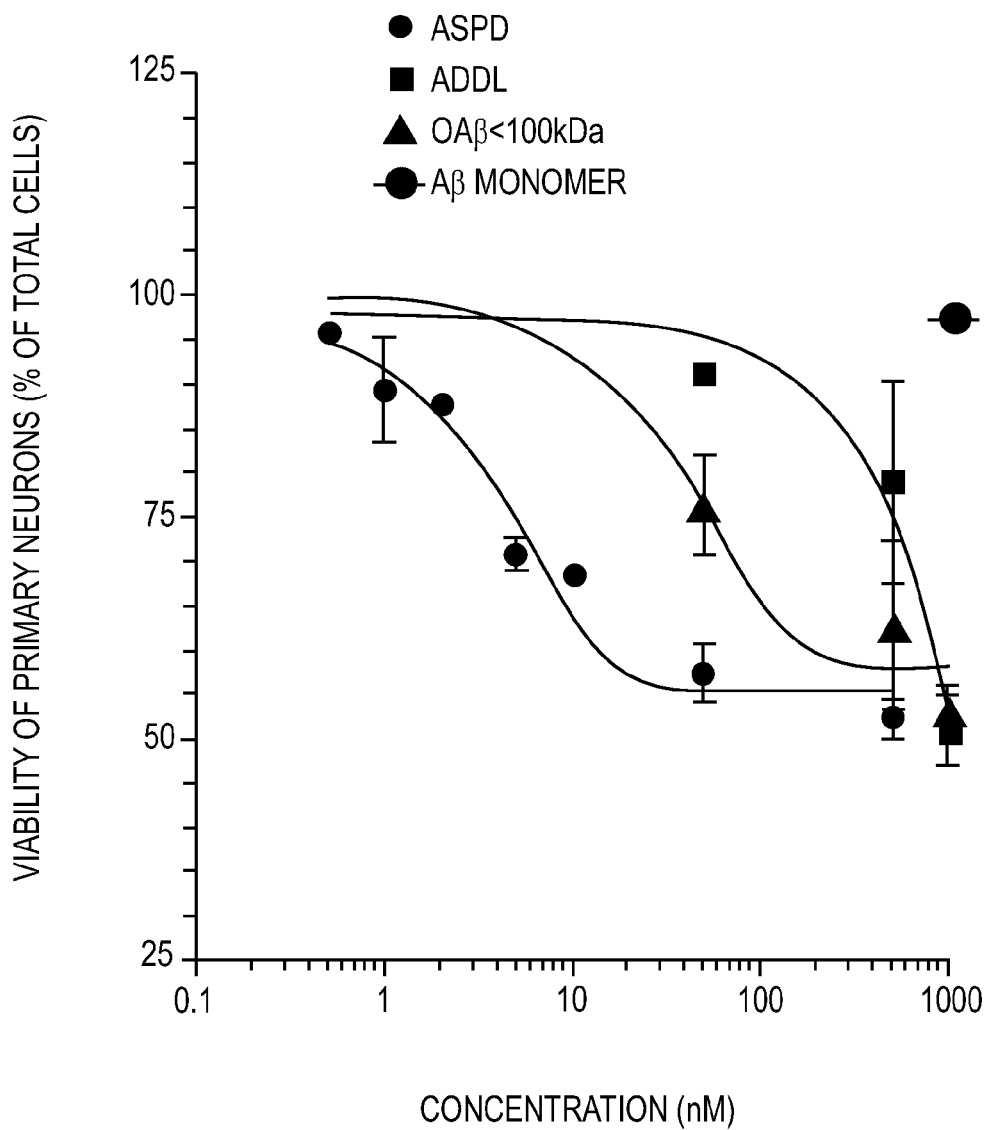
FIG. 5: Neurotoxic effect of different Aβ assemblies. ASPDs, ADDLs, OAβ<100 kDa filtrate, and monomeric Aβ were prepared as described in the Examples section herein and their toxicity on cultured primary rat hippocampal neurons after 20 hr was determined using the MTT assay. ASPDs represent the retentate from the 100 kDa filtration and OAβ represents the filtrate.

As shown in FIG. 5, Aβ monomer at 1 μM concentration did not affect the viability of neurons (97.6%±1.3), while 1 μM ADDL (containing 6.5 monomers on average) significantly killed the neurons (50.98±3.8%, p=0.0013). ASPDs (containing 39 monomers on average) caused a significant decrease in viability at 50 nM (57.1±4.9%, p=0.0028). The OAβ<100 kDa filtrate (containing 12 monomers on average) was significantly cytotoxic at 50 nM, but less toxic than intact ASPDs. Further, it was found that ASPD can cause significant loss of viability at the very low concentrations of 2 nM, 5 nM, and 10 nM (Table 3).

TABLE 3

| | Viability of primary neuron (% of control) | | | | |
|---|---|---|---|---|---|
| Concentration | Untreated (Mean ± SEM) | Aβ Monomer (Mean ± SEM) | ASPD (Mean ± SEM) | ADDL (Mean ± SEM) | oAβ < 100 kDa (Mean ± SEM) |
| 0 nM | 100 ± 4.396 | | | | |
| 0.5 nM | | | 96.12 ± 0.733 (p = 0.2166) | | |
| 1 nM | | | 89.64 ± 5.99 (p = 0.1178) | | |

TABLE 3-continued

| | Viability of primary neuron (% of control) | | | | |
|---|---|---|---|---|---|
| Concentration | Untreated (Mean ± SEM) | Aβ Monomer (Mean ± SEM) | ASPD (Mean ± SEM) | ADDL (Mean ± SEM) | oAβ < 100 kDa (Mean ± SEM) |
| 2 nM | | | 87.75 ± 0.94 (p = 0.026) | | |
| 5 nM | | | 70.95 ± 1.89 (p = 0.0019) | | |
| 10 nM | | | 68.68 ± 0.84 (p = 0.0011) | | |
| 50 nM | | | 57.55 ± 3.35 (p = 0.0028) | 91.15 ± 1.44 (p = 0.117) | 76.41 ± 5.54 (p = 0.023) |
| 500 nM | | | 52.94 ± 3.75 (p = 0.0014) | 79.01 ± 11.32 (p = 0.089) | 62.94 ± 9.53 (p = 0.0155) |
| 1000 nM | | 97.60 ± 1.3 (p = 0.3614) | | 49.02 ± 7.26 (p = 0.0013) | 53.52 ± 2.43 (p = 0.0011) |

The data suggests that ASPDs are the most toxic oligomeric species and 50 nM of ASPDs causes damage equivalent to that caused by 1 μM ADDLs or 1 μM of <100 kDa filtrate (OAβ) of ASPDs. In terms of monomers, ASPDs are 6 times more toxic than ADDLs and 10 times more toxic than Aβ monomer.

All further experiments used 50 nM concentration of ASPDs unless otherwise indicated.

Example 9

Bryostatin 1, DCPLA, and DCPLA-ME Protect Against ASPD Induced Neurotoxicity

PKC activators are reported to provide neuroprotection against Aβ, possibly by activating TACE (tumor necrosis factor-α converting enzyme) and Aβ-degrading enzymes such as endothelin-converting enzyme, insulin degrading enzyme or neprilysin, or by stimulating synaptogenesis.

Figures 6A, 6B:
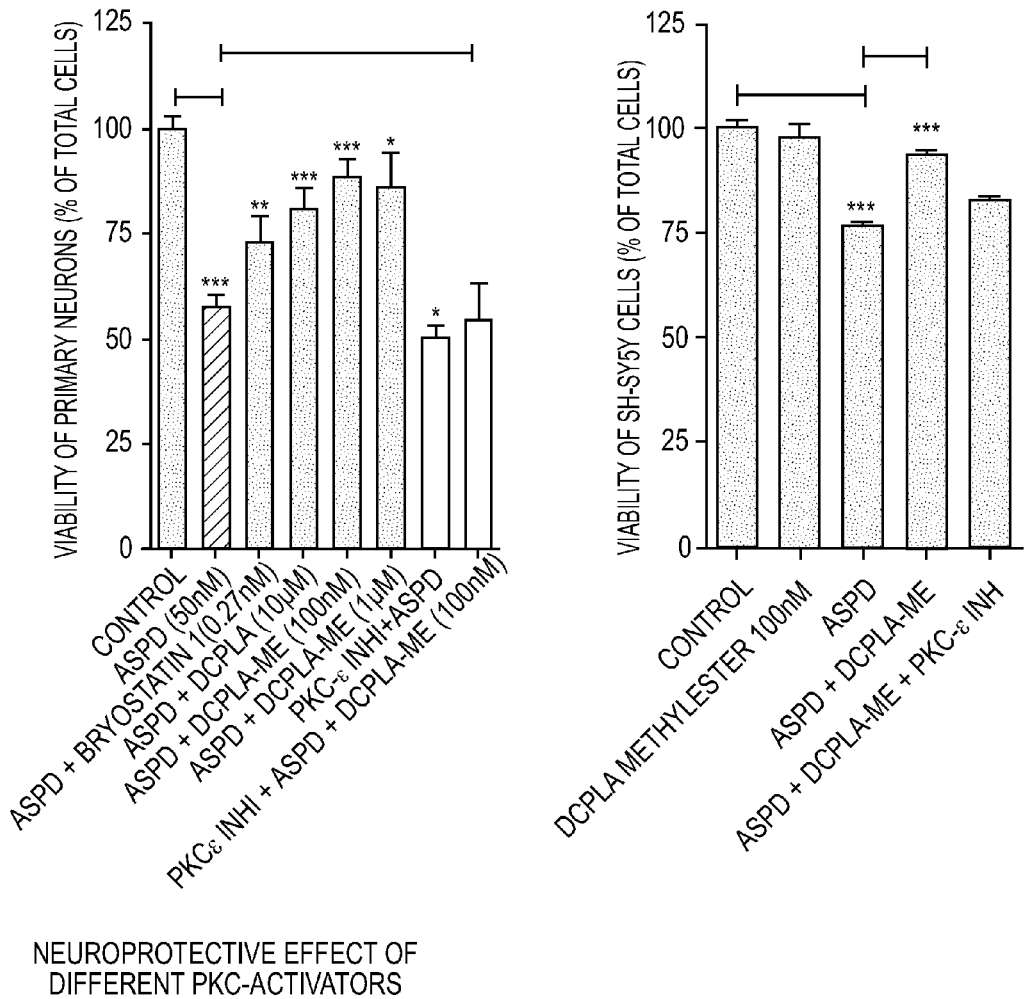
FIGS. 6A and 6B: Neuroprotection by PKC activators (Bryostatin 1, DCPLA, and DCPLA-ME) against ASPD induced toxicity. Cell viability after PKC activator (bryostatin, DCPLA, and DCPLA-ME) treatments in 50 nM ASPD-treated cultured primary rat hippocampal neurons (FIG. 6A) and SH-SY5Y cells (FIG. 6B) was measured by MTT assay as described herein. Viability of neurons and cells treated with DCPLA-ME after treatment with PKC-$\epsilon$ translocation inhibitor peptide [EAVSLKPT] was also measured. Among the PKC activators, DCPLA-ME (100 nM) was found most protective against ASPDs. Data represent mean±SEM. (Student's t test *.p<0.05;, p<0.005 and *, p<0.0005, n=6).

Bryostatin 1, DCPLA, and DCPLA-ME were tested against ASPD-induced cytotoxicity to determine their neuroprotective efficacy. The tested PKC-ε activators were neuroprotective against 20 hr treatment with ASPD in primary neurons (FIG. 6A). Primary neurons treated with 50 nM ASPD showed 57.6±1.6% viability. Bryostatin 1 (0.27 nM), DCPLA (10 μM), and DCPLA-ME (100 nM) treatment restored the viability to 73.23±3.6% (p=0.0083, n=6), 81.43±2.76% (p=0.0009, n=6), and 89.16±2.27% (p=0.0002, n=6), respectively. When added to the cells with DCPLA-ME, the PKC-ε translocation inhibitor peptide [EAVSLKPT] blocked DCPLA-ME's protective effect, suggesting that the neuroprotection against Aβ is mediated by PKC-ε activation.

DCPLA-ME-treated cells were 8% and 16% more viable than DCPLA-treated and Bryostatin 1-treated cells. The data show that DCPLA-ME provides better neuroprotection compared to DCPLA and Bryostatin 1.

The effect of ASPD and DCPLA-ME on differentiated human SH-SY5Y cells was also studied (FIG. 6B). In ASPD-treated cells, the viability was 77.15±0.49% (p<0.0001, n=6) compared to the untreated cells. DCPLA-ME protected the SH-SY5Y cells against ASPD and restored the viability to 93.8±0.57% (p<0.0001, n=6).

Example 10

ASPD Treatment Decreased PKC-ε

PKC-ε is reported to have neuroprotective effects and is known to maintain/repair synaptic structure. See e.g., Nelson, T. J. et al., *Trends Biochem. Sci.*, 2009, 34: 136-145; Hongpaisan, J. et al., *J. Neurosci.*, 2011, 31: 630-643; Hongpaisan, J. et al., *Proc. Natl. Acad. Sci. USA*, 2007, 104: 19571-19576; and Sun, M. K. et al., *Pharmacol. Ther.*, 2010, 127: 66-77. Therefore, to assess if ASPD has an inhibitory action on PKC-ε, the PKC-ε level after ASPD treatment was measured.

Figure 7A:
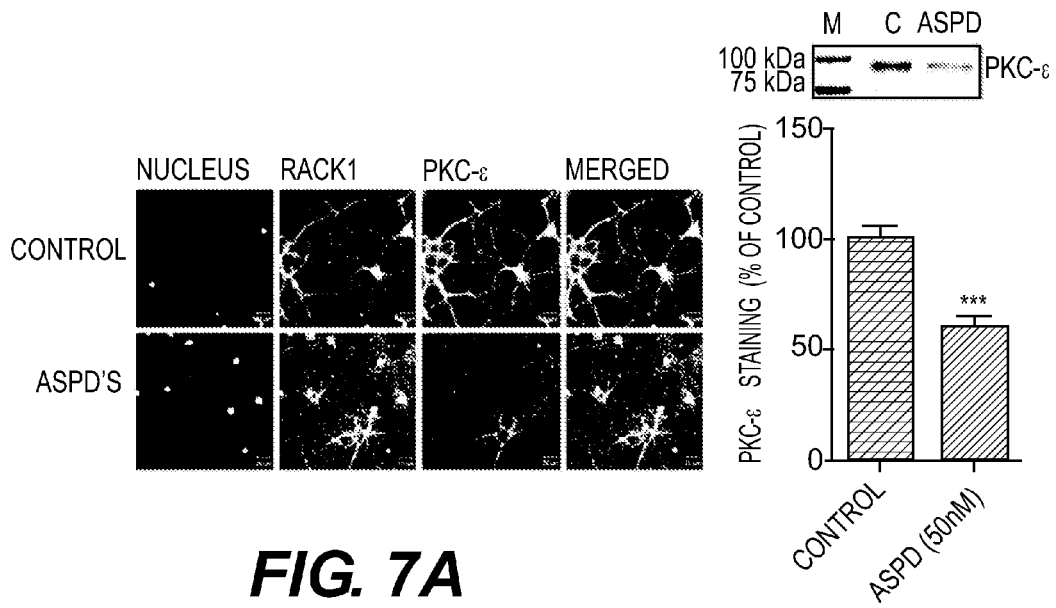
FIG. 7A: ASPD treatment reduces PKC-$\epsilon$ expression. PKC-$\epsilon$ level in cultured primary rat hippocampal neurons was measured by immunofluorescence (n=6) and Western Blot (n=3) as described in the Examples section. For cell staining, 20 hr ASPD-treated cells were washed, fixed, and permeabilized. Cells were then immunostained and imaged in a confocal microscope. Both confocal image analysis and Western Blot showed a significant decrease in PKC-$\epsilon$ level after ASPD treatment. "M" is the molecular weight marker; "C" is the control.

ASPD treatment reduced the PKC-ε immunofluorescence level to 60.81±5.85% compared to control (p=0.0008, n=6) in primary neurons (FIG. 7A), which was further confirmed by Western Blot. Other control proteins, including β-actin, were not affected by ASPD. This suggests that the toxic effects of Aβ multimers may be mediated in part by reduction of PKC.

Figure 7B:
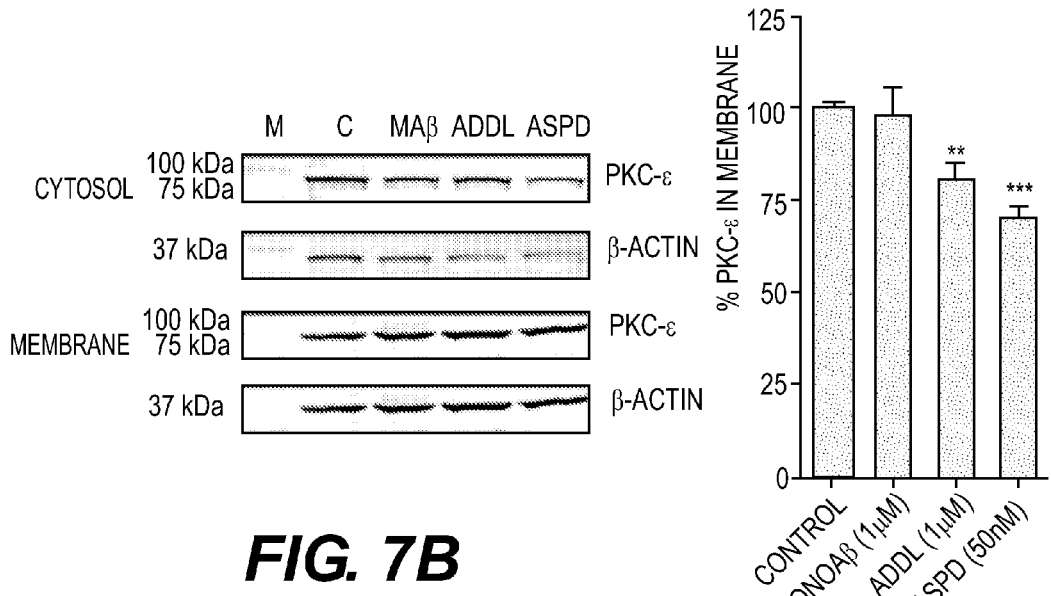
FIG. 7B: PKC-$\epsilon$ translocation to membrane after ASPD and ADDL treatment. Control ("C") and SH-SY5Y neuroblastoma cells treated with monomer Aβ, ADDL, or ASPD were separated into membrane and cytosol fractions and a Western Blot was performed. PKC-$\epsilon$ activation was measured as the percentage of total PKC-$\epsilon$ present in the membrane. Data are represented as mean±SEM. (Student's t test , p<0.005 and *, p<0.0005). "M" is the molecular weight marker; "C" is the control.
Figure 8B:
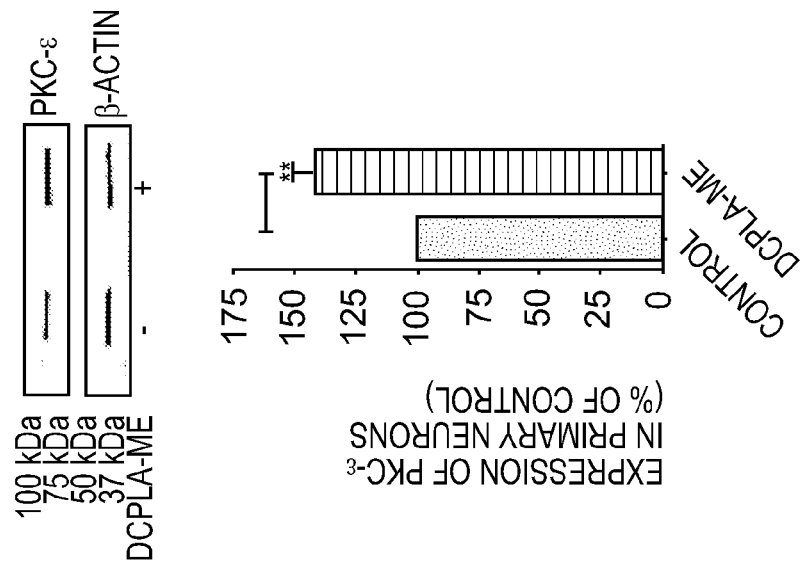
FIG. 8: DCPLA-ME prevents ASPD induced PKC-$\epsilon$ loss. Primary neurons were treated with ASPD and/or DCPLA-ME (FIG. 8A). Data are represented as mean±SEM of normalized PKC-ε value. Western Blot analysis was conducted on: primary neurons treated with 100 nM DCPLA-ME (FIG. 8B); 50 nM ASPD-treated primary neurons treated with DCPLA-ME in the presence and absence of 5 μM PKC-ε inhibitor [EAVSLKPT] (FIG. 8C); and PKC-ε activation in control and treated SH-SY5Y cells (FIG. 8D). PKC-ε expression was normalized to β-actin. Data are represented as mean±SEM of three independent experiments. (Student's t test *.p<0.05;, p<0.005 and *, p<0.0005).
In FIG. 8D, "soluble" represents the PKC-ε remaining in the cytosol while "particulate" represents the PKC-ε present in the membrane. PKC activation was measured as the percentage of total PKC-ε present in the membrane.
Figure 8A:
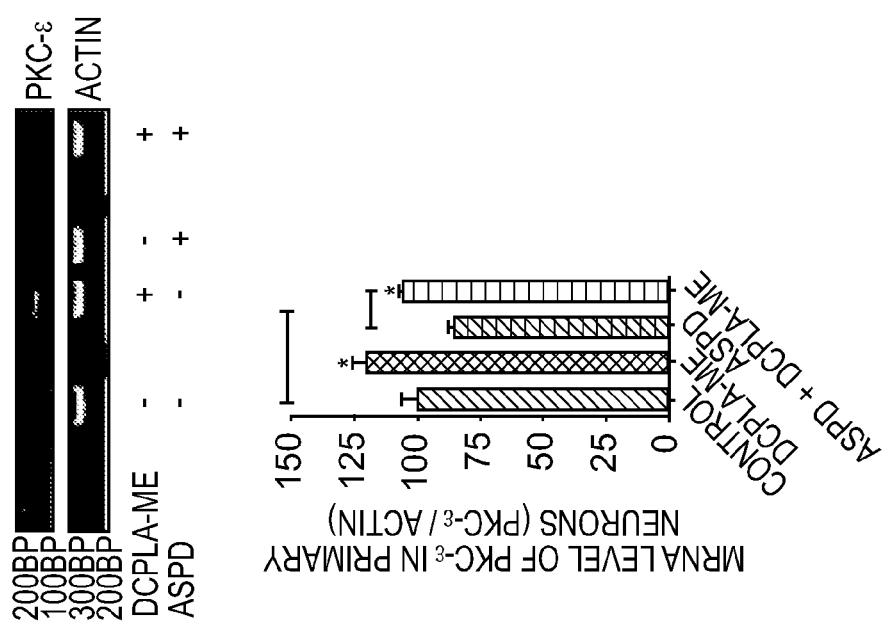
Figure 8D:
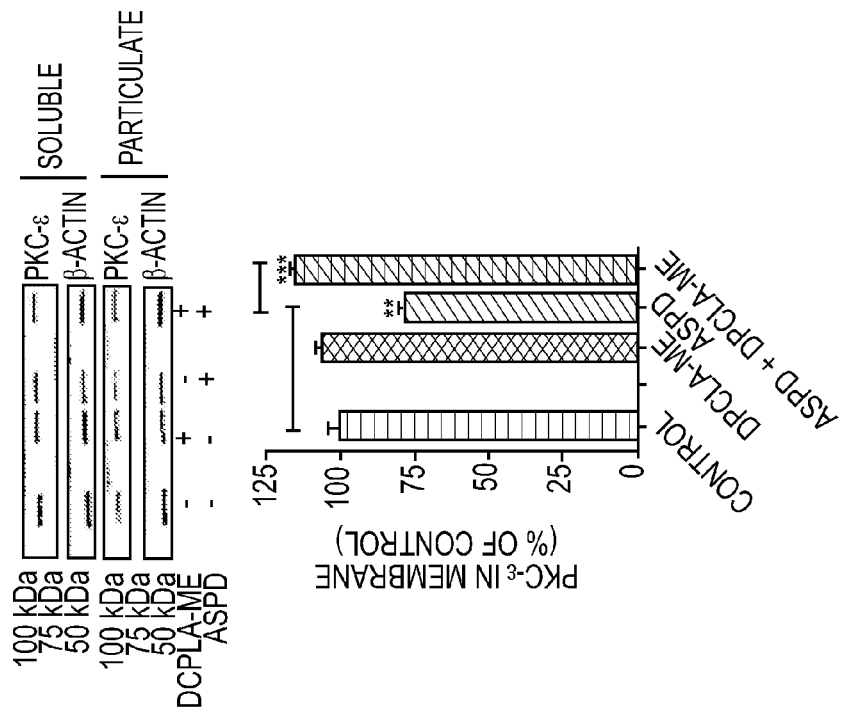

The effect of ASPDs on PKC-ε activation was analyzed by measuring the translocation of the enzyme to the membrane in SH-SY5Y neuroblastoma cells (FIG. 7B). ASPD reduced PKC-ε membrane translocation by 30% (69.98±3.27%, p=0.0006, n=3), while ADDL at 20-fold higher concentrations decreased PKC-ε by only 20% (80.82±4.025%, p=0.0058, n=3). Aβ$_{1-42}$ monomers at 1 μM did not affect translocation. This indicates that low concentrations of ASPDs target PKC-ε by interfering with an upstream signaling pathway leading to its degradation and reduced activation. Addition of DCPLA-ME restored PKC-ε translocation to normal (FIG. 8D).

Example 11

DCPLA-ME Induces Activation of PKC-ε Leading to neuroprotection

Basal PKC-ε level and activation of the enzyme are affected by Aβ oligomers that induced neurotoxicity and that DCPLA-ME treatment helped the cells to survive. The effect of DCPLA-ME on PKC-ε protein levels and activation was next evaluated.

Primary neurons were treated with ASPD and/or DCPLA-ME. PKC-ε mRNA was quantified by RT-PCR as described above. RNA prepared from control and treated cultured primary rat hippocampal neurons were isolated and reverse transcribed. Individual cDNA was amplified for PKC-ε and β-actin. PKC-ε expression was normalized to β-actin.

Figure 8C:
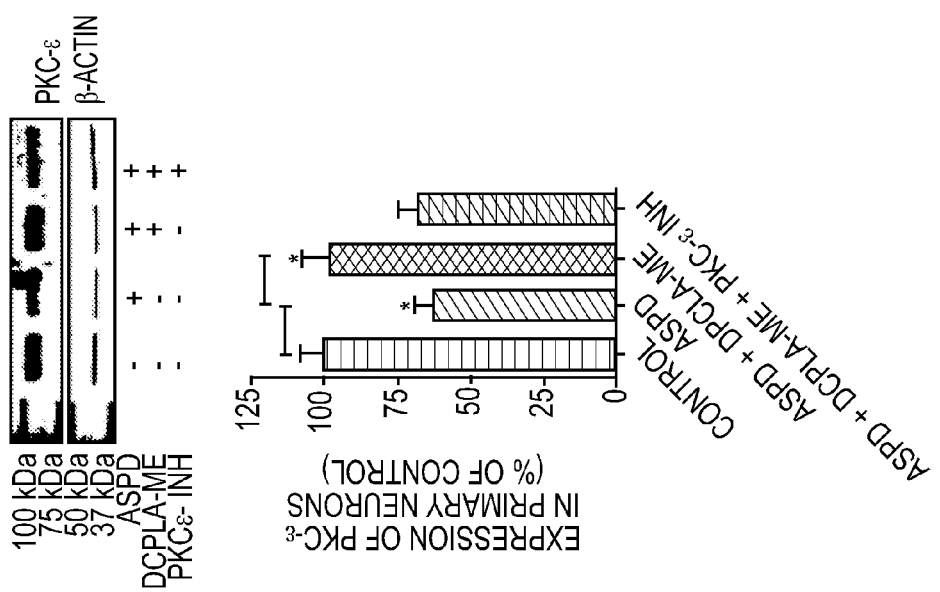

In primary neurons, DCPLA-ME increased PKC-ε transcript levels both in controls and ASPD-treated cells (FIG. 8A), while ASPD alone did not change PKC-ε mRNA significantly. DCPLA-ME also restored the PKC-ε protein level to normal (FIG. 8B). This protection was completely blocked by 5 μM PKC-ε translocation inhibitor [EAVSLKPT] (FIG. 8C). In SH-SY5Y neuroblastoma cells, ASPD reduced PKC-ε translocation by 46%. DCPLA-ME restored PKC-ε translocation to normal (FIG. 8D).

Example 12

ASPD Caused Synaptic Damage

To estimate the synaptic damage caused by the ASPDs on primary hippocampal neurons, the expression of synaptophysin (a presynaptic marker) and PSD-95 (a postsynaptic marker) was measured by immunofluorescence staining. Cells grown on chambered slides were treated with vehicle (control), Aβ monomer (1 µM), ADDLs (1 µM), and ASPD (50 nM). Following a 20 hr incubation period, the cells were stained for nucleus, PSD-95, and synaptophysin. Expression levels were calculated as the change of percentage in mean fluorescence intensity compared to untreated cells.

Figure 9A:
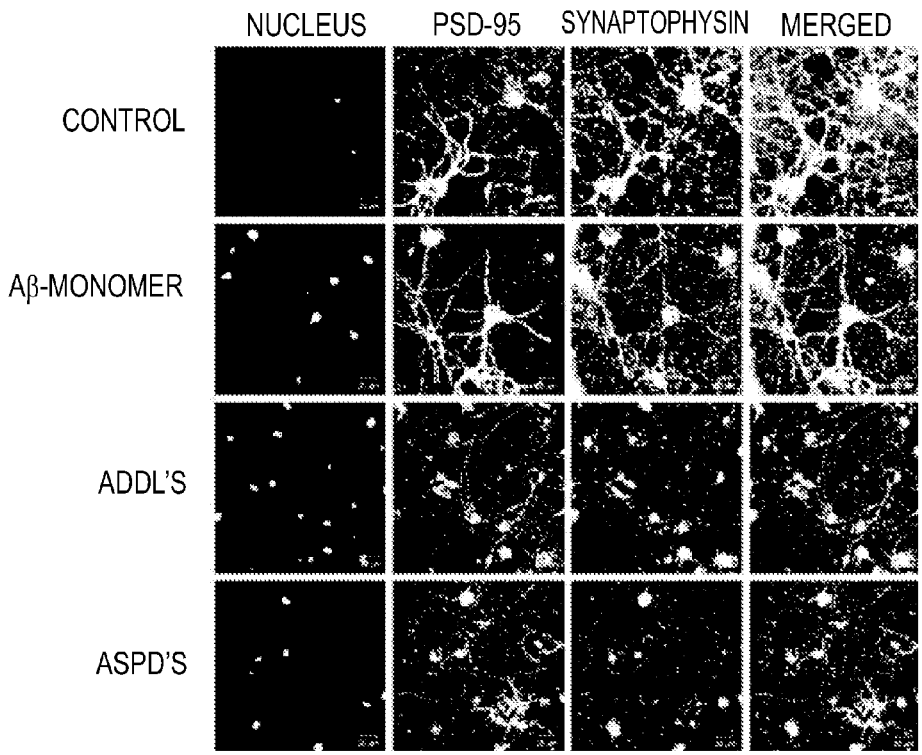
FIG. 9: ASPD induced synaptic loss. Confocal images of rat hippocampal primary neurons are shown in FIG. 9A. The fourth column is the image of the first three columns merged. Mean fluorescence intensity was calculated and was expressed as percentage of control (n=6). Graphical representations of expression level of PSD-95 (FIG. 9B) and synaptophysin (FIG. 9C) are shown. Values are represented as mean±SEM. (Student's t test *.p<0.05; and **, p<0.005).
Figure 9B:
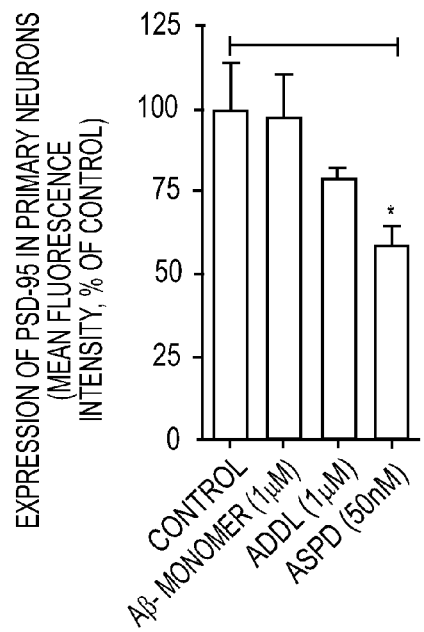
Figure 9C:
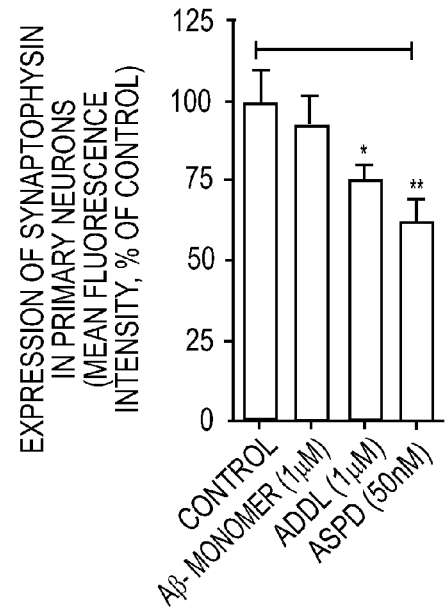

Compared to the control, 50 nM ASPDs caused a 40% decrease in synaptophysin intensity (62.45±6.74%, p=0.0071) and 1 µM ADDLs caused a 25% decrease (75.64±4.84%, p=0.033) (FIGS. 9A and 9C). PSD-95 expression also decreased 42% (±10%) in the ASPD treated cells (FIGS. 9A and 9B). $A\beta_{1-42}$ monomer at 1 µM concentration did not change the expression of synaptophysin or PSD-95. This indicates that ASPDs disrupt synaptic integrity even at nanomolar concentrations.

Example 13

DCPLA-ME Protects Neurons Against ASPD Induced Synaptic Loss

Primary neurons, treated and untreated, were immunostained for MAP-2, synaptophysin, and PSD-95 to determine the synaptic integrity. Cells grown on chambered slides were treated with vehicle (control), 50 nM ASPD, 50 nM ASPD+100 nM DCPLA-ME, and 50 nM ASPD+100 nM DCPLA-ME+5 µM PKC-ε translocation inhibitor [EAVSLKPT]. The PKC-ε inhibitor was added 30 min before adding ASPD and DCPLA-ME. Following a 20 hr incubation period, the cells were stained for MAP-2, PSD-95, and synaptophysin as described above.

Figure 10A:
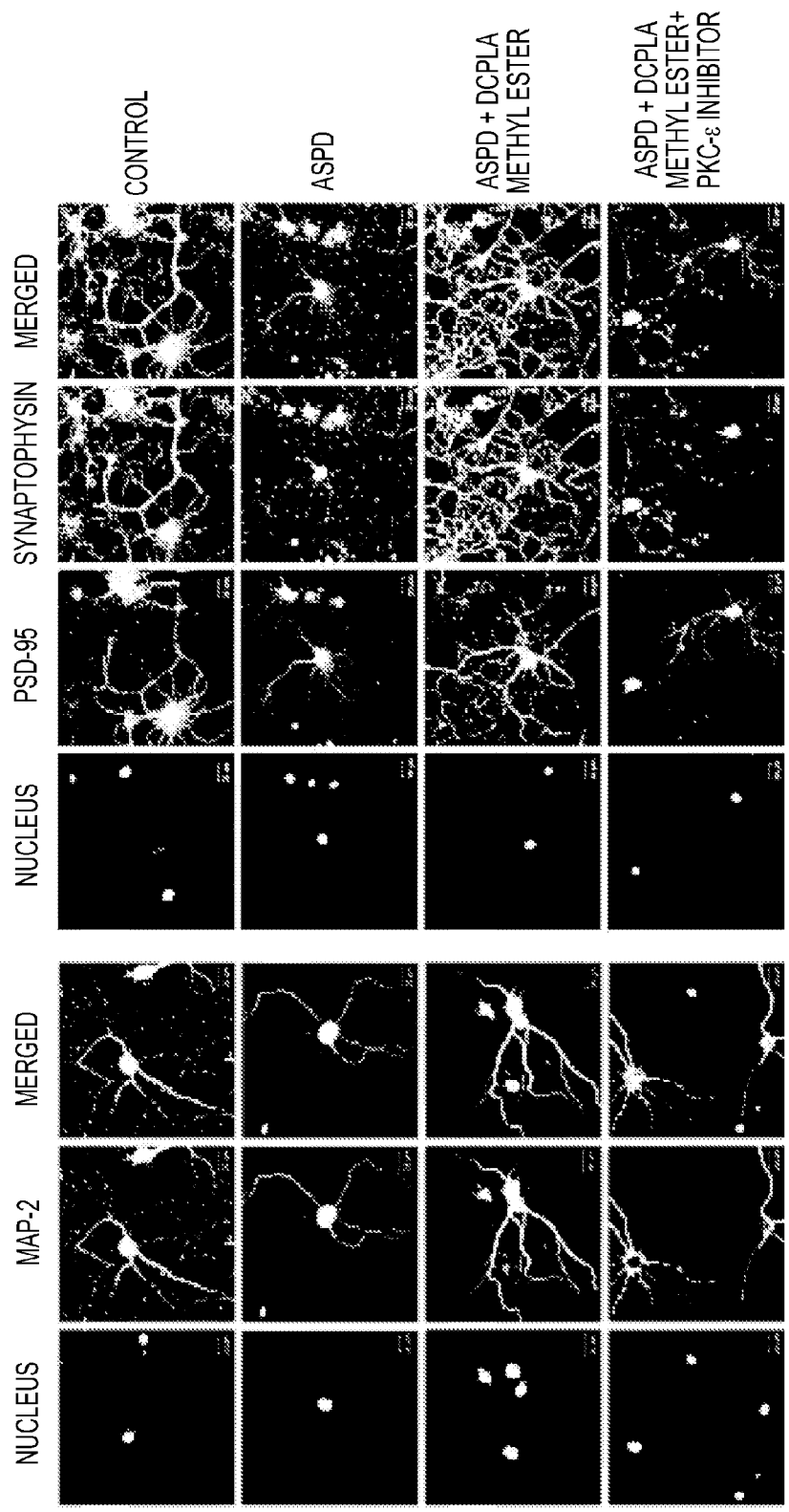
FIG. 10: DCPLA-ME protects from ASPD induced synaptic loss. Confocal images of rat hippocampal primary neurons are shown in FIG. 10A. The first "merged" column is the merge of the prior two columns—i.e., cells stained for nucleus and MAP-2. The second "merged" column is the merge of the three prior columns—i.e., cells stained for nucleus, PSD-95, and synaptophysin. Mean fluorescence intensity was calculated and was expressed as percentage of control (n=6). ASPD treatment showed marked decrease in stained neurite processes, while DCPLA-ME protected against synaptic loss.
FIG. 10C is a Western Blot analysis of synaptophysin expression in control, ASPD, ASPD+DCPLA-ME, and PKC-ε inhibitor [EAVSLKPT]+ASPD+DCPLA-ME treated primary rat hippocampal neurons. Values are represented as mean±SEM. (Student's t test *.p<0.05;, p<0.005 and *, p<0.0005).

It was found that the PSD-95 and synaptophysin staining of the neurites decreased after ASPD treatment, while DCPLA-ME treatment increased their staining in neurite branches (FIG. 10A).

Figure 10C:
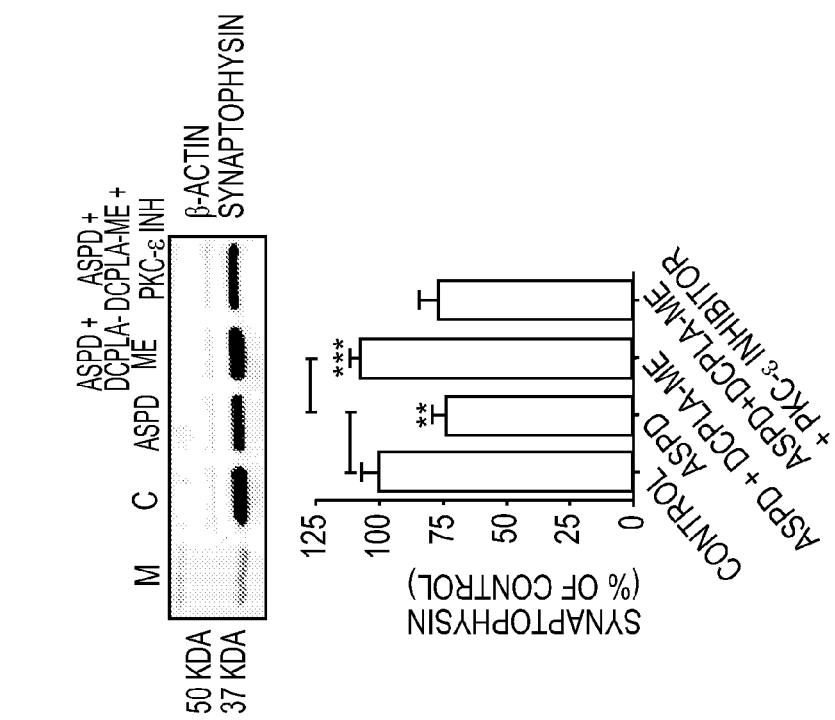
Figure 10B:
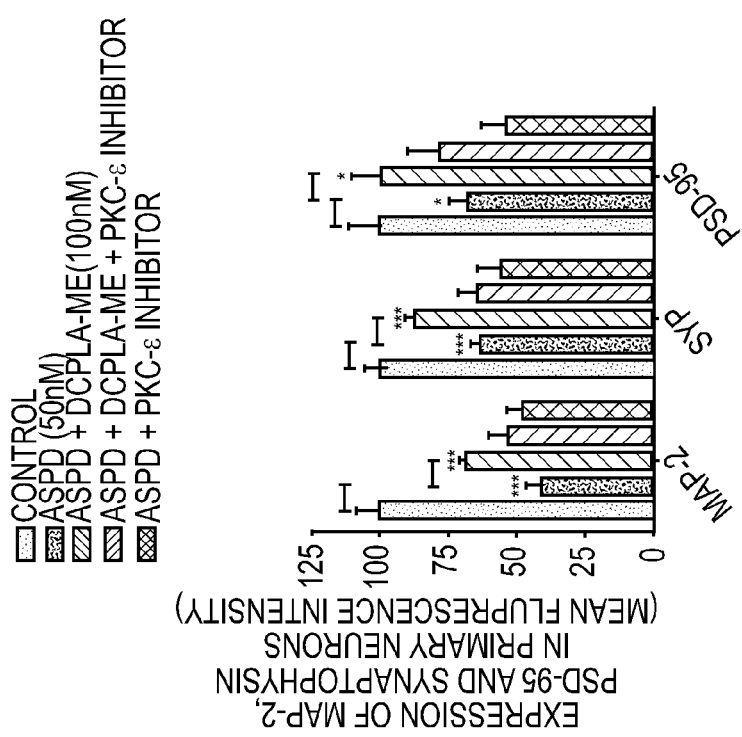

DCPLA-ME treatment increased the expression (mean fluorescence intensity) of MAP-2 in ASPD-treated cells from 40.7±6.2% to 68.87±2.0% (p=0.0007, n=5), synaptophysin from 63.3±3.8% to 87.48±3.75% (p=0.0005, n=5), and PSD-95 from 67.63±7.24% to 99.2±11.3% (p=0.02, n=5) (FIG. 10B). These results suggest that DCPLA-ME not only protected the ASPD cells from cell death but also prevented the synaptic damage by increasing expression of synaptophysin, PSD-95, and MAP-2 in synaptic networks. The expression of synaptophysin was confirmed by Western Blot, and showed that ASPD decreased the expression by 26% (73.30%±3.319, p=0.0035, n=3) and DCPLA-ME treatment maintained the expression similar to control (FIG. 10C).

Example 14

DCPLA-ME Inactivated GSK-3β in ASPD Treated Primary Neurons

Figure 11:
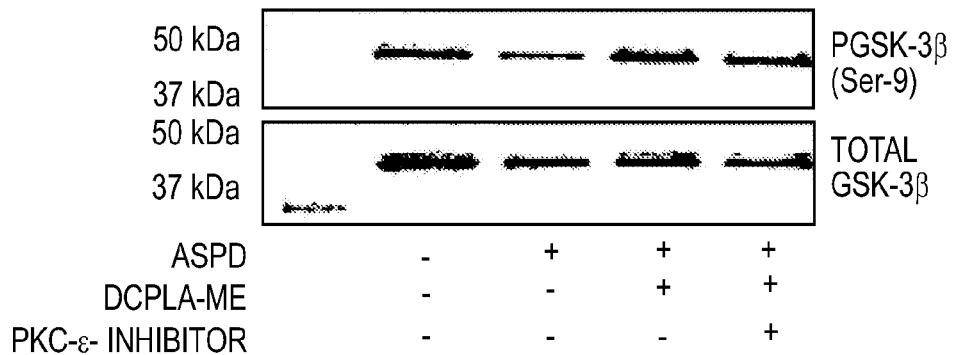
FIG. 11: DCPLA-ME inactivates GSK-3β in ASPD treated primary neurons. Western Blot analysis of phospho GSK-3β (Ser-9) and total GSK-3β protein from rat hippocampal neurons treated with vehicle (control), ASPD (50 nM), ASPD (50 nm)+DCPLA-ME (100 nM), and ASPD (50 nm)+DCPLA-ME (100 nM)+PKC-ε inhibitor (5 μM) [EAVSLKPT]. Phospho GSK-3β expression was normalized against total GSK-3β expression. ASPD treatment activated GSK-3β while DCPLA-ME treatment inactivated GSK-3β. Data are represented as mean±SEM. (Student's t test *.p<0.05; and **, p<0.005 n=3).
Figure 11:
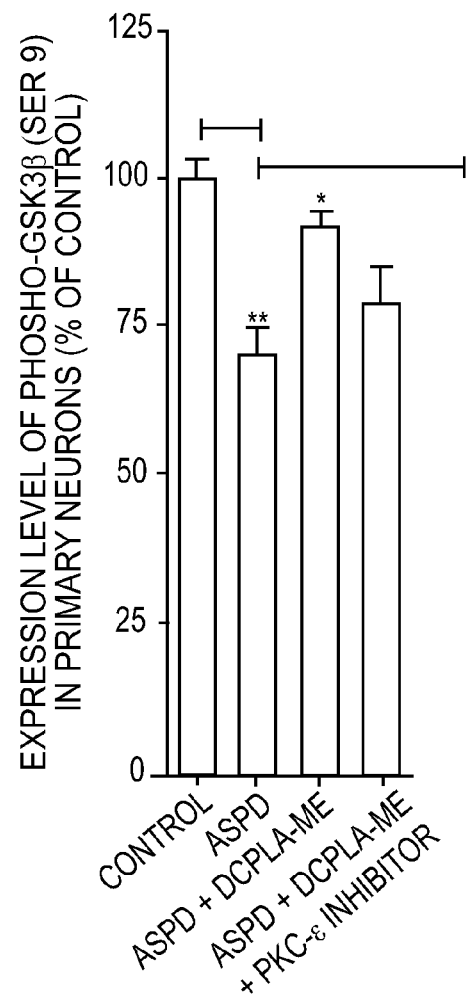

DCPLA-ME treatment of ASPD-treated cells restored phosphorylation of the Ser-9 residue of GSK-3β to normal levels, as evidenced by an increased signal in anti-phospho-Ser-9 Western Blots (FIG. 11). Since GSK-3β is a key enzyme in the production of hyperphosphorylated tau protein, and phosphorylation of the Ser-9 residue causes GSK-3β inhibition, increasing phosphorylation of GSK-3β at Ser-9 by PKC could also enhance the protective effect of DCPLA-M E.

Example 15

DCPLA-ME Leads to Synaptogenesis in Human Cortical Neurons

To examine the effects of PKC-ε activation, cultured human cortical neurons in serum-free artificial medium were exposed to 100 nM DCPLA-ME added every three days, along with 50% medium replacement, for 40 days. More specifically, human primary cortical neurons were grown in Neuronal Medium (ScienCell Cat No#1521) containing neuronal growth supplement (NGS) (Sciencell Cat No#1562).

Composition of NGS—When a 500 ml bottle of NM is supplemented with NGS, the final concentrations of the supplement components per milliliter will be 100 ug BSA, 2.5 ug/mL catalase, 1 ug/mL glutathione (reduced), 4 ug/mL insulin, 0.0026 uM T3, 2 ug/mL L-Carnitine, 16 uM Ethanolamine, 15 ug/mL galactose, 16.1 ug/mL Putrescine, 0.01435 ug/mL Sodium Selenite, 0.02 ug/mL Corticosterone, 0.02 uM Progesterone, 3.5 nM Linoleic Acid, 1 ug/mL linolenic acid, 0.2 uM Lipoic Acod, 0.01 ug/mL Retinyl acetate, 0.1 ug/mL D,L-alpha-tocopherol acetate, and 0.1% ethanol.

Cells were plated on poly-l-lysine (0.001%) coated plates at a density of >10000 cells/cm2. Half of the media was replaced by new media every 3 days. DCPLA-ME was dissolved in 100% ethanol and added at 100 nM final concentration. Fresh DCPLA-ME (100 nM) was added every 3 days during media change. The experiments were continued for 40 days.

Figure 12:
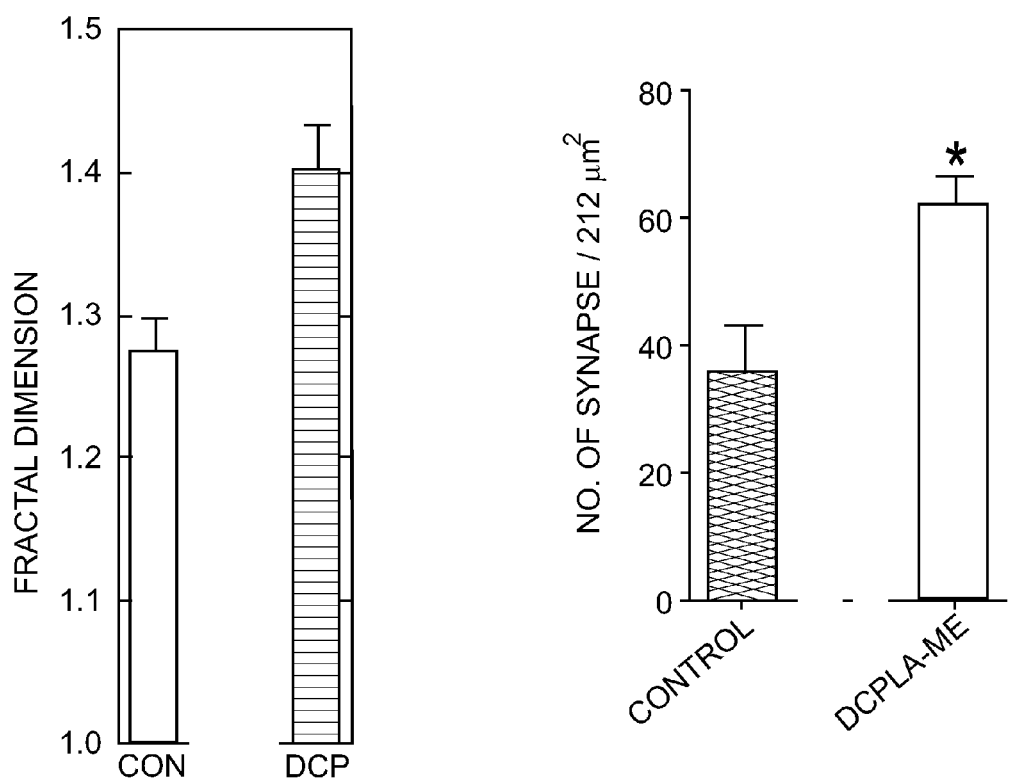
FIG. 12: Effects of DCPLA-ME on cortical neurons. Left: fractal dimension in primary human cortical neurons. Right: synapses/cell in 212×212 μm field. "DCP" is DCPLA methyl ester. (*p<0.03).

DCPLA-ME increased neuronal survival from 20 to over 40 days. The DCPLA-ME-treated cells had 360±45 neurite-positive cells/field compared to 130±8 in the untreated group. DCPLA-ME increased the number of colocalized puncta of synaptophysin and PSD-95, indicative of synapses, to 230% of control (FIG. 12), indicating that PKC-ε activation can induce synaptogenesis in human neurons. Neuritic branching was also increased, as evidenced by an increase in the fractal dimension from 1.27±0.02 to 1.40±0.03 (p=0.03) (FIG. 12). The PKC-ε activation produces a marked growth in network connectivity and complexity in human neurons. Thus, DCPLA esters such as DCPLA-ME could provide a significant therapeutic benefit in a variety of neurological disorders.

Example 16

DCPLA-ME Improves Learning and Memory Retention in a Dose-Dependent Manner without Affecting Sensorimotor Ability or Motivation Water maze spatial learning and memory task (2 training trials/day for 4 days) was used to evaluate effects of oral DCPLA-ME on learning and memory in rats. A visible platform test was conducted after the end of the experiments to evaluate whether the treatment might result in an altered sensorimotor activity and escape motivation.

Male adult Wistar rats (200-250 g) were housed in a temperature-controlled (20-24° C.) room for a week, allowed free access to food and water, and kept on a 12-h light/dark cycle. Rats were anesthetized with sodium pentobarbital (60 mg/kg i.p) and placed in a stereotactic apparatus (Kopf Instruments, Tujunga, Calif.). The core temperature of rats was monitored and kept constant (38.0±0.5° C.) with warming light and pad. Two stainless steel guide cannulas were placed with the tips positioned at the coordinates (anterior-posterior, 0.5 mm; lateral, 1.5 mm; horizontal, 3.2 mm), under aseptic conditions. At the end of surgery and under appropriate anesthesia, rats received (s.c.) banamine (1 mg/kg) and ketoprofen (5 mg/kg) in lactate/Ringer's solution. A 7-day recovery period was allowed before any further experimentation.

On the first day of experiments, all rats were randomly assigned to different groups and swam for 2 min in a 1.5-(diameter)×0.6-m (depth) pool (22±1° C.). On the following day, rats were trained in a two-trial per day task for four consecutive days. Each training trial lasted for up to 2 min, during which rats learned to escape from water by finding a hidden platform that was placed at a fixed location and submerged 1 cm below the water surface. The navigation of the rats was tracked by a video camera. The escape latency and the route of rats' swimming across the pool to the platform were recorded. The quadrant test (1 min) was performed after removing the platform, 24 hr after the last training trial.

Figure 13:
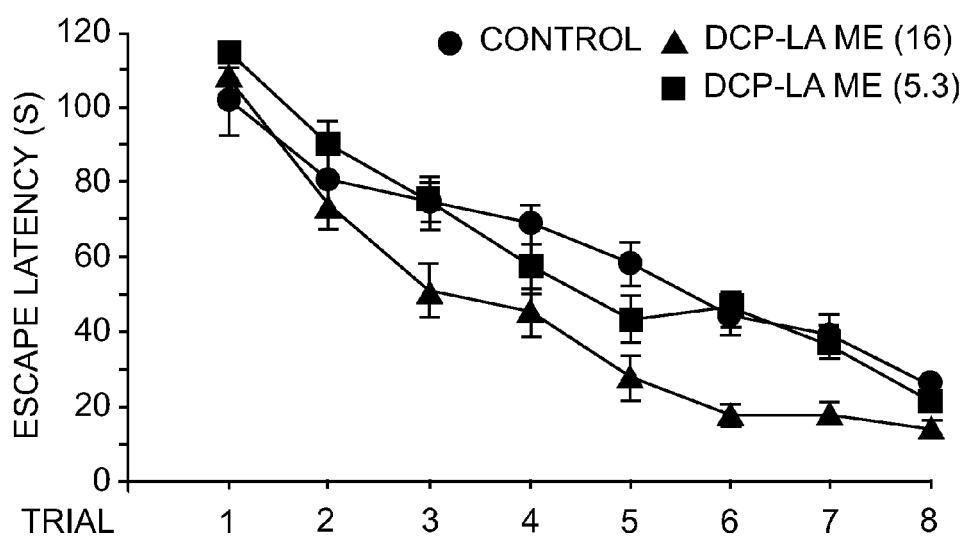
FIG. 13: DCPLA-ME exhibits dose-dependent improvements in learning. DCPLA-ME was administered at either 5.3 mg/kg or 16.0 mg/kg to rats as described in Example 16. The effects were evaluated in a water maze spatial learning test and compared with a control group.
Figure 14A:
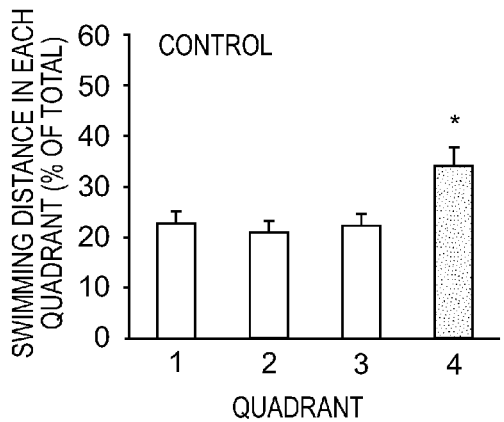
FIG. 14: DCPLA-ME exhibits dose-dependent improvements in memory. DCPLA-ME was administered at either 5.3 or 16.0 mg/kg to rats as described in Example 16. Data were analyzed using a target quadrant ratio.
Figure 14B:
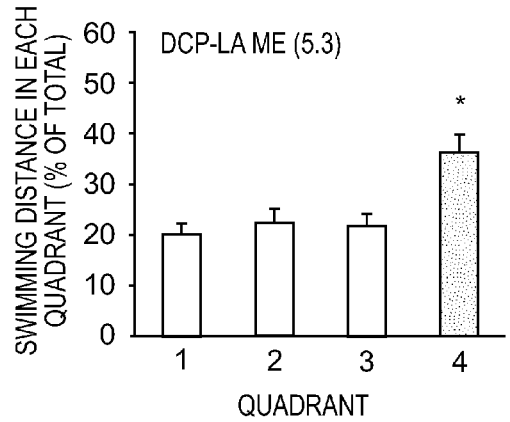
Figure 14C:
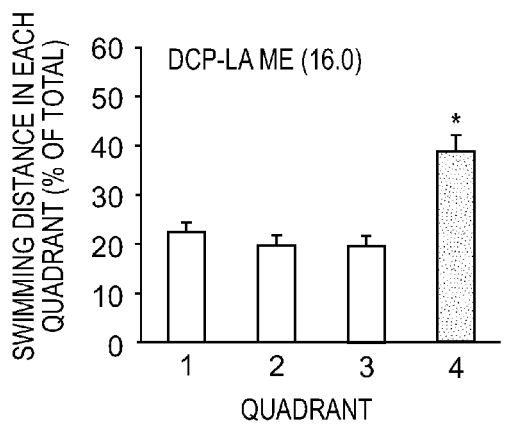
Figure 14D:
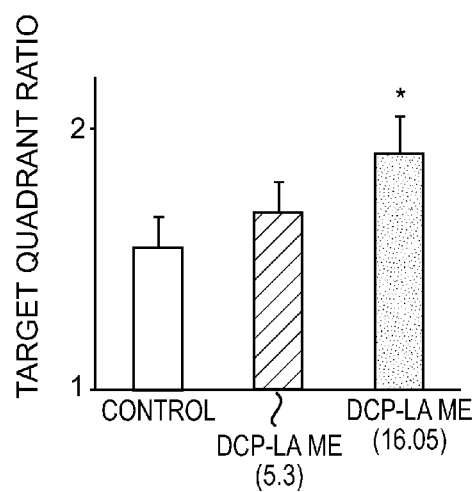

DCPLA-ME was administered at either 5.3 or 16.0 mg/kg (intragastric, 8 doses total of 2/week with the first 6 doses before the water maze task and the seventh and eighth doses 0.5 hr after the second trial of the first and third training day). As shown in FIG. 13, all the rats learned the water maze task, as evidenced by a shorter escape latency over trials ($F_7, 191=19.724$, $p<0.001$). There was a significant difference ($F_{2,191}=7.717$, $p<0.001$) among the groups and a significant difference between the 16.0 mg/kg dose and control groups ($F_{1,127}=13.389$, $p<0.001$), indicating an improved learning performance upon administration of DCPLA-ME. The learning performance improved between the 5.3 mg/kg DCPLA-ME dose and control groups, although this improvement did not reach a significant level ($F_{1,127}=0.657$, $p>0.05$).

In the memory retention test, all the rats showed a target quadrant preference (FIG. 14). Data were analyzed using a target quadrant ratio (dividing the target quadrant distance by the average of the non-target quadrant values during the probe test; FIG. 14D). The data show a significant difference in the target quadrant ratios between the 16.0 mg/kg DCPLA-ME dose and control groups ($F_{1,15}=4.981$, $p<0.05$) but not between the 5.3 mg/kg dose and control groups ($F_{1, 15}=0.397$, $p>0.05$).

At the end of the experiments, the rats were also tested in a visible platform test to evaluate whether the treatment might result in an altered sensorimotor activity and escape motivation. There was no significant difference ($F_{3,31}=1.127$, $p>0.05$; not shown) among the groups in that test, indicating that the oral DCPLA-ME treatment did not affect rats' sensorimotor ability and motivation for an escape.

Example 17

DCPLA-ME Increases Dendritic Branching

The effect of DCPLA-ME on development of primary neurons was investigated. Seven day old rat hippocampal neurons were treated with DCPLA-ME (100 nM) for 48 hr. Immunofluorescence and confocal microscopy-cells were grown in four chambered slides (Nunc, USA) at low density. For immunofluorescence staining the cells were washed with PBS (pH 7.4) and fixed with 4% paraformaldehyde for 4 min. Following fixation, cells were blocked and permeabilized with 5% serum and 0.3% Triton X-100 in 1×PBS for 30 min. Cells were washed 3× with 1×PBS and incubated with primary antibodies for 1 hr at 1:100 dilution. After the incubation slides were again washed 3× in 1×PBS and were incubated with the FITC anti-rabbit IgG and Rhodamine anti-mouse IgG for 1 hr at 1:400 dilution. Cells were further washed and mounted in Pro Long Gold antifade mounting solution (Invitrogen, USA). Stained cells were viewed under the LSM 710 Meta confocal microscope (Zeiss) at 350 nm, 490 nm and 540 nm excitation and 470 nm, 525 nm and 625 nm emission for DAPI, FITC and rhodamine respectively. Six individual fields at 20× or 63× oil lens magnification were analyzed for the mean fluorescence intensity (MFI) in each channel. The colocalization correlation was generated by the ZEN software (Zeiss).

Figure 15A:
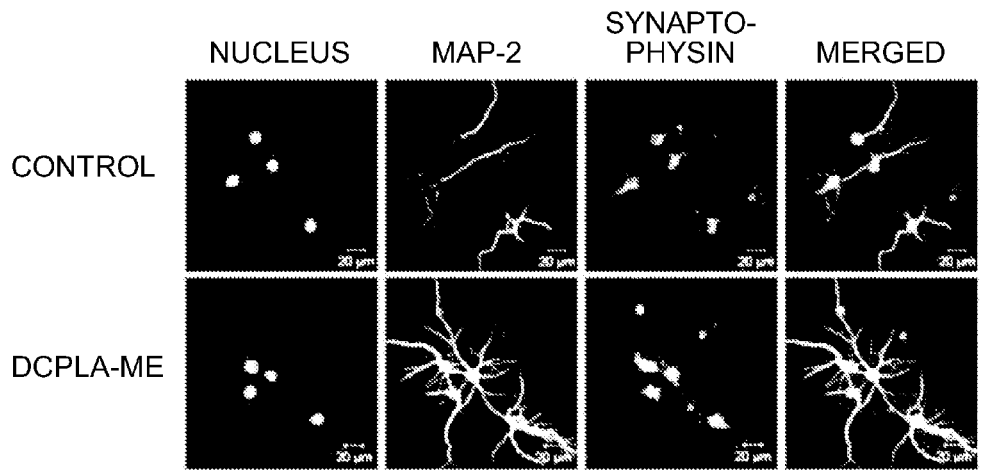
FIG. 15A—Confocal micrographs showing rat hippocampal neurons stained for MAP-2, synaptophysin, and DAPI.
Figure 15B:
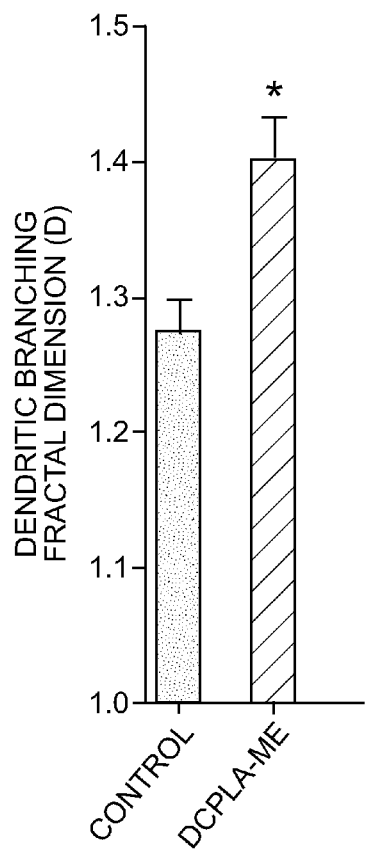
FIG. 15B—Graphical representation of number of dendritic branches per neuron. PKCε activation by DCPLA-ME increase the dendritic branching by 2-fold.
Figure 15C:
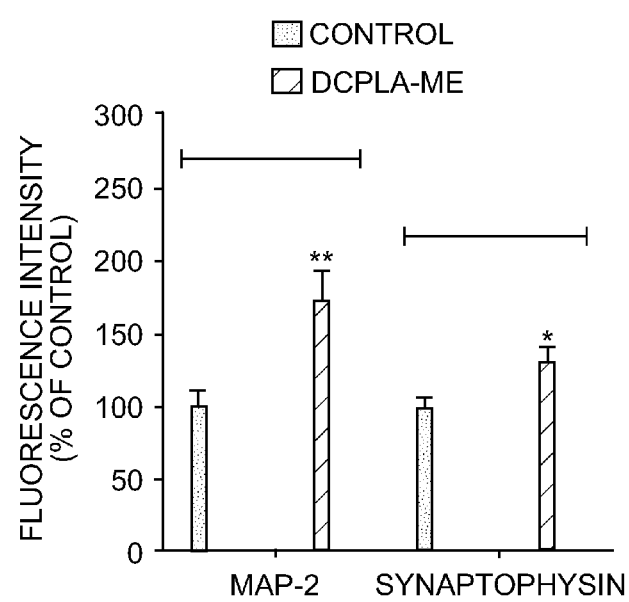
FIG. 15C—Mean fluorescence intensity for MAP-2 or synaptophysin calculated from eight random 225 μm² of confocal images. Data are represented as mean±SE. * represents significance with respect to control (* p<0.05,  p<0.005 and * p<0.0005).

Fractal dimension measures showed significant increase of dendritic branching in the DCPLA-ME (1.40±0.03) treated cells (FIG. 15B). Synaptophysin staining was increased by DCPLA-ME, suggesting an increase in the synaptic vesicle pool (FIG. 15C).

Example 18

PKC Specific Activation by DCPLA-ME Protects Primary Human Neurons from Degeneration Over Time Human primary neurons (ScienCell Research Laboratories, USA) were thawed and plated on poly-L-lysine coated plates at a density of 10,000 cells per $cm^2$ and were maintained in neuronal medium (DMEM+high glucose+neuronal growth supplement, ScienCell Research Laboratories, USA) following the recommended method. Primary human neurons were then treated with either DCPLA-ME (100 nM) or bryostatin 1 (0.27 nM) for 40 days. Fresh drug was added every third day with 50% media change.

Figure 16H:
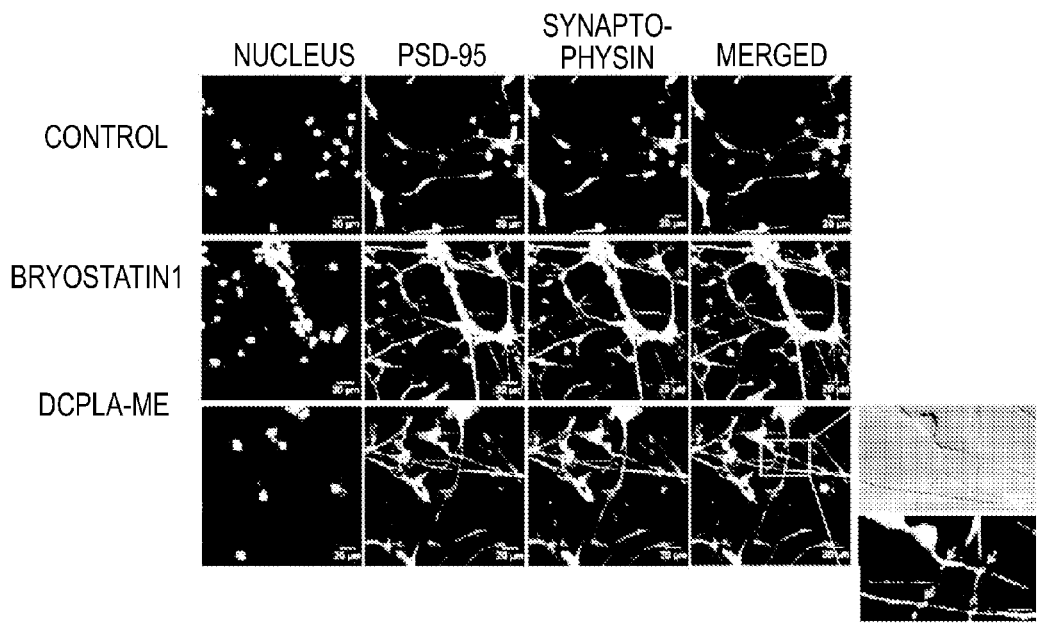
FIG. 16H—Confocal images of 30 day old neurons. DCPLA-ME and bryostatin 1 increased co-localized staining of PSD-95 and synaptophysin in puncta, indicating an increase in the number of synapses. Inset shows enlarged region illustrating a typical synapse.
Figure 16I:
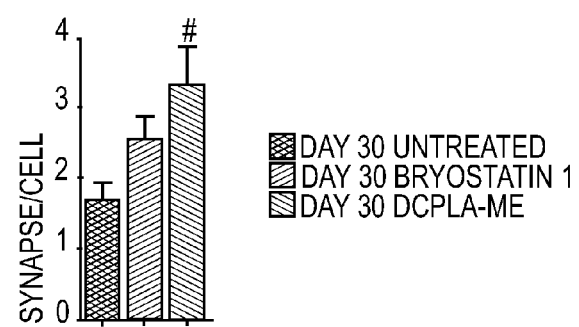
FIG. 16I—Number of synapses per cell increased in DCPLA-ME treated cells. Data are represented as mean±SE * represents significance with respect to day 1 neurons and # represents significance with respect to untreated 40 day or 30 day neurons. (* p<0.05,  p<0.005 and * p<0.0005).

Cells treated with either DCPLA-ME or bryostatin 1 showed a better survival with neuritic branching and connections. (FIG. 16A). Untreated cells showed degeneration after 20 days, while the treated cells were healthy for at least 40 days (FIG. 16B). Expression levels of PKCϵ, PSD-95 and synaptophysin were significantly higher in the DCPLA-ME-treated cells compared to control or bryostatin 1-treated cells (FIGS. 16C, D, E, F & G).

Punctate colocalization of PSD-95 and synaptophysin is accepted as an indicator of synapses. See, e.g., Barker et al. (2008) *J Neurosci* 28, 8150-8160; Ippolito et al. (2010) *J Vis Exp* 16(45), 2270. FIG. 7H shows that the number of synapses was significantly increased in the DCPLA-ME treated cells, suggesting that PKC-ϵ and PKC-ϵ activation enhances synaptogenesis or synaptic maintenance.

What is claimed is:

1. An ester of 8-[2-(2-pentylcyclopropylmethyl)-cyclopropyl]-octanoic acid (DCPLA),
   wherein the ester is chosen from alkyl esters, benzyl esters, aromatic esters, fatty alcohol esters, fatty acid esters, cyclopropanated fatty alcohols esters, cyclopropanated fatty acid esters, diacylglycerol esters, phosphatidyl serine esters, cholesterol esters, and macrolide esters,
   with the proviso that the ester is not the methyl ester.

2. The ester of claim 1 chosen from:
   ethyl 8-(2-((2-pentylcyclopropyl)methyl)cyclopropyl)octanoate (DCPLA-ethyl ester);
   isopropyl 8-(2-((2-pentylcyclopropyl)methyl)cyclopropyl)octanoate (DCPLA-isopropyl ester);
   tert-butyl 8-(2-((2-pentylcyclopropyl)methyl)cyclopropyl)octanoate (DCPLA-tert-butyl ester);
   benzyl 8-(2-((2-pentylcyclopropyl)methyl)cyclopropyl) octanoate (DCPLA-benzyl alcohol ester);

8-(2-octylcyclopropyl)octyl 8-(2-((2-pentylcyclopropyl)methyl)cyclopropyl) octanoate (DCPLA-cyclopropanated oleyl ester);

(2E,4E,6E,8E)-3,7-dimethyl-9-(2,6,6-trimethylcyclohex-1-en-1-yl)nona-2,4,6,8-tetraen-1-yl 8-(2-((2-pentylcyclopropyl)-methyl)cyclopropyl) octanoate (DCPLA-retinyl ester);

(2E,4E,6E,8E)-8-(2-((2-pentylcyclopropyl)methyl)cyclopropyl)octyl 3,7-dimethyl-9-(2,6,6-trimethylcyclohex-1-en-1-yl)nona-2,4,6,8-tetraenoate (retinoic acid-DCPLA alcohol ester);

(8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl 8-(2-((2-pentylcyclopropyl)-ethyl)cyclopropyl) octanoate (DCPLA-cholesteryl ester);

(2Z,2'E)-dimethyl 2,2'-((1S,3S,7R,11S,12S,15S,17R,21R,25S,E)-25-acetoxy-1,11,21-trihydroxy-10,10,26,26-tetramethyl-12-((2E,4E)-octa-2,4-dienoyloxy)-19-oxo-17-((1R)-1-((8-(2-((2-pentylcyclopropyl)methyl)cyclopropyl)octanoyl)oxy)ethyl)-18,27,28,29-tetraoxatetracyclo[21.3.1.13,7.111,15]nonacos-8-ene-5,13-diylidene)diacetate; and (2Z,2'E)-dimethyl 2,2'-((1S,3S,7R,11S,12S,15S,17R,21R,25S,E)-1,11,21-trihydroxy-10,10,26,26-tetramethyl-12-((2E,4E)-octa-2,4-dienoyloxy)-19-oxo-25-((8-(2-((2-pentylcyclopropyl)methyl)-cyclopropypoctanoyl)oxy)-17-(1-((8-(2-((2-pentylcyclopropyl)methyl)-cyclopropyl)octanoyl)oxy)ethyl)-18,27,28,29-tetraoxatetracyclo[21.3.1.1$^{3,7}$.1$^{11,15}$]nonacos-8-ene-5,13-diylidene)diacetate.

3. A composition comprising at least one ester of 8-[2-(2-pentylcyclopropylmethyl)-cyclopropyl]-octanoic acid (DCPLA) and a pharmaceutically acceptable carrier, wherein the ester is chosen from alkyl esters, benzyl esters, aromatic esters, fatty alcohol esters, fatty acid esters, cyclopropanated fatty alcohols esters, cyclopropanated fatty acid esters, diacylglycerol esters, phosphatidyl serine esters, cholesterol esters, and macrolide esters.

4. The composition according to claim 3, wherein the ester is chosen from methyl ester, ethyl ester, isopropyl ester, tert-butyl ester, oleyl ester, retinyl ester, cyclopropanated oleyl ester, cholesteryl ester, Bryostatin 1 ester, and 1-palmitoyl-2-oleoyl-glycerol ester.

5. The composition according to claim 3, wherein the ester is chosen from methyl ester, isopropyl ester, cholesteryl ester, and cyclopropanated oleyl ester.

6. The composition according to claim 3, wherein the ester is the methyl ester.

7. The composition according to claim 3, wherein the ester is present in an amount effective for improving learning, for improving memory, for reducing β-amyloid levels, for treating a disease associated with synaptic loss or synaptic damage, for treating neurodegenerative disorders and conditions, for treating depression, for preventing or treating stroke, for treating mental retardation, and for treating brain injuries.

8. The composition according to claim 3, wherein the composition is suitable for oral or intravenous administration.

9. A method for improving learning comprising:
administering to a patient in need thereof an effective amount of at least one ester of 8-[2-(2-pentylcyclopropylmethyl)-cyclopropyl]-octanoic acid (DCPLA), wherein the ester is chosen from alkyl esters, benzyl esters, aromatic esters, fatty alcohol esters, fatty acid esters, cyclopropanated fatty alcohols esters, cyclopropanated fatty acid esters, diacylglycerol esters, phosphatidyl serine esters, cholesterol esters, and macrolide esters.

10. A method for improving memory comprising: administering to a patient in need thereof an effective amount of at least one ester of 8-[2-(2-pentylcyclopropylmethyl)-cyclopropyl]-octanoic acid (DCPLA), wherein the ester is chosen from alkyl esters, benzyl esters, aromatic esters, fatty alcohol esters, fatty acid esters, cyclopropanated fatty alcohols esters, cyclopropanated fatty acid esters, diacylglycerol esters, phosphatidyl serine esters, cholesterol esters, and macrolide esters.

11. A method for reducing β-amyloid levels comprising: administering to a patient in need thereof an effective amount of at least one ester of 8-[2-(2-pentylcyclopropylmethyl)-cyclopropyl]-octanoic acid (DCPLA), wherein the ester is chosen from alkyl esters, benzyl esters, aromatic esters, fatty alcohol esters, fatty acid esters, cyclopropanated fatty alcohols esters, cyclopropanated fatty acid esters, diacylglycerol esters, phosphatidyl serine esters, cholesterol esters, and macrolide esters.

12. A method for treating a disease comprising: administering to a patient in need thereof an effective amount of at least one ester of 8-[2-(2-pentylcyclopropylmethyl)-cyclopropyl]-octanoic acid (DCPLA),
wherein the ester is chosen from alkyl esters, benzyl esters, aromatic esters, fatty alcohol esters, fatty acid esters, cyclopropanated fatty alcohols esters, cyclopropanated fatty acid esters, diacylglycerol esters, phosphatidyl serine esters, cholesterol esters, and macrolide esters,
and wherein the at least one disease or condition is chosen from neurodegenerative disorders and conditions, depression, stroke, and brain injuries.

13. The method according to claim 12, wherein the neurodegenerative disorder is chosen from Alzheimer's disease.

14. The method according to claim 12, wherein the neurodegenerative disorder or condition is caused by exposure to at least one neurotoxic chemical.

15. The method according to claim 14, wherein the at least one neurotoxic chemical is a heavy metal.

16. The method according to claim 12, wherein the condition is stroke.

17. The method according to claim 12, wherein the condition is a brain injury.

18. The method according to claim 17, wherein the brain injury is traumatic brain injury or brain injury induced by irradiation.

19. The method according to any one of claims 9-12, wherein the ester is chosen from methyl ester, ethyl ester, isopropyl ester, tert-butyl ester, oleyl ester, retinyl ester, cyclopropanated oleyl ester, cholesteryl ester, Bryostatin 1 ester, and 1-palmitoyl-2-oleoyl-glycerol ester.

20. The method according to any one of claims 9-12, wherein the ester is chosen from methyl ester, isopropyl ester, cholesteryl ester, and cyclopropanated oleyl ester.

21. The method according to any one of claims 9-12, wherein the ester is the methyl ester.

* * * * *